(12) United States Patent
Guevremont et al.

(10) Patent No.: US 6,621,077 B1
(45) Date of Patent: Sep. 16, 2003

(54) APPARATUS AND METHOD FOR ATMOSPHERIC PRESSURE-3-DIMENSIONAL ION TRAPPING

(75) Inventors: Roger Guevremont, Gloucester (CA); Randy Purves, Gloucester (CA)

(73) Assignee: National Research Council Canada, Ottawa (CA)

(*) Notice: Subject to any disclaimer, the term of this patent is extended or adjusted under 35 U.S.C. 154(b) by 0 days.

(21) Appl. No.: 09/762,237

(22) PCT Filed: Aug. 5, 1999

(86) PCT No.: PCT/CA99/00718

§ 371 (c)(1),
(2), (4) Date: Apr. 12, 2001

(87) PCT Pub. No.: WO00/08457

PCT Pub. Date: Feb. 17, 2000

Related U.S. Application Data

(63) Continuation of application No. 09/321,820, filed as application No. PCT/CA99/00718 on Aug. 5, 1999, now Pat. No. 6,504,149.
(60) Provisional application No. 60/095,481, filed on Aug. 5, 1998.

(51) Int. Cl.[7] ............................................. H01J 49/40
(52) U.S. Cl. ...................... 250/292; 250/290; 250/283; 250/286
(58) Field of Search ............................... 250/292, 293, 250/290, 283, 281, 282, 286

(56) References Cited

U.S. PATENT DOCUMENTS

| 3,668,383 A | 6/1972 | Carroll |
| 4,855,595 A | 8/1989 | Blanchard |
| 5,420,424 A | 5/1995 | Carnahan et al. |
| 5,723,861 A | 3/1998 | Carnahan et al. |
| 5,736,739 A | 4/1998 | Uber et al. |
| 5,789,745 A | 8/1998 | Martin et al. |
| 5,801,379 A | 9/1998 | Kouznetsov |
| 5,869,831 A | 2/1999 | De La Mora et al. |
| 5,905,258 A | 5/1999 | Clemmer et al. |
| 6,041,734 A | 3/2000 | Raoux et al. |
| 6,124,592 A | 9/2000 | Spangler |
| 6,162,709 A | 12/2000 | Raoux et al. |
| 6,323,482 B1 | 11/2001 | Clemmer et al. |
| 6,504,149 B2 * | 1/2003 | Guevremont et al. ........ 250/286 |

FOREIGN PATENT DOCUMENTS

| WO | WO 99/30350 A1 | 6/1999 |
| WO | WO 00/63949 A1 | 10/2000 |
| WO | WO 01/22049 A2 | 3/2001 |

OTHER PUBLICATIONS

Buryakov, I. A., Krylov, E. V., Nazarov, E. G., and Rasulev, U. K., A new method of separation of multi-atomic ions by mobility at atmospheric pressure using a high-frequency amplitude-asymmetric strong electric field, Int. J. Mass Spectrom. Ion Processes, 128, 143 (1993).

(List continued on next page.)

Primary Examiner—Kiet T. Nguyen
(74) Attorney, Agent, or Firm—Freedman & Associates

(57) ABSTRACT

The present invention provides an apparatus for selectively transmitting ions and trapping the ions within a defined 3-dimensional space at atmospheric pressure. The invention is based on the ion focussing principles of high field asymmetric wave-form ion mobility spectrometry in which an analyzer region is defined by a space between first and second spaced apart electrodes, the analyzer region having a gas inlet and a gas outlet for providing a flow of gas through the analyzer region. Ions which are introduced into the analyzer region are carried by a gas flow towards a gas outlet. At least one of the electrodes has a curved surface terminus located near the gas outlet and the gas flow is adjusted so that ions are trapped in a defined 3-dimensional space located near the tip of the terminus. Trapping of ions in a defined 3-dimensional space allows a more concentrated flow of desired ions.

48 Claims, 63 Drawing Sheets

OTHER PUBLICATIONS

Krylov, E. V., A method of reducing diffusion losses in a drift spectrometer, Tech. Phys., 44, 113 (1999).

Carnahan, B., Day, S., Kouznetsov, V., Matyjaszczyk, M., and Tarassov, A., Field Ion Spectrometry—A New Analytical Technology for Trace Gas Analysis, Proceedings of the 41st Annual ISA Analysis Division Symposium,, Framingham, MA, pp. 85 (1996).

Riegner, D. E., Harden, C. S., Carnahan, B., and Day, S., Qualitative Evaluation of Field Ion Spectrometry for Chemical Warfare Agent Detection, Proceedings of the 45th ASMS Conference on Mass Spectrometry and Allied Topics,, Palm Springs, California, pp. 473 (1997).

Spangler, G. E., Fundamental considerations for the application of miniature ion mobility spectrometry to field analytical applications, Field Analytical Chemistry and Technology, 4, 255 (2000).

Eiceman, G. A., Nazarov, E. G., Tadjikov, B., and Miller, R. A., Monitoring volatile organic compounds in ambient air inside and outside buildings with the use of a radio–frequency–based ion–mobility analyzer with a micromachined drift tube, Field Anal. Chem. Tech., 4, 297 (2000).

Miller, R. A., Eiceman, G. A., Nazarov, E. G., and King, A. T., A novel micromachined high–field asymmetric waveform–ion mobility spectrometer, Sensors Actuators B Chem, 67, 300 (2000).

Spangler, G. E., and Miller, R. A., Application of mobility theory to the interpretation of data generated by linear and RF excited ion mobility spectrometers, Int. J. Mass Spectrom., 214, 95–104 (2002).

Kiai, S. M. S., Confinement of ions in a radio frequency quadrople ion trap supplied with a periodic impulsional potential, Int. J. Mass Spectrom., 188, 177 (1999).

Kiai, S. M. S., Andre, J., Zerega, Y., Brincourt, G., and Catella, R., Study of a Quadrupole Ion Trap Supplied with a Periodic Impulsional Potential, Int. J Mass Spectrom. and Ion Processes, 107, 191 (1991).

Whetten, N. R., Macroscopic particle motion in quadrupole fields, J. Vac. Sci. Technol., 11, 515 (1974).

Buryakov, I. A., Kolomiets, Y. N., and Luppu, B. V., Detection of Explosive Vapors in the Air Using an Ion Drift Nonlinearity Spectrometer, J. Anal. Chem., 56, 336 (2001).

Krylov, E. V., Pulses of Special Shapes Formed on a Capacitive Load, Instruments and Experimental Techniques, 40, 628 (1997).

Wuerker, R. F., Shelton, H., and Langmuir, R. V., Electrodynamic Containment of Charged Particles, J. Appl. Phys., 30, 342 (1959).

Diedrich, F., Peik, E., Chen, J. M., Quint, W., and Walther, H., Observation of a Phase Transition of Stored Laser–Cooled Ions, Physical Review Letters, 59, 2931 (1987).

Baklanov, E. V., and Chebotayev, V. P., Resonant Light Absorption by the Ordered Structures of Ions Stored in a Trap, Appl. Phys. B, 39, 179 (1986).

Diedrich, F., and Walther, H., Nonclassical Radiation of a Single Stored Ion, Physical Review Letters, 58, 203 (1987).

Jungmann, K., Hoffnagle, J., DeVoe, R. G., and Brewer, R. G., Collective oscillations of stored ions, Physical Review A, 36, 3451 (1987).

* cited by examiner

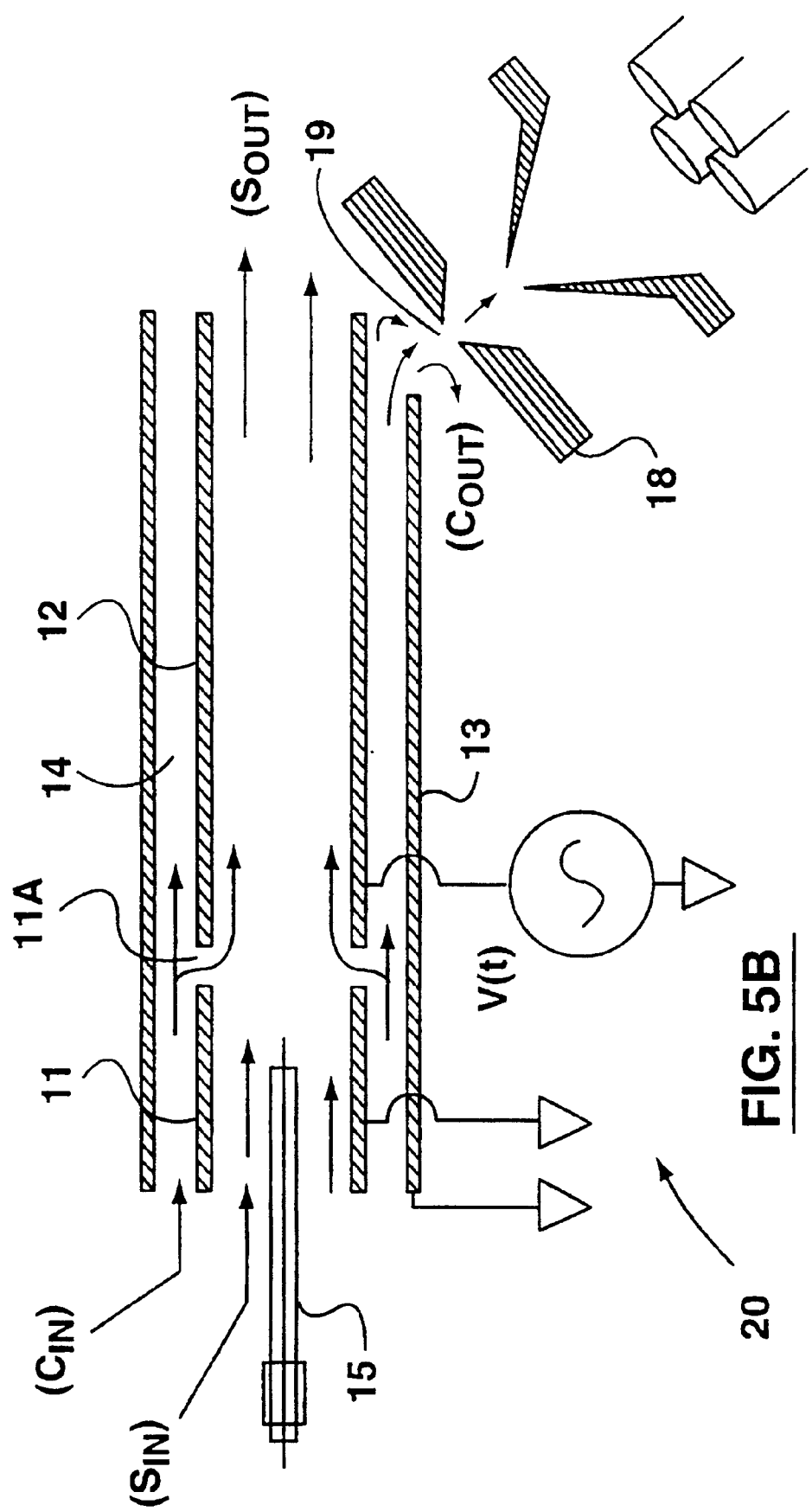

Timing Diagram for the Application of a High Frequency Asymmetric Waveform, a DC Voltage, and an Extraction Voltage The DV and CV Voltages are all applied to the center electrode.
The Extraction voltage is applied to the grid located in front of the center electrode.

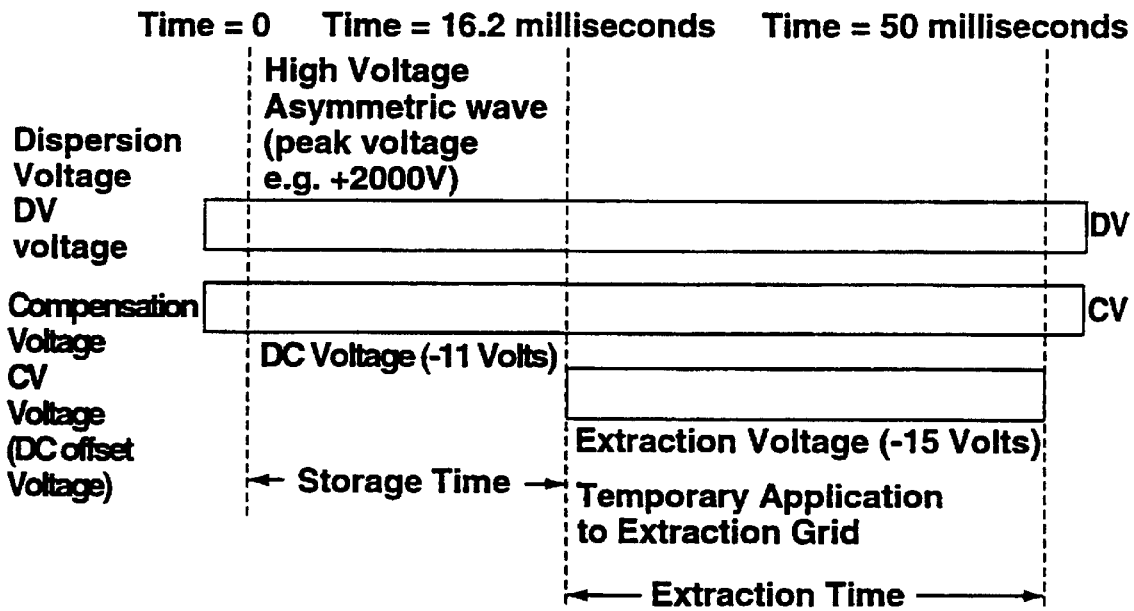

Details of the Asymmetric Waveform
(time and amplitude not to scale)

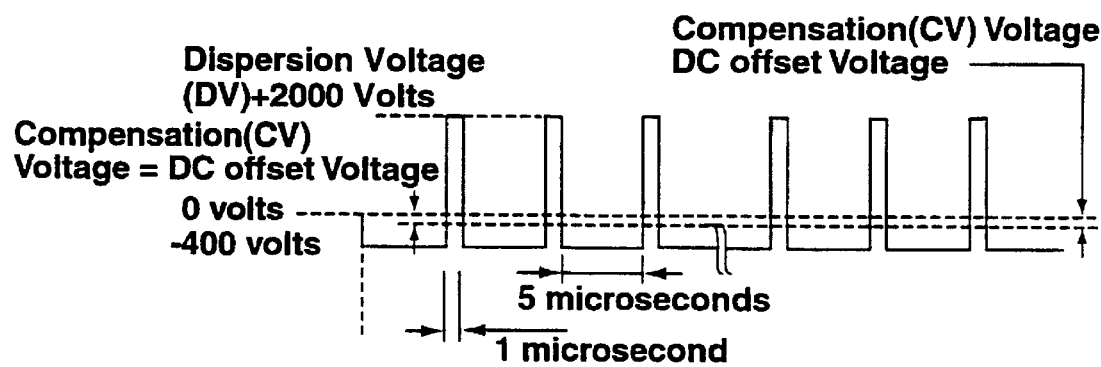

Detail of the Extraction Pulse
applied to the Extraction Grid

APPARATUS AND METHOD FOR ATMOSPHERIC PRESSURE-3-DIMENSIONAL ION TRAPPING

This application is a continuation of U.S. patent application Ser. No. 09/321,820 filed May 28, 1999 now issued as U.S. Pat. No. 6,504,149 on Jan. 7, 2003, which is the National Stage of International Application No. PCT/CA99/00718 filed Aug. 05, 1999, which claims the benefit of U.S. Provisional Application No. 60/095,481 filed Aug. 05, 1998.

FIELD OF THE INVENTION

The present invention relates to an apparatus and method for trapping ions, at atmospheric pressure, within a defined 3-dimensional space, based on the ion focussing principles of high field asymmetric waveform ion mobility spectrometry.

BACKGROUND OF THE INVENTION

High sensitivity and amenability to miniaturization for field-portable applications have helped to make ion mobility spectrometry an important technique for the detection of many compounds, including narcotics, explosives, and chemical warfare agents (see, for example, G. Eiceman and Z. Karpas, *Ion Mobility Spectrometry* (CRC. Boca Raton, Fla. 1994); and *Plasma Chromatography*, edited by T. W. Carr (Plenum, N.Y., 1984)). In ion mobility spectrometry, gas-phase ion mobilities are determined using a drift tube with a constant electric field. Ions are gated into the drift tube and are subsequently separated based upon differences in their drift velocity. The ion drift velocity is proportional to the electric field strength at low electric fields (e.g., 200 V/cm) and the mobility, K, which is determined from experimentation, is independent of the applied field. At high electric fields (e.g. 5000 or 10000 V/cm), the ion drift velocity may no longer be directly proportional to the applied field, and K becomes dependent upon the applied electric field (see G. Eiceman and Z. Karpas, *Ion Mobility Spectrometry* (CRC. Boca Raton, Fla. 1994); and E. A. Mason and E. W. McDaniel, *Transport Properties of Ions in Gases* (Wiley, N.Y., 1988)). At high electric fields, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry (see I. Buryakov, E. Krylov, E. Nazarov, and U. Rasulev, Int. J. Mass Spectrom. Ion Proc. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1–5, 1997, p. 473; B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85; and B. Carnahan and A. Tarassov, U.S. Pat. No. 5,420,424). Ions are separated in FAIMS on the basis of the difference in the mobility of an ion at high field $K_h$ relative to its mobility at low field K. That is, the ions are separated because of the compound dependent behaviour of $K_h$ as a function of the electric field. This offers a new tool for atmospheric pressure gas-phase ion studies since it is the change in ion mobility and not the absolute ion mobility that is being monitored.

One application of this tool as realized by the present inventors is in the area of ion trapping. To the inventors' knowledge, there are no previously known devices or methods that produce any sort of a 3-dimensional ion trap at atmospheric pressure (about 760 torr). While other 3-dimensional ion trapping mechanisms do exist, these known ion traps are typically designed to operate below 1 torr, in near-vacuum conditions. The efficiency of these ion traps degrades extremely rapidly as the pressure increases beyond 10 torr, and there is no experimental or theoretical basis to suggest that any trapping occurs, using these known methods, at 760 torr.

SUMMARY OF THE INVENTION

In one aspect, the present invention provides an apparatus for selectively transmitting ions and trapping said ions within a defined 3-dimensional space, comprising:
  a) at least one ionization source for producing ions;
  b) a high field asymmetric waveform ion mobility spectrometer, comprising an analyzer region defined by a space between at least first and second spaced apart electrodes for connection, in use, to an electrical controller capable of supplying an asymmetric waveform voltage and a direct-current compensation voltage for selectively transmitting a selected ion type in said analyzer region between said electrodes at a given combination of asymmetric waveform voltage and compensation voltage, said analyzer region having a gas inlet and a gas outlet for providing, in use, a flow of gas through said analyzer region, said analyzer region further having an ion inlet for introducing a flow of ions produced by said ionization source into said analyzer region; and
  c) a curved surface terminus provided on at least one of said electrodes, said terminus being a part of said one of said electrodes which part is closest to said gas outlet, said defined 3-dimensional space being located near said terminus, whereby, in use, said asymmetric waveform voltage, compensation voltage and gas flow are adjustable, so as to trap said transmitted ions within said 3-dimensional space.

Said first and second electrodes may comprise curved electrode bodies to provide a non-constant electric field therebetween, whereby, in use, said ions are selectively focussed in a focussing region created between said curved electrode bodies in said analyzer region.

In another embodiment, said first and second electrodes comprise outer and inner generally cylindrical coaxially aligned electrode bodies defining a generally annular space therebetween, said annular space forming said analyzer region, and said terminus being provided at an end of said inner cylindrical electrode body.

In another aspect, the present invention provides a method for selectively transmitting and trapping ions within a defined 3-dimensional space, said method comprising the steps of:
  a) providing at least one ionization source for producing ions;
  b) providing an analyzer region defined by a space between at least first and second spaced apart electrodes, said analyzer region being in communication with a gas inlet, a gas outlet and an ion inlet, said ions produced by said ionization source being introduced into said analyzer region at said ion inlet;
  c) providing an asymmetric waveform voltage and a direct-current compensation voltage, to at least one of said electrodes;
  d) adjusting said asymmetric waveform voltage and said compensation voltage to selectively transmit a type of ion within said analyzer region;

e) providing a curved surface terminus on at least one of said electrodes, said defined 3-dimensional space being located near said terminus; and f) providing a gas flow within said analyzer region flowing from said gas inlet to said gas outlet and adjusting said gas flow to trap said transmitted ions within and near said defined 3-dimensional space, said gas outlet being located near said terminus.

Advantageously, said analyzer region is operable substantially at atmospheric pressure and substantially at room temperature.

The method may further comprise the step of providing an ion outlet and supplying an extraction voltage at said ion outlet for extracting said trapped ions, said ion outlet being substantially aligned with said terminus and said defined 3-dimensional space.

In yet another aspect, the present invention provides an apparatus for selectively focussing ions and trapping said ions within a defined 3-dimensional space, comprising:

a) at least one ionization source for producing ions;

b) a segmented high field asymmetric waveform ion mobility spectrometer, comprising an analyzer region defined by spaces between a plurality of corresponding pairs of first and second spaced apart electrodes, for connection, in use, to an electrical controller capable of supplying an asymmetric waveform voltage, a direct current compensation voltage and a direct current segment offset voltage, each of said plurality of corresponding pairs of first and second spaced apart electrodes forming a segment and said segments being aligned in a row immediately adjacent to and electrically isolated from each other, said analyzer region having an ion inlet for introducing a flow of ions produced by said ionization source into said analyzer region. In yet another aspect, the present invention provides a method of selectively focussing ions and trapping said ions within a defined 3-dimensional space, comprising the steps of:

a) providing at least one ionization source for producing ions;

b) providing an analyzer region defined by spaces between a plurality of corresponding pairs of first and second spaced apart electrodes and providing a non-constant electric field between said first and second electrodes, each of said plurality of corresponding pairs of first and second spaced apart electrodes forming a segment and said segments being aligned in a row immediately adjacent to and electrically isolated from each other, said analyzer region being in communication with an ion inlet, and introducing said ions produced by said ionization source into said analyzer region at said ion inlet;

c) supplying an asymmetric waveform voltage to one of said first and second spaced apart electrodes in each of said segments;

d) supplying a direct current compensation voltage to said one of said first and second spaced apart electrodes in each of said segments, said direct current compensation voltages supplied to each of said segments being independently adjustable;

e) supplying a direct current segment offset voltage to another of said first and second spaced apart electrodes in each of said segments, said direct current segment offset voltages supplied to each of said segments being independently adjustable; and f) adjusting said direct current compensation voltages and said direct current segment offset voltages substantially equally, thereby providing a constant direct current potential across each corresponding pair of first and second electrodes in each of said segments, so as to focus desired ions between each corresponding pair of first and second electrodes in each of said segments at a given combination of said asymmetric voltage, direct current compensation voltage, and direct current segment offset voltage.

BRIEF DESCRIPTION OF THE DRAWINGS

For a better understanding of the present invention, and by way of example, reference will now be made to the accompanying drawings, which show preferred embodiments of the present invention in which:

FIGS. 5A and 5B show schematically the coupling of the FAIMS apparatus of FIGS. 3A and 3B together with a mass spectrometer;

FIG. 11D shows a timing diagram for a voltage applied to the FAIMS apparatus of FIGS. 11A–11C;

DETAILED DESCRIPTION OF THE INVENTION

As an important preliminary note, the discussion below uses the term "ion" to mean a charged atomic or molecular entity. The "ion" can be any electrically charged particle, solid or liquid, of any size. The discussion always refers to the "ion" as positively charged. However, all of the discussion in this document is equally applicable to negative ions, but with the polarity of applied voltages being reversed.

The principles of operation of FAIMS have been described in Buryakov et. al. (see I. Buryakov, E. Krylov, E. Nazarov, and U. Rasulev, Int. J. Mass Spectrom. Ion Proc. 128. 143 (1993)) and are summarized here briefly. The mobility of a given ion under the influence of an electric field can be expressed by: $K_h(E)=K(1+f(E))$, where $K_h$ is the mobility of an ion at high field, K is the coefficient of ion mobility at low electric field and "f(E)" describes the functional dependence of the ion mobility on the electric field (see E. A. Mason and E. W. McDaniel, *Transport Properties of Ions in Gases* (Wiley, N.Y., 1988); and I. Buryakov, E. Krylov, E. Nazarov, and U. Rasulev, Int. J. Mass Spectrom. Ion Proc. 128. 143 (1993)).

Figure 1:
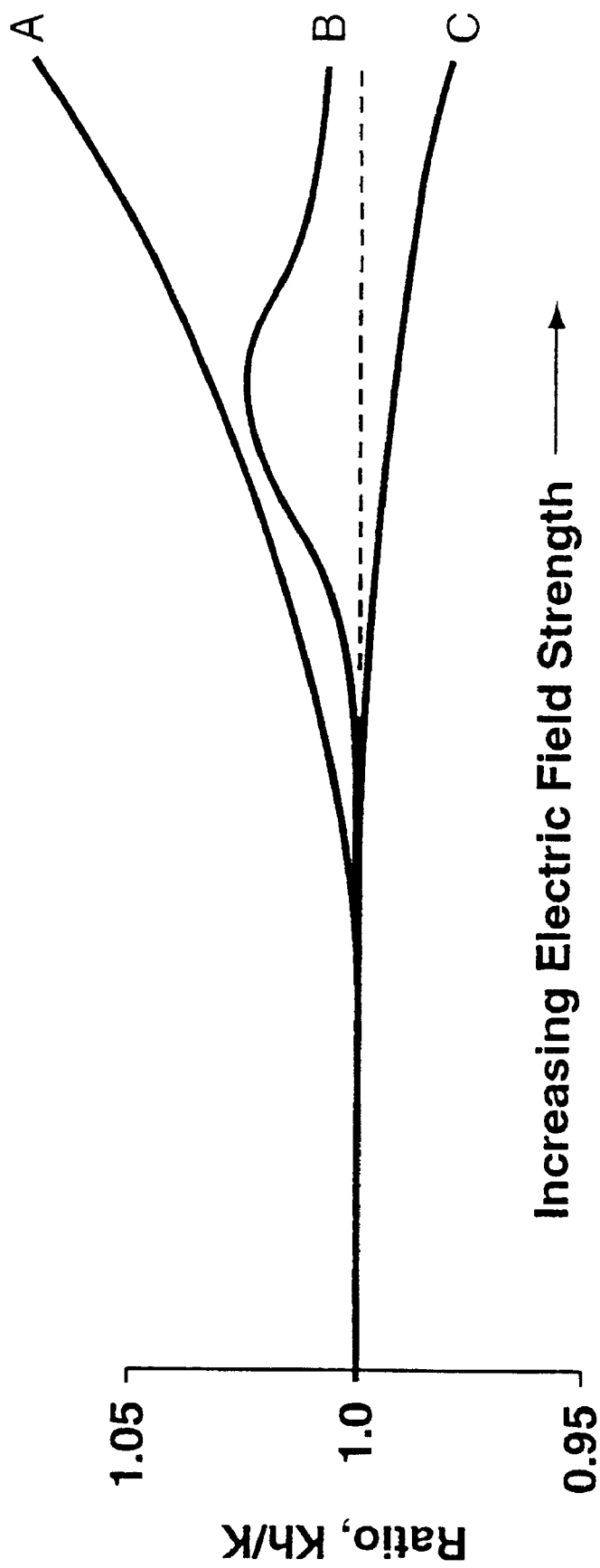
FIG. 1 shows three possible examples of changes in ion mobility as a function of the strength of an electric field.
Figure 2:
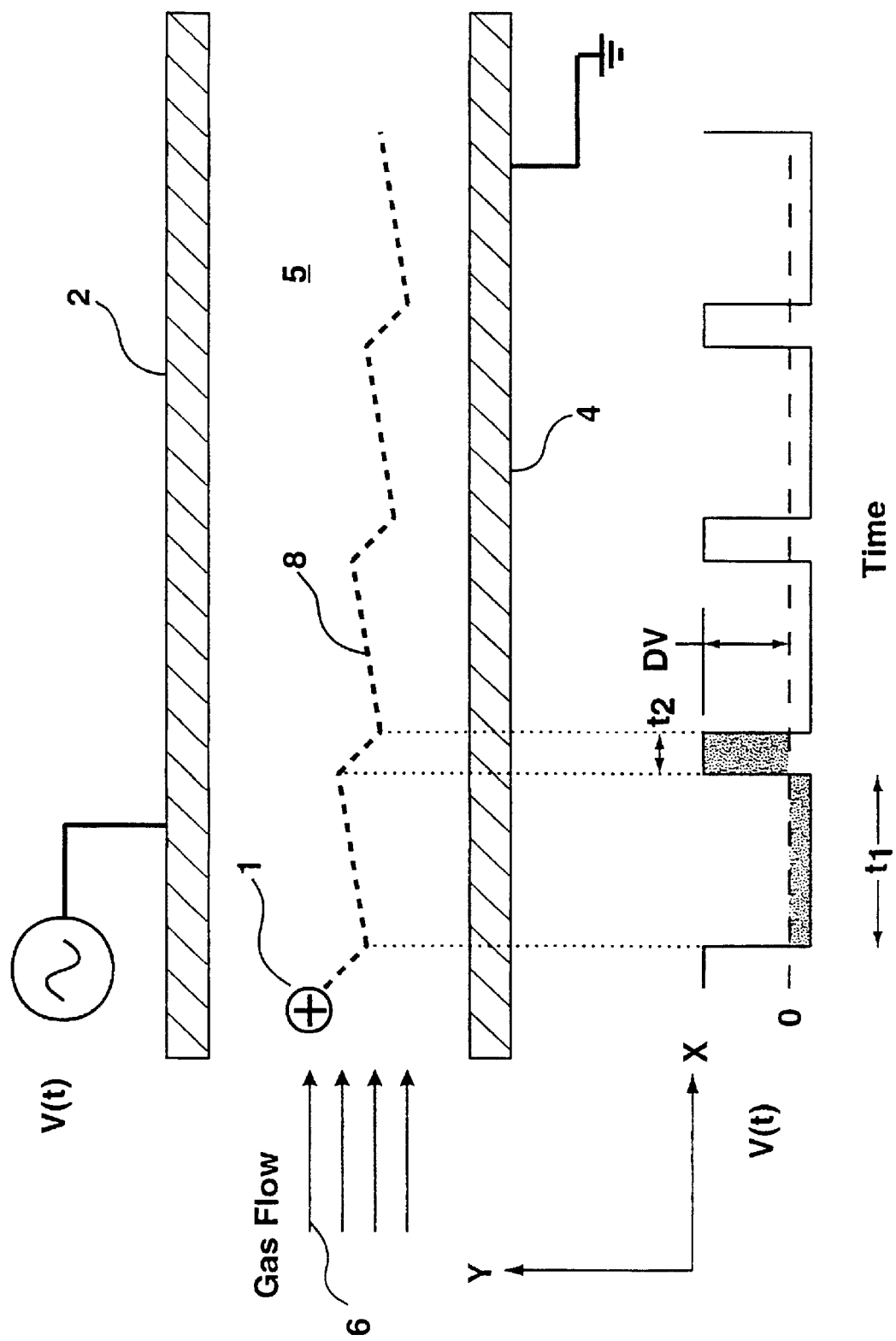
FIG. 2 illustrates the trajectory of an ion between two parallel plate electrodes under the influence of the electrical potential V(t)

Referring to FIG. 1, three examples of changes in ion mobility as a function of the strength of an electric field are shown: the mobility of type A ions increases with increasing electric field strength; the mobility of type C ions decreases; and the mobility of type B ions increases initially before decreasing at yet higher fields. The separation of ions in FAIMS is based upon these changes in mobility at high electric fields. Consider an ion 1, for example a type A ion shown in FIG. 1, that is being carried by a gas stream 6 between two spaced apart parallel plate electrodes 2, 4 as shown in FIG. 2. The space between the plates 2, 4 defines an analyzer region 5 in which the separation of ions may take place. The net motion of the ion 1 between the plates 2, 4 is the. sum of a horizontal x-axis component due to a flowing stream of gas 6 and a transverse y-axis component due to the electric field between the plates 2, 4. (The term "net" motion refers to the overall translation that the ion 1 experiences, even when this translational motion has a more rapid oscillation superimposed upon it.) One of the plates is maintained at ground potential (here, the lower plate 4) while the other (here, the upper plate 2) has an asymmetric waveform, V(t), applied to it. The asymmetric waveform V(t) is composed of a high voltage component, $V_1$, lasting for a short period of time $t_2$ and a lower voltage component, $V_2$, of opposite polarity, lasting a longer period of time $t_1$. The waveform is synthesized such that the integrated voltage-time product (thus the field-time product) applied to the plate during a complete cycle of the waveform is zero ( i.e., $V_1t_2+V_2t_1=0$); for example +2000 V for 10 $\mu$s followed by −1000 V for 20 $\mu$s. FIG. 2 illustrates the ion trajectory 8 (as a dashed line) for a portion of the waveform shown as V(t). The peak voltage during the shorter, high voltage portion of the waveform will be called the "dispersion voltage" or DV in this disclosure. During the high voltage portion of the waveform, the electric field will cause the ion 1 to move with a transverse velocity component $v_1=K_hE_{high}$, where $E_{high}$ is the applied field, and $K_h$ is the high field mobility under ambient electric field, pressure and temperature conditions. The distance travelled will be $d_1=v_1t_2=K_hE_{high}t_2$, where $t_2$ is the time period of the applied high voltage. During the longer duration, opposite polarity, low voltage portion of the waveform, the velocity component of the ion will be $v_2=KE_{low}$, where K is the low field ion mobility under ambient pressure and temperature conditions. The distance travelled is $d_2=v_2t_1=KE_{low}t_1$. Since the asymmetric waveform ensures that $(V_1t_2)+(V_2t_1)=0$, the field-time products $E_{high}t_2$ and $E_{low}t_1$ are equal in magnitude. Thus, if $K_h$ and K are identical, $d_1$ and $d_2$ are equal, and the ion 1 will be returned to its original position along the y-axis during the negative cycle of the waveform (as would be expected if both portions of the waveform were low voltage). If at $E_{high}$ the mobility $K_h>K$, the ion 1 will experience a net displacement from its original position relative to the y-axis. For example, positive ions of the type A shown in FIG. 1 will travel further during the positive portion of the waveform (i.e., $d_1>d_2$) and the type A ion 1 will migrate away from the upper plate 2 (as illustrated by the dashed line 8 in FIG. 2). Similarly, ions of type C will migrate towards the upper plate 2.

If an ion of type A is migrating away from the upper plate 2, a constant negative dc voltage can be applied to this plate 2 to reverse, or "compensate" for this transverse drift. This dc voltage, called the "compensation voltage" or CV in this disclosure, prevents the ion 1 from migrating towards either plate 2, 4. If ions derived from two compounds respond differently to the applied high electric fields, the ratio of $K_h$ to K may be different for each compound. Consequently, the magnitude of the compensation voltage CV necessary to prevent the drift of the ion toward either plate 2, 4 may also be different for each compound. Under conditions in which the compensation voltage CV is appropriate for transmission of one compound, the other will drift towards one of the plates 2, 4 and subsequently be lost. The speed at which the compound will move to the wall of the plates 2, 4 depends on the degree to which its high field mobility properties differ from those of the compound that will be allowed to pass under the selected condition. A FAIMS instrument or apparatus is an ion filter capable of selective transmission of only those ions with the appropriate ratio of $K_h$ to K.

The term FAIMS, as used in this disclosure, refers to any device which can separate ions via the above described mechanism, whether or not the device has focussing or trapping behaviour.

Improvements to FAIMS

The FAIMS concept was first shown by Buryakov et. al. using flat lates as described above. Later, Carnahan et. al. improved the sensor design by replacing the flat plates used to separate the ions with concentric cylinders (see B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85; U.S. Pat. No. 5,420,424 issued to Carnahan et al.). The concentric cylinder design has several advantages including higher sensitivity than the flat plate configuration (see R. W. Purves, R. Guevremont, S. Day, C. W. Pipich, and M. S. Matyjaszczyk, Rev. Sci. Instrum., 69, 4094 (1998)).

As mentioned earlier, an instrument based on the FAIMS concept has been built by Mine Safety Appliances Company (MSA). The MSA instrument uses the concentric cylinder design and is described further below. (For the purposes of this disclosure, the MSA instrument is referred to as FAIMS-E, where E refers to an electrometer or electric current detection device.)

One previous limitation of the cylindrical FAIMS technology (see D. Riegner, C. Harden, B. Carnahan, and S. Day, Proceedings of the 45th ASMS Conference on Mass Spectrometry and Allied Topics, Palm Springs, Calif., Jun. 1–5, 1997, p. 473; and B. Carnahan, S. Day, V. Kouznetsov, M. Matyjaszczyk, and A. Tarassov, Proceedings of the 41st ISA Analysis Division Symposium, Framingham, Mass., Apr. 21–24, 1996, p. 85) was that the identity of the peaks appearing in the FAIMS-E CV spectra could not be unambiguously confirmed due to the unpredictable changes in $K_h$ at high electric fields.

Thus, one way to extend the capability of instruments based on the FAIMS concept, such as the FAIMS-E instrument, is to provide a way to determine the make-up of the FAIMS-E CV spectra more accurately, for example, by introducing ions from the FAIMS-E device into a mass spectrometer for mass-to-charge (m/z) analysis.

Electrospray Ionization

ESI is one of several related techniques that involves the transfer of ions (which can be either positively or negatively charged) from liquid phase into the gas-phase. Kebarle has described four major processes that occur in electrospray ionization (intended for use in mass spectrometry): (1) production of charged droplets, (2) shrinkage of charged droplets by evaporation, (3) droplet disintegration (fission), and (4) formation of gas-phase ions (Kebarle, P. and Tang, L. Analytical Chemistry, 65 (1993) pp. 972A–986A). In ESI, a liquid solution (e.g. 50/50 w/w water/methanol) is passed through a metal capillary (e.g., 200 μm outer diameter and 100 μm ID) which is maintained at a high voltage to generate the charged droplets, say +2000 V (50 nA) for example. The liquid samples can be pumped through at, say, 1 μL/min. The high voltage creates a very strong, non-constant electric field at the exit end of the capillary, which nebulizes the liquid exiting from the capillary into small charged droplets and electrically charged ions by mechanisms described by Kebarle and many others. Several related methods also exist for creating gas-phase ions from solution phase. Some examples of these methods include ionspray, which uses mechanical energy from a high velocity gas to assist in nebulization; thermospray, which applies heat instead of a voltage to the capillary; and nanospray, which uses small ID capillaries. In this disclosure, the term ESI is used to encompass any technique that creates gas-phase ions from solution.

Modified FAIMS-E

As a first step, the FAIMS-E device designed and built by Mine Safety Appliances Company was modified to permit the introduction of ions using ESI. The inventors believe that the coupling of an ESI source together with a FAIMS-E device is not obvious as it is known that ions produced by ESI have a high degree of solvation, and that a FAIMS-E device may not function properly when exposed to high levels of solvent vapour. The inventors have developed various practical embodiments of an apparatus that combines an ESI source together with a FAIMS device to show that such coupling is possible.

Figure 3A:
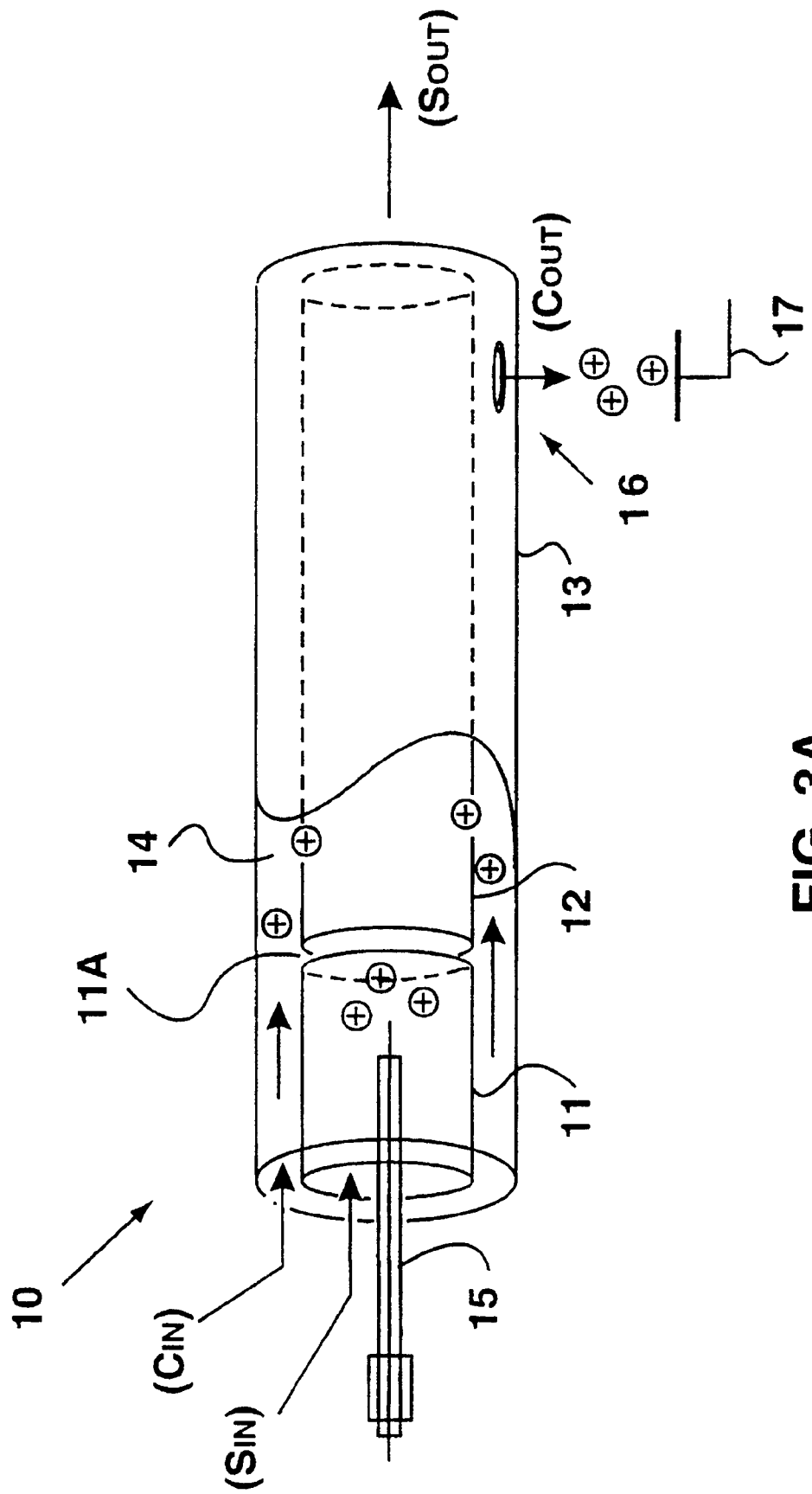
FIGS. 3A and 3B show schematically an embodiment of a modified FAIMS device.
Figure 3B:
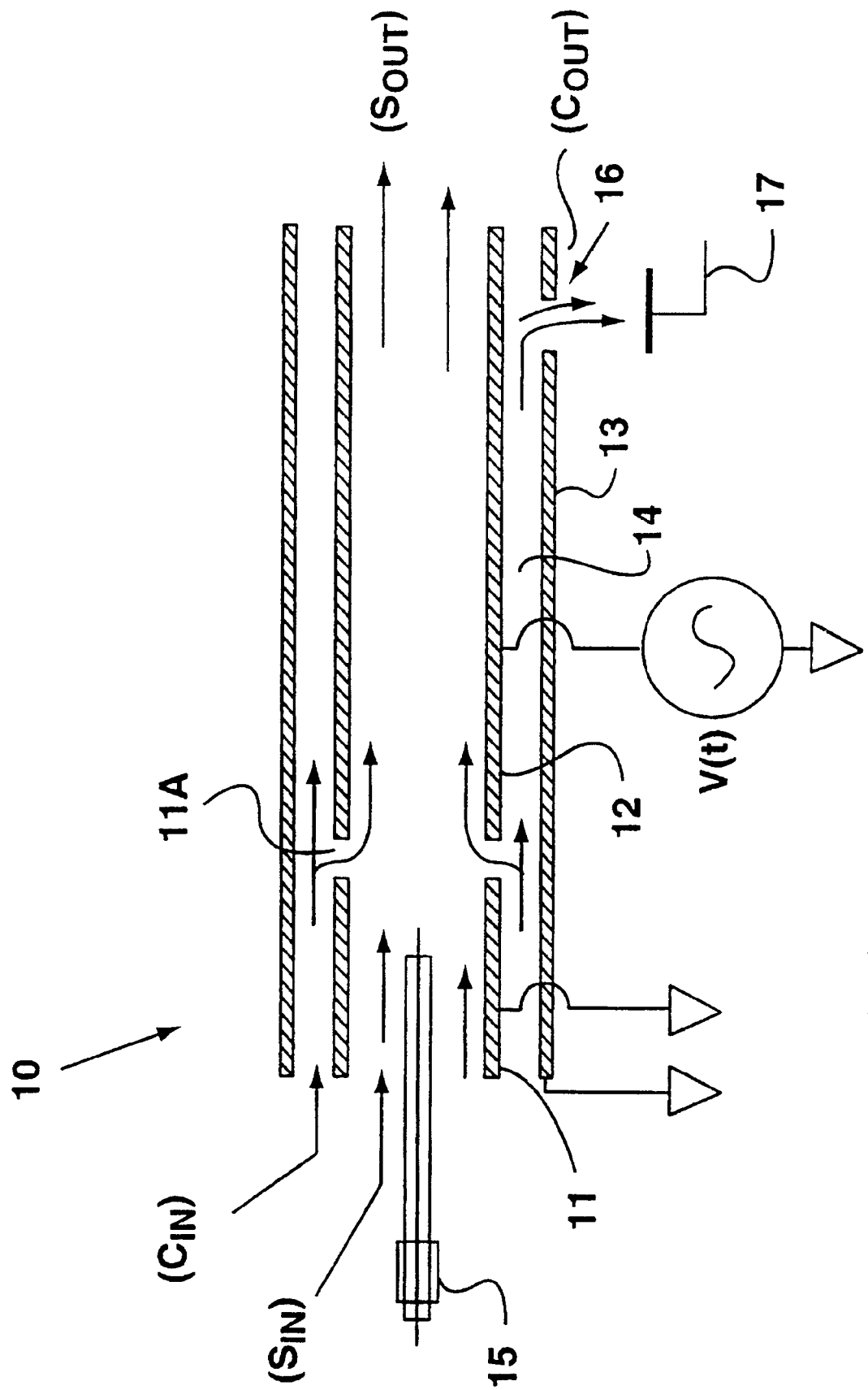

One example is the modified FAIMS-E device 10 shown schematically in 3-dimensional view in FIG. 3A and in cross section in FIG. 3B. The FAIMS-E apparatus 10 is composed of two short inner cylinders or tubes 11, 12 which are axially aligned and positioned about 5 mm apart, and a long outer cylinder 13 which surrounds the two inner cylinders 11, 12. The inner cylinders 11, 12 (12 mm inner diameter, 14 mm outer diameter), are about 30 mm and 90 mm long, respectively, while the outer cylinder 13 (18 mm inner diameter, 20 mm outer diameter) is about 125 mm long. Ion separation takes place in the 2 mm annular space of FAIMS analyzer region 14 between the long inner cylinder 12 and the outer cylinder 13. To produce ions using electrospray ionization (ESI), for introduction into the FAIMS analyzer region 14 of the FAIMS device, the metal capillary of the ESI needle 15 was placed along the central axis of the shorter inner cylinder 11, terminating about 5 mm short of the gap or ion inlet between the two inner cylinders 11, 12. The positioning of the ESI needle 15 shown in FIGS. 3(A) and 3(B) differs from the positioning of the ionization source found in the MSA FAIMS-E device in that the ESI needle 15 does not extend through the long inner cylinder 12 to which the asymmetric waveform V(t) is typically applied. By introducing the ESI needle 15 from the opposite end of the FAIMS-E, i.e. through the short inner cylinder 11, and not positioning the tip of the ESI needle 15 too close to the long inner cylinder 12, the performance of the ESI needle 15 is not compromised by the asymmetric waveform V(t), which would be the case if the ESI needle 15 was positioned within the long inner cylinder 12 (as disclosed in U.S. Pat. No. 5,420,424).

As explained above, the FAIMS-E device 10 can be considered as an ion "filter", with the capability of selectively transmitting one type of ion out of a mixture. If a mixture of ions is presented continuously to the entrance of the FAIMS analyzer region 14, for example by an ESI needle 15, and the ions are carried along the length of the analyzer 14 by a flowing gas under conditions in which no voltages are applied to either the inner cylinder 12 or outer cylinder 13 (i.e. the electrodes are grounded), some finite level of transmission for every ion is expected, albeit without any separation.

It might be expected that the detected current of any selected ion in this mixture should never exceed the current for that ion when it is transmitted through the device 10 in the no-voltages condition. It might also be expected that application of high voltages (i.e. application of transverse fields, perpendicular to the gas flows) designed to yield ion separation should not increase the ion transmission, but should decrease transmission through collisions with the walls of the cylinders 12, 13. That is, the asymmetric waveform might effectively narrow the "width" of the FAIMS analyzer region 14, and therefore should decrease the ion transmission. However, contrary to this prediction, experiments conducted by the inventors and described in this disclosure have shown that the sensitivity of ion detection in the cylindrical geometry FAIMS-E 10 increases as the voltage amplitude of the asymmetric waveform V(t) is increased. As will be explained below, these unusual observations suggest that atmospheric pressure ion focussing is occurring in the FAIMS analyzer region 14.

Still referring to FIGS. 3A and 3B, four gas connections to the FAIMS-E apparatus 10 are shown. Compressed gas (e.g. air or nitrogen) is passed through a charcoal/molecular sieve gas purification cylinder (not shown) into the FAIMS-E 10 through carrier in ($C_{in}$) and/or sample in ($S_{in}$) ports. The gas exits the FAIMS-E 10 via the carrier out ($C_{out}$) and/or sample out ($S_{out}$) ports. All four gas flow rates can be adjusted. Non-volatile analytes are typically introduced into the FAIMS-E 10 using an ESI needle 15. Alternatively, volatile analytes may be introduced into the FAIMS-E 10 through the $S_{in}$ line, and a portion may be ionized as the compound(s) pass by a corona discharge needle.

Still referring to FIGS. 3A and 3B, the outer cylinder 13 of the FAIMS-E apparatus 10, and the shorter inner cylinder 11, are typically held at an adjustable electrical potential ($V_{FAIMS}$). $V_{FAIMS}$ is usually ground potential in FAIMS-E. During operation, a high frequency high voltage asymmetric waveform is applied to the long inner cylinder 12 to establish the electric fields between the inner and outer cylinders 12, 13. In addition to this high frequency (e.g., 210 kHz) high voltage waveform a dc offset voltage (i.e. the compensation voltage CV added to FAIMS) is applied to the long inner cylinder 12. This leads to the separation of ions in the FAIMS analyzer region 14 in the manner discussed earlier.

Still referring to FIGS. 3A and 3B, some of the ions produced by the ionization source are carried by the gas stream along the length of the annular space between the outer cylinder 13 and the long inner cylinder 12, also referred to as the FAIMS analyzer region 14. If the combination of DV and CV are appropriate, and the ion is not lost to the tube walls, a series of openings or ion outlets 16 near the downstream end of the outer cylinder 13 allow the ions to be extracted to an electrical current detector 17 which is biased to about −100 V. (Note that here the carrier gas also exits from the ion outlet 16.)

Figure 4:
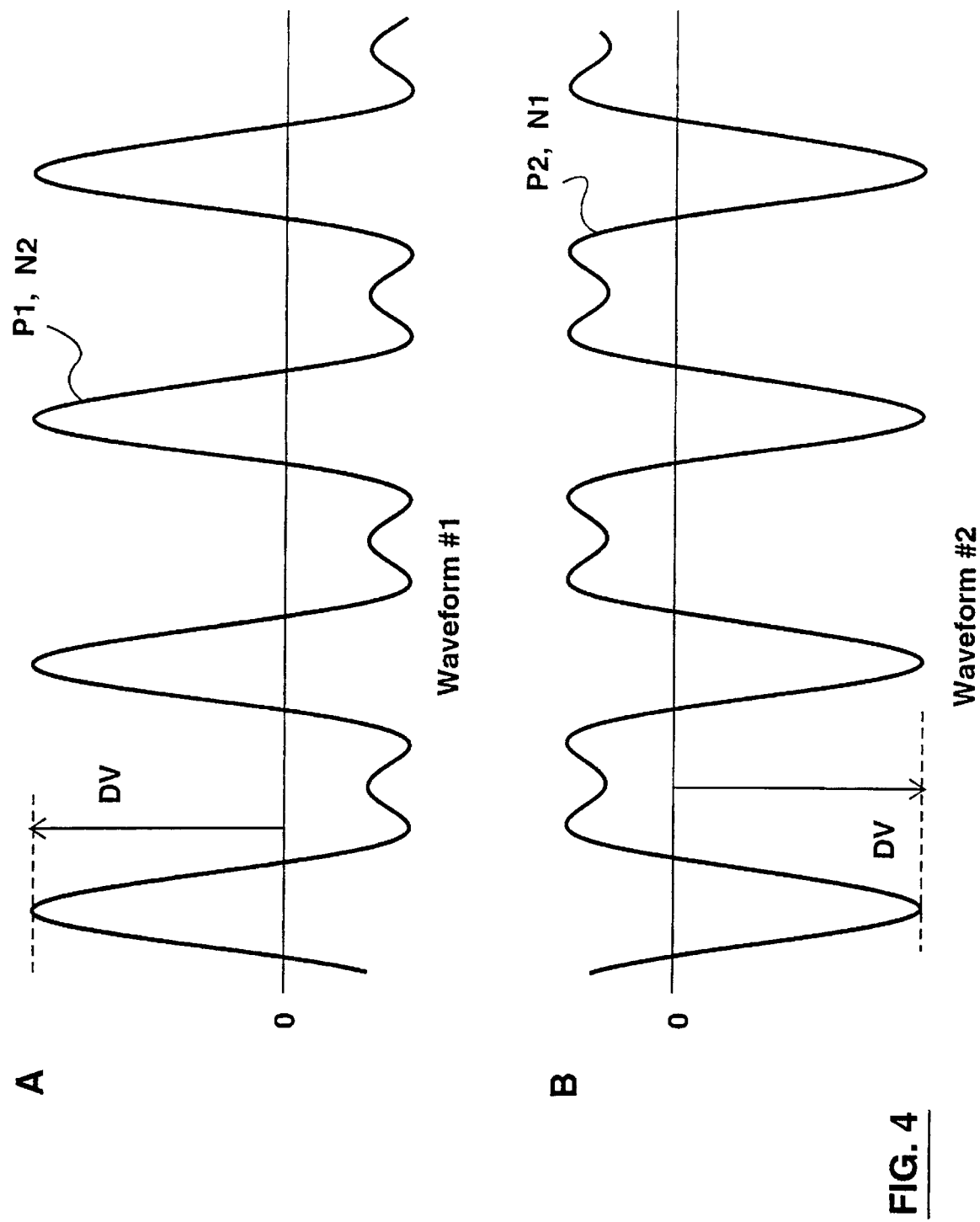
FIG. 4 illustrates two opposite waveform modes which may be used with the apparatus of FIGS. 3A and 3B.

In practice, the simplified square wave version of V(t) shown in FIG. 2 cannot be used because of the electrical power demands that such a wave would place on the waveform generator. The actual waveforms V(t) appear in FIG. 4. These waveforms are produced by the electronic addition of a sine wave and its harmonic of twice the frequency. As shown in FIG. 4, the FAIMS-E apparatus 10 operates using one of the two waveform modes (with the waveform applied to the inner cylinder). These reversed polarity waveform modes do not yield "reversed polarity" CV spectra as might be expected. This is because the reversal of polarity in this manner also creates a mirror image effect of the ion focussing behaviour of FAIMS. The result of such polarity reversal is that the ions are not focussed, but rather collide with the walls of the cylinders 12, 13. The mirror image of a focussing valley is a hill-shaped potential surface. (This characteristic, and the various "modes" of operation of FAIMS, is discussed further below.)

FAIMS-MS

As discussed earlier, one way to extend the functionality of FAIMS devices is to couple them together with a mass spectrometer. The use of a mass spectrometer together with a FAIMS device is advantageous because the mass spectrometer facilitates a mass-to-charge (m/z) analysis to determine the make-up of CV spectra more accurately. One possible FAIMS-MS embodiment is described here.

Figure 5A:
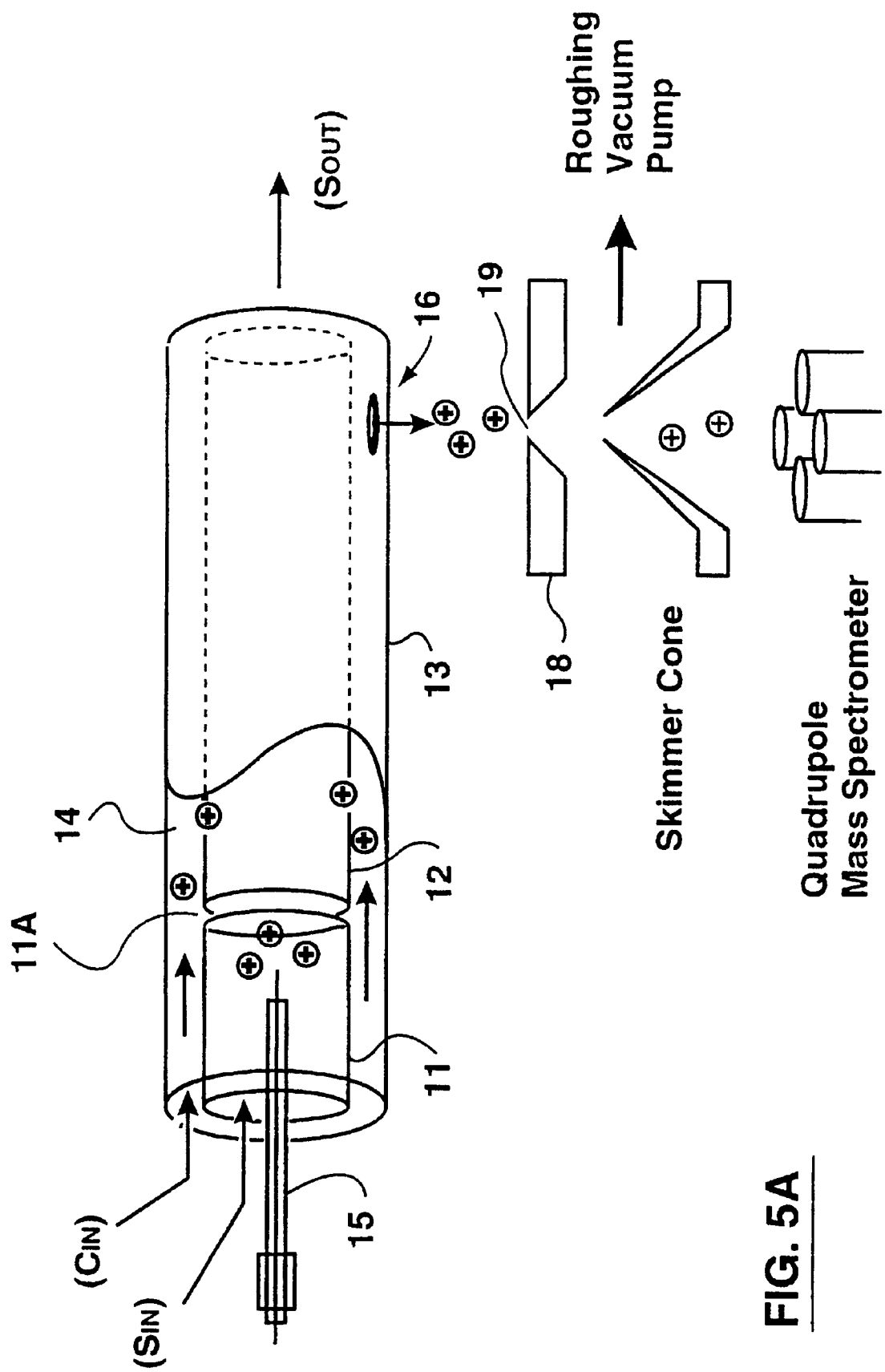

Referring to FIGS. 5A and 5B, the coupling of FAIMS and a mass spectrometer (FAIMS-MS 20) is shown schematically. The FAIMS-MS 20 of FIGS. 5A and 5B, and the FAIMS-E 10 shown in FIGS. 3A and 3B, differ significantly only at the detection end of the instrument. In accordance with the invention, the electrometer 17 has been replaced by a sampler cone 18, placed at the end of the FAIMS cylinders 12, 13 as is shown in a simplified form in FIG. 5B. The diameter of the orifice 19 in the sampler cone 18 is approximately 250 $\mu$m. The gas flows in the FAIMS-MS 20 are analogous to those in the FAIMS-E 10 except that the $C_{out}$ is divided into two components, namely the original $C_{out}$ and the flow through the orifice 19 into the mass spectrometer. The electrical waveforms applied to the long inner cylinder 12 are identical to those used in the FAIMS-E apparatus 10. The sampler cone 18 may be electrically insulated from the other components so a separate voltage OR can be applied to it. Furthermore, a voltage can be applied to the cylinders of the entire FAIMS unit ($V_{FAIMS}$) for the purpose of enhancing the sensitivity of the FAIMS-MS.

FIG. 5B shows the FAIMS cylinders 12, 13 at a 45 degree angle in relation to the sampler cone 18 of the mass spectrometer. FIG. 5A showed the FAIMS cylinders 12, 13 at a 90 degree angle in relation to the sampler cone 18. The way (i.e., the angle between the two tubes of the FAIMS and the sampler cone 18) in which the ions are extracted from the cylinders 12, 13 of the FAIMS-MS 20 into the mass spectrometer is not limited to these angles. Furthermore, the location in which the ions are extracted from the two tubes can also be changed. That is, the ions can be extracted anywhere along the separation region of the FAIMS.

Ion Focussing/FAIMS-R1-prototype

Figure 6A:
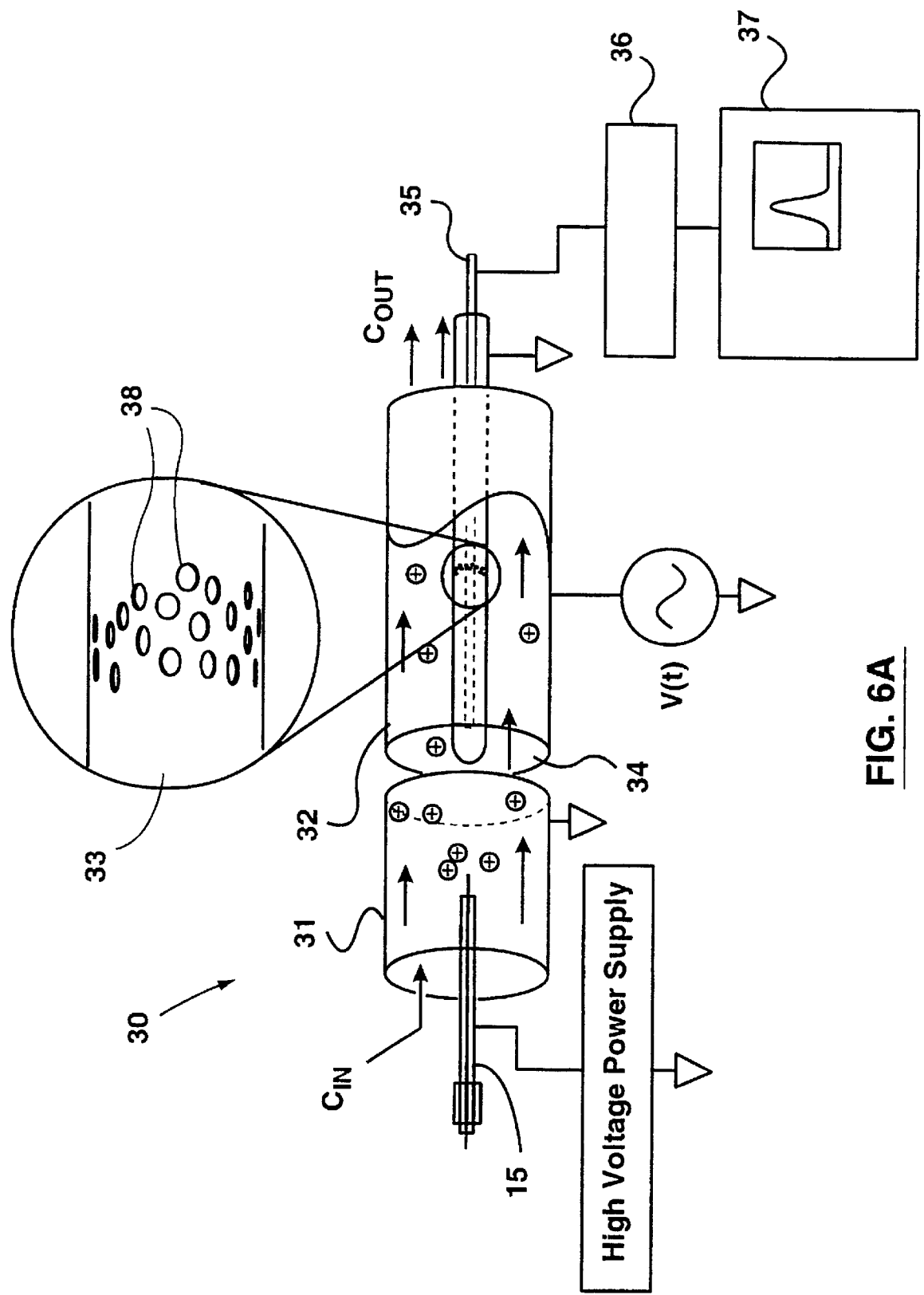
FIGS. 6A and 6B shows schematically a FAIMS apparatus for measuring the ion distribution in the analyzer region.
Figure 6B:
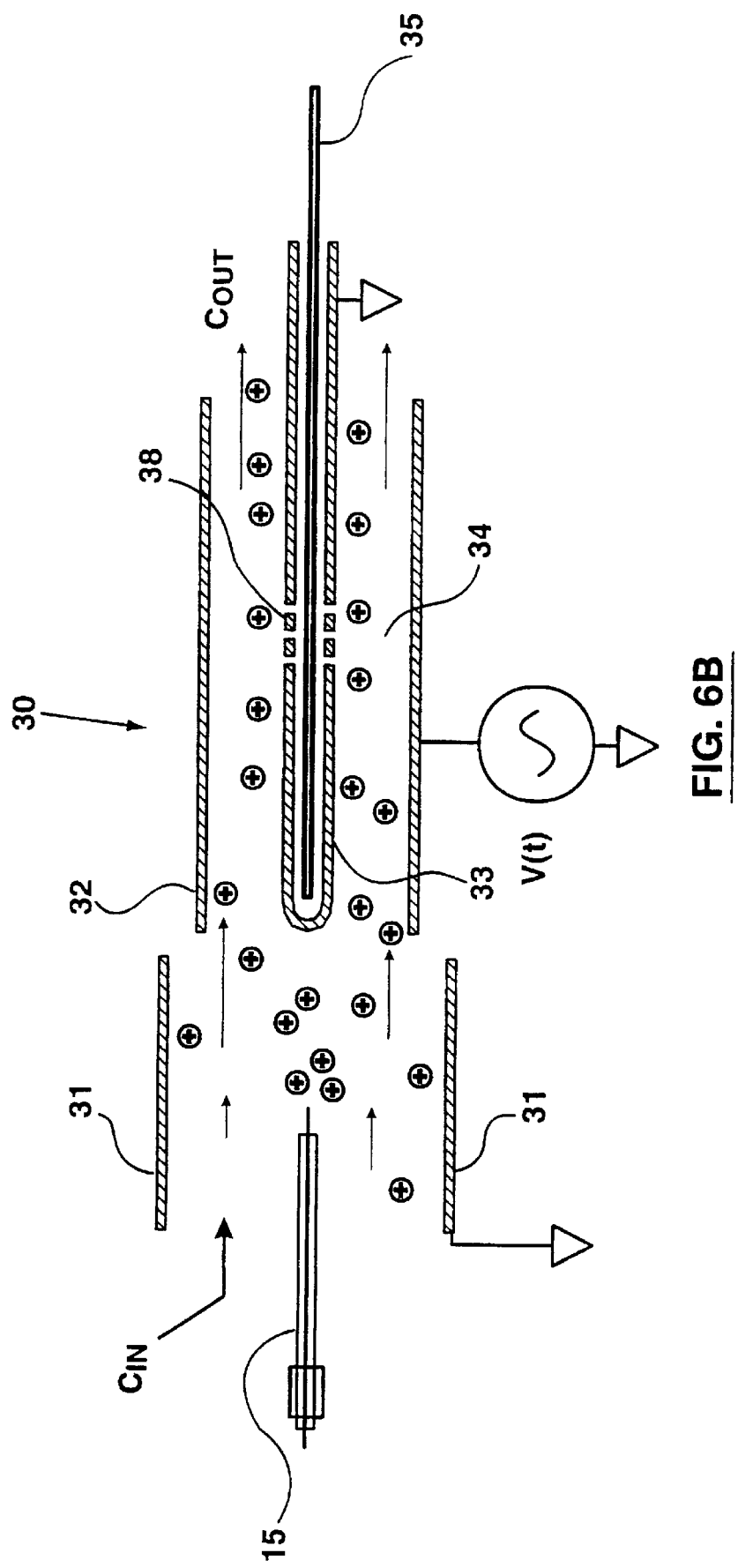

Referring now to FIGS. 6A and 6B, to demonstrate the focussing effect referred to above, a special FAIMS instrument was designed by the inventors and constructed to measure the ion distribution between the two cylinders (outer and inner cylinders) of a FAIMS device. This instrument will be referred to in this disclosure as the FAIMS-R1-prototype 30 and is illustrated schematically in FIGS. 6A and 6B. Ions were generated inside of an electrically grounded cylinder 31 approximately 35 mm long and 20 mm i.d.. The tip of an ionization needle 15 was typically located near the center of this tube, and at least 15 mm from the end of the FAIMS analyzer region 34. The FAIMS analyzer region 34 in this embodiment is composed of an outer tube 32 which is 70 mm long and 6 mm i.d., and which surrounds a 2 mm o.d. inner shield electrode 33. The inner shield electrode 33 is an electrically grounded stainless steel tube which is closed at the end that faces the ionization needle 15.

This inner electrode 33 surrounds, and shields, an electrically isolated conductor 35 passing into its center. This innermost conductor 35 (i.e the ion collector electrode) is a collector for ions, and is connected to a fast current amplifier or electrometer 36 (e.g. Keithly model 428) and a digital storage oscilloscope 37 (e.g. LeCroy model 9450).

In the system shown in FIGS. 6A and 6B, the ions which surround the inner electrode 33 are forced inwards by a pulsed voltage. These ions travel from the FAIMS analyzer region 34 to the innermost conductor 35 through a series of 50 μm holes 38 drilled through the inner shield electrode 33. The holes drilled in the inner shield electrode 33 are positioned about 2 cm from the end facing the ionization needle 15, and are spaced about 0.5 mm apart for a distance of 10 mm on one side of the inner shield electrode 33. The holes 38 drilled in the inner shield electrode 33 are located in this manner to minimize the variability in distance between the inner shield electrode 33 and the outer cylinder 32 in the vicinity of these holes 38. It was the inventors' objective to measure the ion abundance radial profiles of the ions located in the annular space (i.e. the FAIMS analyzer region 34) between the inner shield electrode 33 and the outer electrode 32 by pulsing the ions toward the inner shield electrode 33 and through the holes 38 and against the innermost ion collector electrode 35. The time-dependent distribution of ions arriving at the innermost conductor 35 is related to the physical radial distribution of ions around the inner electrode 33. Excessive variation in the distance between the two cylinders 32, 33 would have increased the uncertainty of the ion arrival times at the innermost conductor 35, thus decreasing the spatial resolution of the measurements made with this device.

Figure 7:
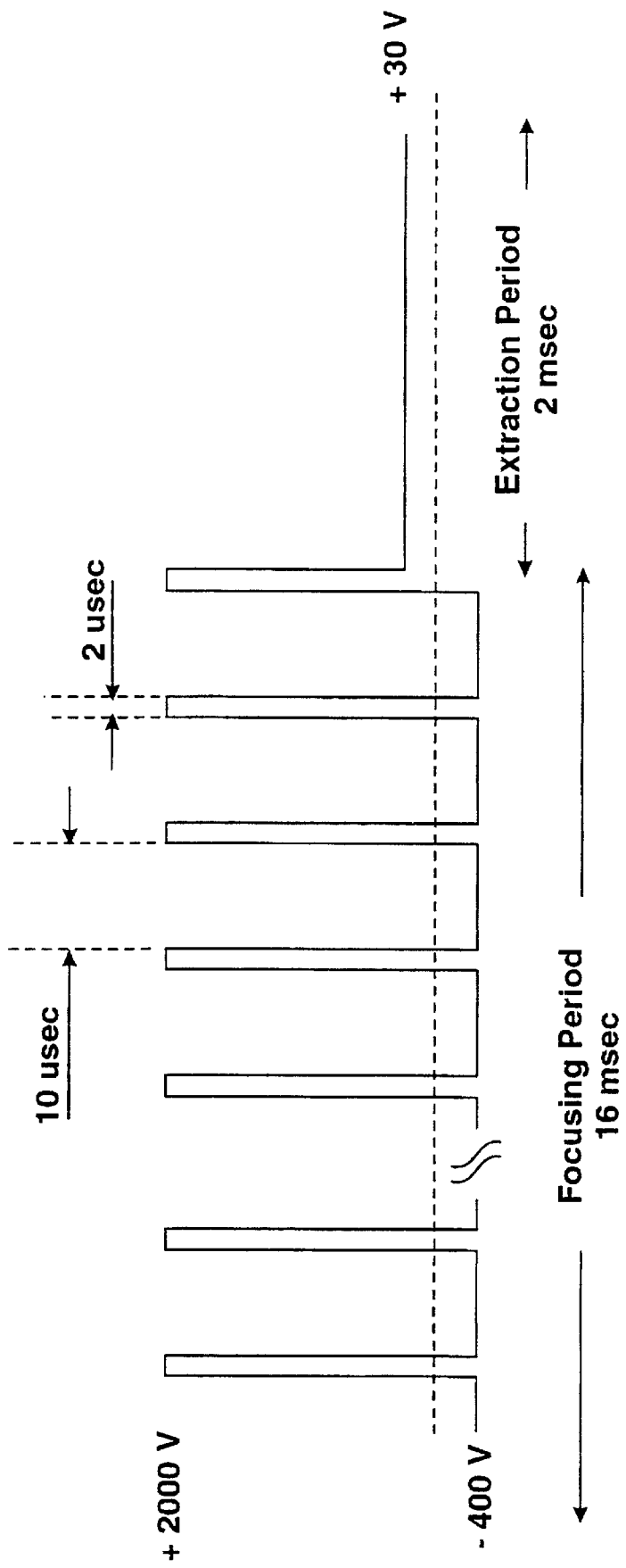
FIGS. 7 illustrates the high voltage, high frequency asymmetric waveform applied to the FAIMS apparatus shown in FIGS. 6A and 6B.

Now referring to FIG. 7, the high voltage, high frequency asymmetric waveform V(t), applied to the FAIMS-R1-prototype of FIGS. 6A and 6B, is shown. The waveform is divided into two parts, the focussing period and the extraction period. The waveform was synthesized by an arbitrary waveform generator (e.g. Stanford Research Systems model DS340, not shown) and amplified by a pulse generator (e.g. Directed Energy Inc., model GRX-3.0K-H, not shown). The frequency of the waveform, and the relative duration of the high and low voltage portions of the waveform could easily be modified. Because of the high voltages, and steep rise-times of the square waves applied to this FAIMS-R1-prototype 30, the power consumption limits were severe, and waveforms in excess of about 1330 pulses (16 ms at 83,000 Hz) could not be delivered by this system without overheating electronic components of the high voltage pulse generator.

Note that, in the case of the FAIMS-R1-prototype 30, the high voltage, high frequency asymmetric waveform was applied to the outer cylinder 32 of the FAIMS-R1-prototype 30 shown in FIGS. 6A and 6B. Since all other forms of FAIMS discussed in this disclosure have the waveform applied to the inner tube or electrode, confusion may arise from the "polarity" of the waveform and the polarity of CV. In the FAIMS-R1-prototype 30 shown in FIGS. 6A and 6B, ions of type A (shown in FIG. 1) are focussed during application of the opposite polarity waveform and CV than that shown for the devices in FIGS. 3A, 3B, 5A and 5B. Nevertheless, for simplification, the polarity will be written to be the same as if the device was constructed in the same way as those of the more conventional configuration. In other words the ions transmitted during application of waveform #1 will appear with DV positive and with CV negative. (Please note, however, that the actual voltages used on the device in FIGS. 6A and 6B are DV negative and CV positive).

As was observed in the conventional parallel plate FAIMS apparatus described earlier (FIG. 2), the application of a high voltage asymmetric waveform V(t) will cause ions to migrate towards one of the FAIMS electrodes 2, 4 because of the changes in ion mobility at high electric fields (shown in FIGS. 1 and 2). This migration can be stopped by applying an electric field or compensation voltage CV in a direction to oppose the migration. For the FAIMS-R1-prototype 30 of FIGS. 6A and 6B, this CV was applied to the same electrode as the high voltage asymmetric waveform (i.e. the outer electrode 32), and was added to the waveform as a small dc bias (up to ±50 V). At an appropriate combination of DV, and compensation voltage CV, a given ion will pass through the FAIMS device 30. The unit therefore acts like an ion filter. It is possible to fix conditions such that a single type of ion is isolated in the FAIMS analyzer 34 although a mixture flows uniformly out of the exit of the FAIMS device 30 although a mixture of ions are presented to the inlet of the FAIMS analyzer region 34.

The second part of the waveform shown in FIG. 7 (i.e. the extraction period) was used to pulse the ions out of the FAIMS analyzer region 34 between the outer electrode 32, and the inner shield electrode 33 (shown in FIGS. 6A and 6B). At the end of the focussing period, i.e. after 16 ms of waveform, the asymmetric waveform was replaced by a constant dc bias of approximately +30 V. This caused the ions from the annular space 34 between the outer electrode 32 and the inner shield electrode 33 to move in the direction of the inner shield electrode 33. A detector bias of –5 V, applied to innermost ion collector electrode 35, helped to carry the ions from the vicinity of the holes 38 in the inner shield electrode 33, through the holes 38 and into contact with the innermost ion collector electrode 35. The +30 V bias created an electric field of approximately 150 V/cm across the FAIMS analyzer region 34 and most ions located within this region 34 travelled across the 2 mm space in about 1 ms. The ion current due to the arrival of ions at the center inner shield electrode 33 can be predicted. For example, if only one type of ion, with mobility of 2.3 $cm^2$/V-s, e.g., $(H_2O)_nH^+$ at ambient temperature and pressure conditions, was located in the FAIMS analyzer region 34, and if this ion was distributed evenly in the space, an approximately square-topped signal lasting approximately 0.6 ms should be observed. Deviation from this expected ion arrival profile would suggest that the ions were distributed in non-uniform profile across the FAIMS analyzer region 34 between the outer and inner cylinders of the FAIMS device 30.

Still referring to FIGS. 6A, 6B, and 7, the FAIMS-R1-prototype 30 was operated as follows. A 2 L/min flow of purified air, Carrier Gas In (Cin), was passed into the cylinder 31 housing the ionization needle 15. Approximately 2000 V was applied to the needle 15, and the voltage was adjusted to produce a stable ionization current. The high voltage asymmetric waveform V(t) was applied to the outer FAIMS cylinder 32 for approximately 16 ms; this was followed by a 2 ms extraction pulse (FIG. 7). The ion current striking the innermost ion collecting electrode 35 was detected and displayed on a digital oscilloscope 37. A measurement would typically consist of 100 averaged spectra, collected at a rate of approximately 5 Hz. Many experimental parameters were varied, including gas flow rates, the voltages of the asymmetric waveform V(t), the dc voltage applied to the outer electrode CV, and the extraction voltage.

Figure 8:
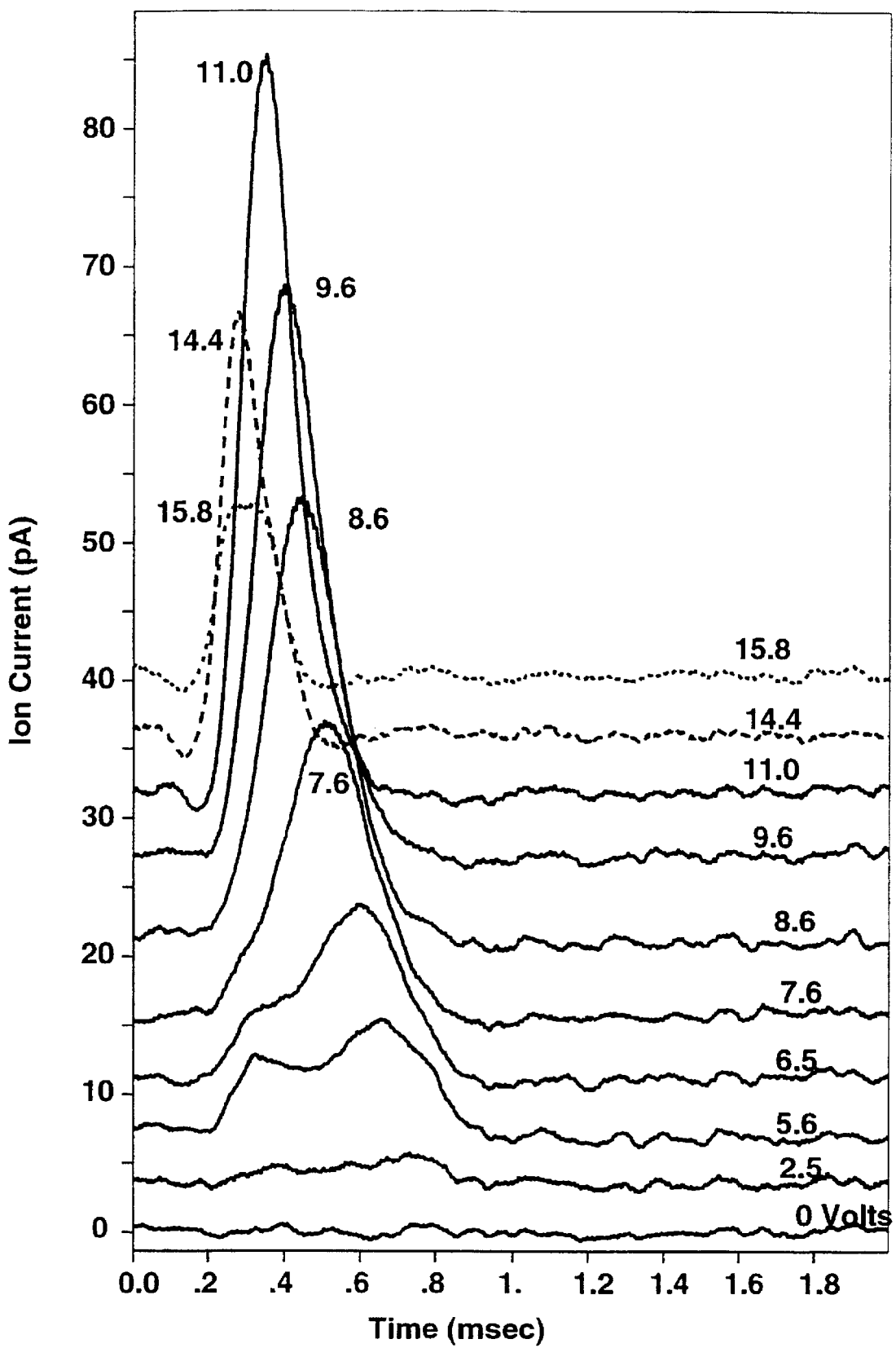
FIG. 8 illustrates varying ion arrival time profiles at the innermost ion collector electrode of the FAIMS apparatus in FIGS. 6A and 6B.

FIG. 8 illustrates the ion arrival times at the innermost ion collector electrode 35 observed by conducting these experiments. Each trace was recorded with 2500 V applied DV, but with variable CV voltages. As can be seen, during application of DV and CV, the radial distribution of ions is not uniform across the annular space of the FAIMS analyzer region 34. For example, at CV near −11 V, the ions are focussed into a narrow band near the inner electrode 33, and therefore are detected as a high intensity pulse occurring very early after the extraction voltage has been applied. At low CV, for example at −5.6 V, the ions are much more uniformly distributed between the walls of the concentric cylinders 32 33 making up the FAIMS analyzer region 34. When no electrical voltages are applied to the cylinders 32, 33, the radial distribution of ions should be approximately uniform across the FAIMS analyzer region 34 (data for this no-voltage experimental condition is not shown in this document). The experimental data shown in FIG. 8 is evidence that the ion focussing is indeed occurring in FAIMS instruments. This focussing results in the ions being focussed in a uniform "sheet" or band around the inner cylinder 33 within the FAIMS analyzer region 34. As mentioned previously, to the inventors' knowledge, this focussing effect has never been observed or explained previously.

The 3-Dimensional Atmospheric Pressure Ion Trap

The gas flows between the cylinders of the FAIMS devices described above serve to carry the ions from one end of the device to the other end. In every case the action of the electric fields is perpendicular to the transporting motion of the gas flow. This is the reason the early devices were referred to as transverse field compensation ion mobility spectrometers. The present invention is the result of attempts to convert the 2-dimensional ion focussing action of the FAIMS-E 10 and FAIMS-R1-prototype 30 into a 3-dimensional trap by ensuring that the ions are caught in a physical location in which the gas flows and the electrical fields are not perpendicular, but rather act in opposition to each other. This creates a 3-dimensional atmospheric pressure ion trap.

Note that, in this disclosure, the term "ion focussing" is restricted to a 2-dimensional configuration. That is, if the ions are "focused", they will be restricted to a sheet-like structure, and the thin, flat sheet can extend in any direction, for any distance. For example, if ions are "focused" around the external surface of a long metallic cylinder, this will mean that they are restricted to be within a cylindrical space (composed of the ions) which is coaxial to, or surrounding the metallic cylinder. This sheet of ions will extend as far as the cylinder, and all around it continuously. On the other hand, in this disclosure the term "ion trapping" is restricted to the condition that an ion cannot move freely in any direction in 3-dimensional space. This is more restrictive than "focussing", in which the ion is free to move anywhere in the 2-dimensions e.g. along the length of the cylinder described in the example noted above or around the cylinder at a fixed radius.

3-dimensional ion traps for operation in vacuum chambers of mass spectrometers are well known, and several geometry's exist. However, the mechanism and operation of these vacuum-ion-traps is vastly different from that of the atmospheric pressure (760 torr) version of the ion trap described in this document. The physical geometry, the layout of the hardware components, and the electrical voltages applied in known 3-dimensional ion traps are in no way related to the present atmospheric version of the ion trap. Several embodiments of the 3-dimensional atmospheric pressure ion trap of the present invention will be considered below.

FAIMS-R2-Prototype

Figure 9A:
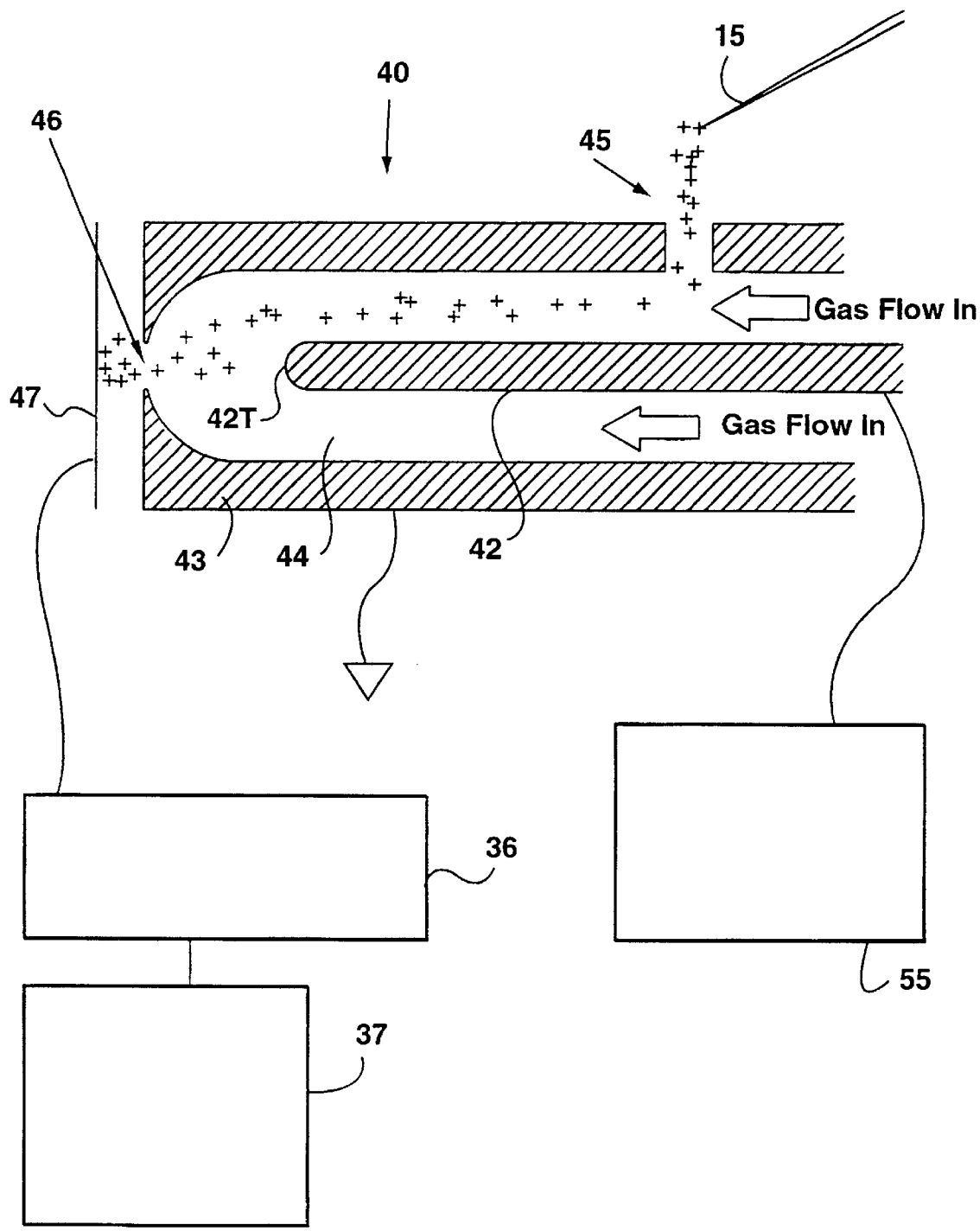
FIGS. 9A and 9B show schematically a first embodiment of a 3-dimensional atmospheric pressure high field asymmetrical waveform ion trap, referred to as the FAIMS-R2-prototype.
Figure 9B:
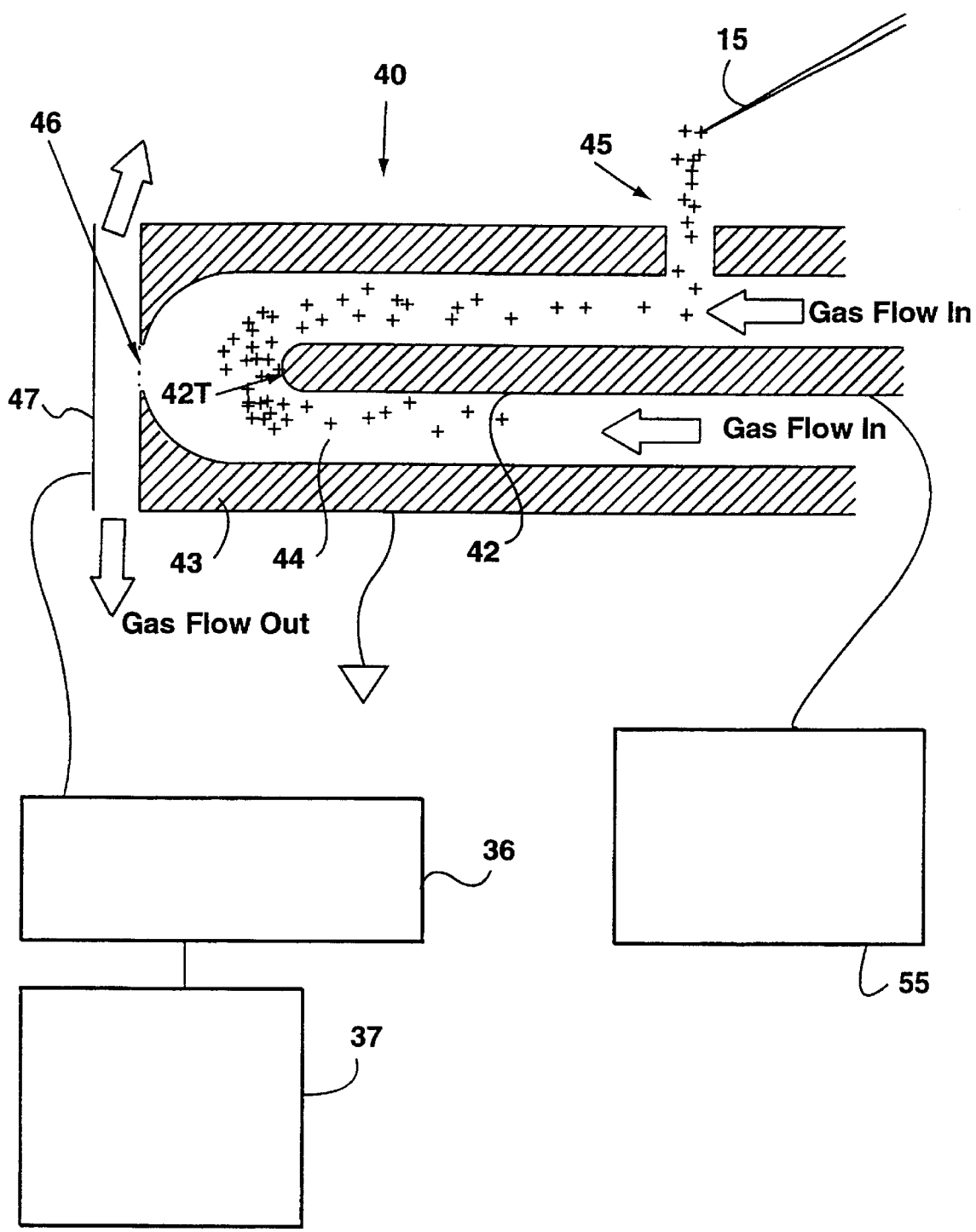

Referring to FIGS. 9A and 9B, the device which will be referred to as the FAIMS-R2-prototype 40 is shown. Here, the asymmetric waveform V(t) and the compensation voltage CV are applied to the inner, solid, electrode 42, having a diameter of about 2 mm. The outer, electrically grounded electrode 43 has an inner diameter of about 6 mm, thereby allowing an annular space of about 2 mm between the electrodes. This annular space has been referred to as the FAIMS analyzer or FAINS analyzer region 14, 34, 44 in the discussion above, and for simplicity we will continue to use this terminology. The ions are created by corona discharge using a corona needle 15 in a closed cell (not shown) located adjacent to a 0.5 mm hole through the wall of the outer cylinder. As shown in FIG. 9A, ions are driven by the high electric field generated by the corona discharge needle 15 (held at about +2000 V), through the 0.5 mm hole 45, and into the FAINS analyzer region 44 (only those ions travelling directly toward the hole 45 are shown for simplicity). Inside the FAIMS analyzer region 44, near this hole 45, the electric fields and the gas flow (shown to be flowing from right to left in FIGS. 9A and 9B) are perpendicular to each other and the ions experience the 2-dimensional focussing effect described in the sections above in relation to the FAIMS-R1-prototype 30. However, the inner electrode 42 in the device shown in FIG. 9A, terminates about 1–4 mm from the end of the outer electrode 43. The inner surface of the outer electrode 43 at the downstream end is contoured in such a way as to maintain approximately the same electric fields (i.e. created by the application of DV and CV) as would be experienced along the length of the FAIMS analyzer region 44. The end of the outer electrode 43 has an exit grid 46 comprising a hole (about 2 mm) which is covered with a fine, high transmission metallic screen. The gas flowing through the device 40 also flows freely through the grid 46 and exits from the space between the outer electrode 43 and a collector plate 47. In the absence of any applied voltages (i.e. DV and CV=0) the ions will travel through the device very much as shown in FIG. 9A. The ions enter the analyzer region 44, flow with the gas out through the exit grid 46 of the outer electrode 43, and the few remaining ions are attracted to an ion collector plate 47 biased at about −5 V. The collector plate 47 was connected to a high gain current amplifier or electrometer 36 (e.g. Keithly 428) and an oscilloscope 37.

The application of an asymmetric waveform of the type shown in FIG. 7 resulted in the ion focussing behavior described above for the conventional FAIMS-E 10 and FAIMS-R1-prototype 30, except that the focussing action extends around the generally spherically shaped terminus 42T of the inner electrode 42, as shown in FIG. 9B. This means that the ions cannot escape from the region around the terminus 42T of the inner electrode 42. This will only occur if the voltages applied to the inner electrode 42 are the appropriate combination of CV and DV as described in the discussion above relating to 2-dimensional focussing. If the CV and DV are suitable for the focussing of an ion in the FAIMS analyzer region 44, and the physical geometry of the inner surface of the outer electrode 43 shown in FIGS. 9A and 9B does not disturb this balance, the ions will collect near the terminus 42T as shown in FIG. 9B. Several contradictory forces are acting on the ions in this region near the terminus 42T of the inner electrode 42. The ion cloud shown near the terminus 42T of the inner electrode 42 in FIG. 9B would like to travel from right to left to the exit grid 46 in the manner shown in FIG. 9A, because of the force of the gas flow. This also means that the ions cannot migrate back from left to right, toward the ionization source 15. The ions that get too close to the inner electrode 42 are pushed back away from the electrode 42, and those near the outer electrode 43 will migrate back towards the inner electrode 42, because of the application of the negatively polarized CV. The ions are captured in every direction, either by forces of the flowing gas, or by the electric fields (electric potential well) of the FAIMS mechanism.

Note that, while the above discussion refers to the ions as being "captured" or "trapped", in fact, the ions are subject to 'diffusion'. Diffusion always acts contrary to focussing and trapping. The ions will always require an electrical, or gas flow force to reverse the process of diffusion. This means that although the ions may be focused into an imaginary cylindrical zone in space (with almost zero thickness), or within a 3-dimensional ion trap, in reality it is well known that the ions will actually be dispersed in the vicinity of this idealized zone in space because of diffusion. This means that ions will always be "distributed" over some region, rather than all precisely located in the same place. This is important, and should be recognized as a global feature superimposed upon all of the ion motions discussed in this document. This means that, for example, a 3-dimensional ion trap will actually have real spatial width, and leak for several physical, and chemical reasons.

Expanding on the chemical effects in FAIMS, if an ion collides with a neutral molecule and temporarily forms a stable complex, this complex may drift out of the FAIMS focussing or trapping region because this new complex has high field mobility properties which are different from the original ion. This means that the complex may have behavior at high electric field (see FIG. 1) which differs from the original simple parent ion. For example (at the extreme) the original ion may be of type A, and the new complex of type C shown in FIG. 1. If this is the case, the new complex will not be trapped at the prevailing DV and CV conditions. The collision of any of these ions with the walls of the device will soon result in loss of the ions from the trap. Although the original ion itself may continue to be trapped, the removal of this ion via "chemical" effects is entirely possible, and is the reason the FAIMS analyzer will fail in the presence of significant water vapor or contaminants in the gas flows. The FAIMS analyzer works best in very clean conditions. During operation in P2 mode, the requirement for a high purity gas is somewhat relaxed.

Figure 10A:
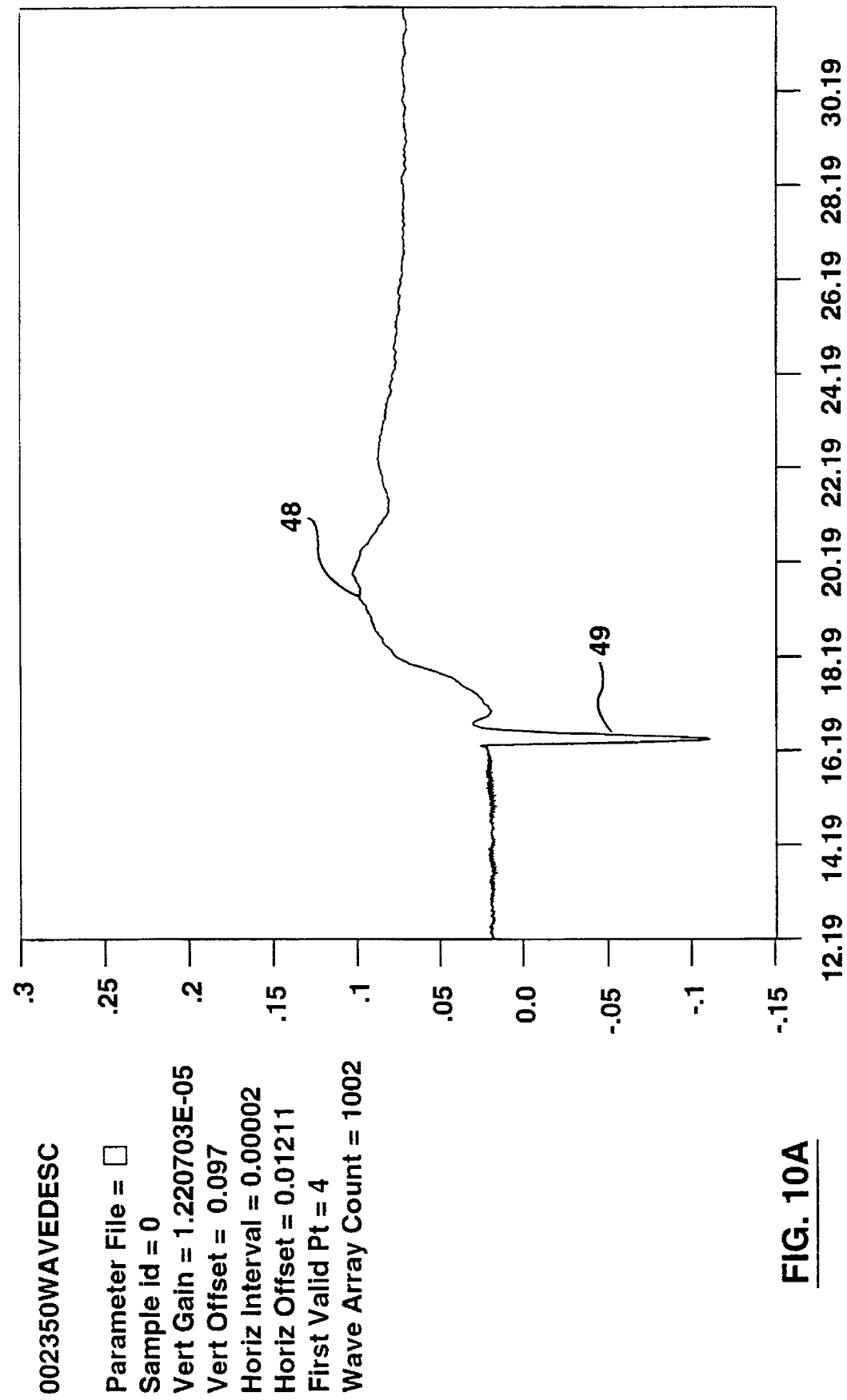
FIGS. 10A through 10I show the experimental results for extraction of ions trapped using the FAIMS apparatus of FIGS. 9A and 9B, with voltages ranging from +1 V to +30 V.
Figure 10B:
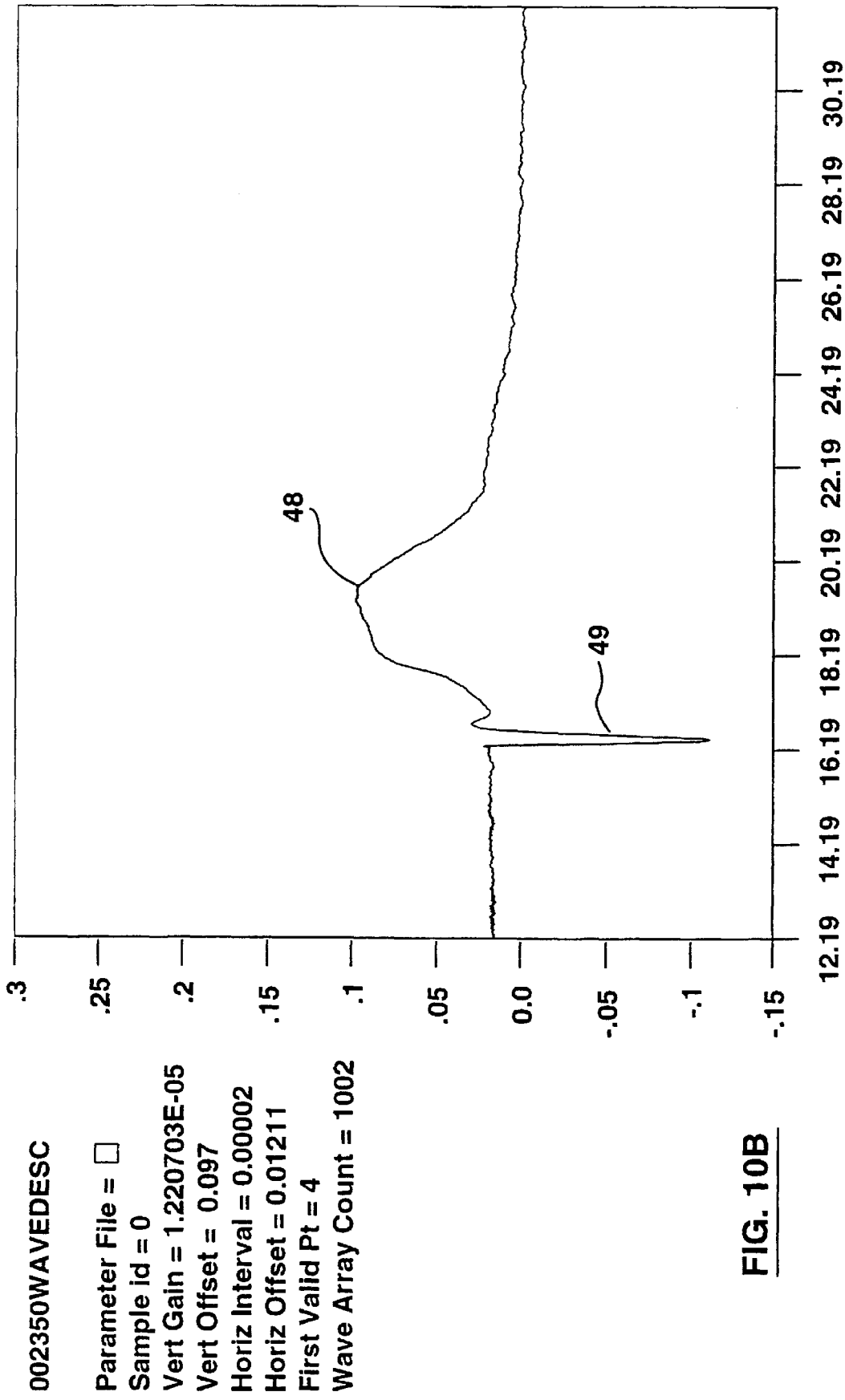
Figure 10C:
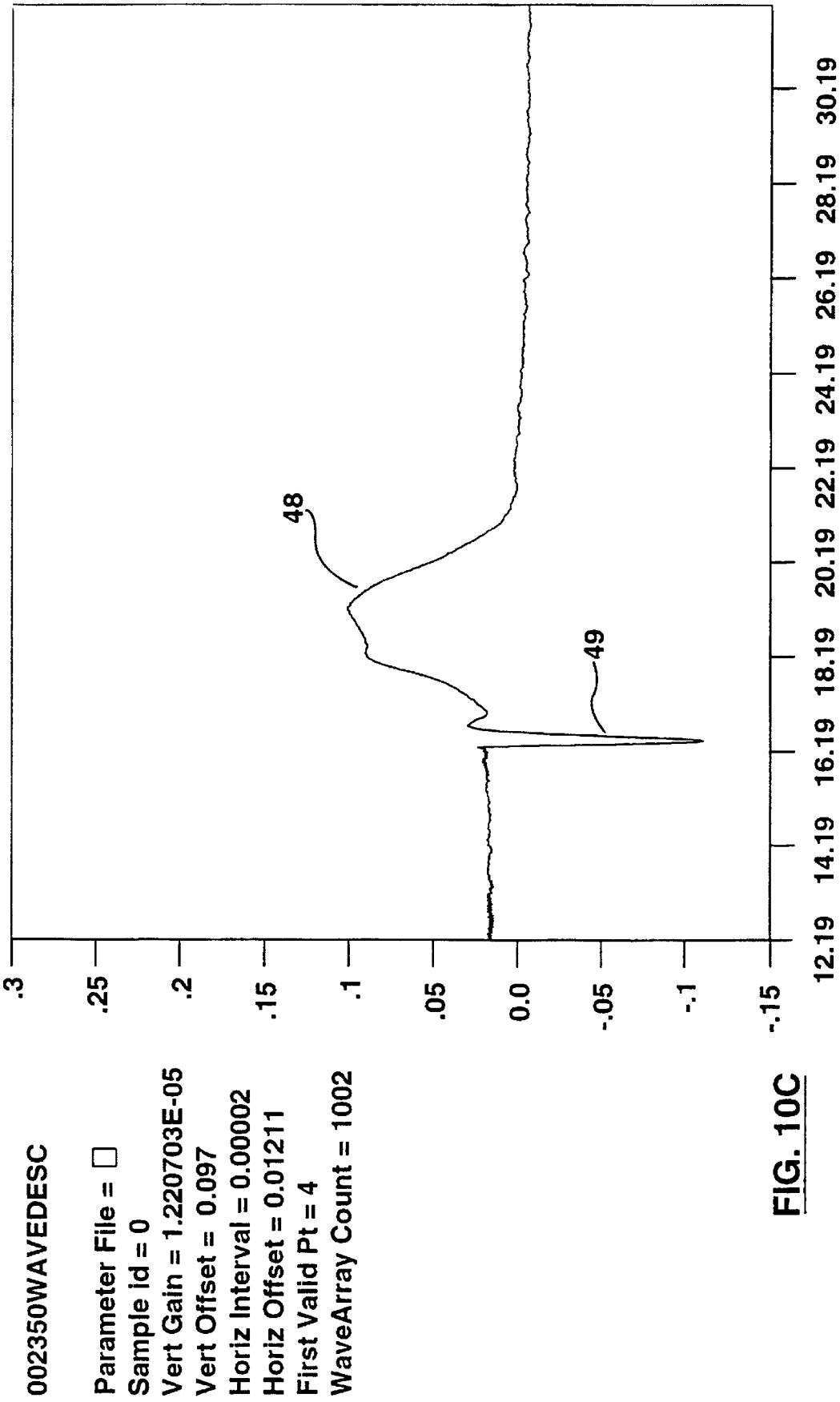
Figure 10D:
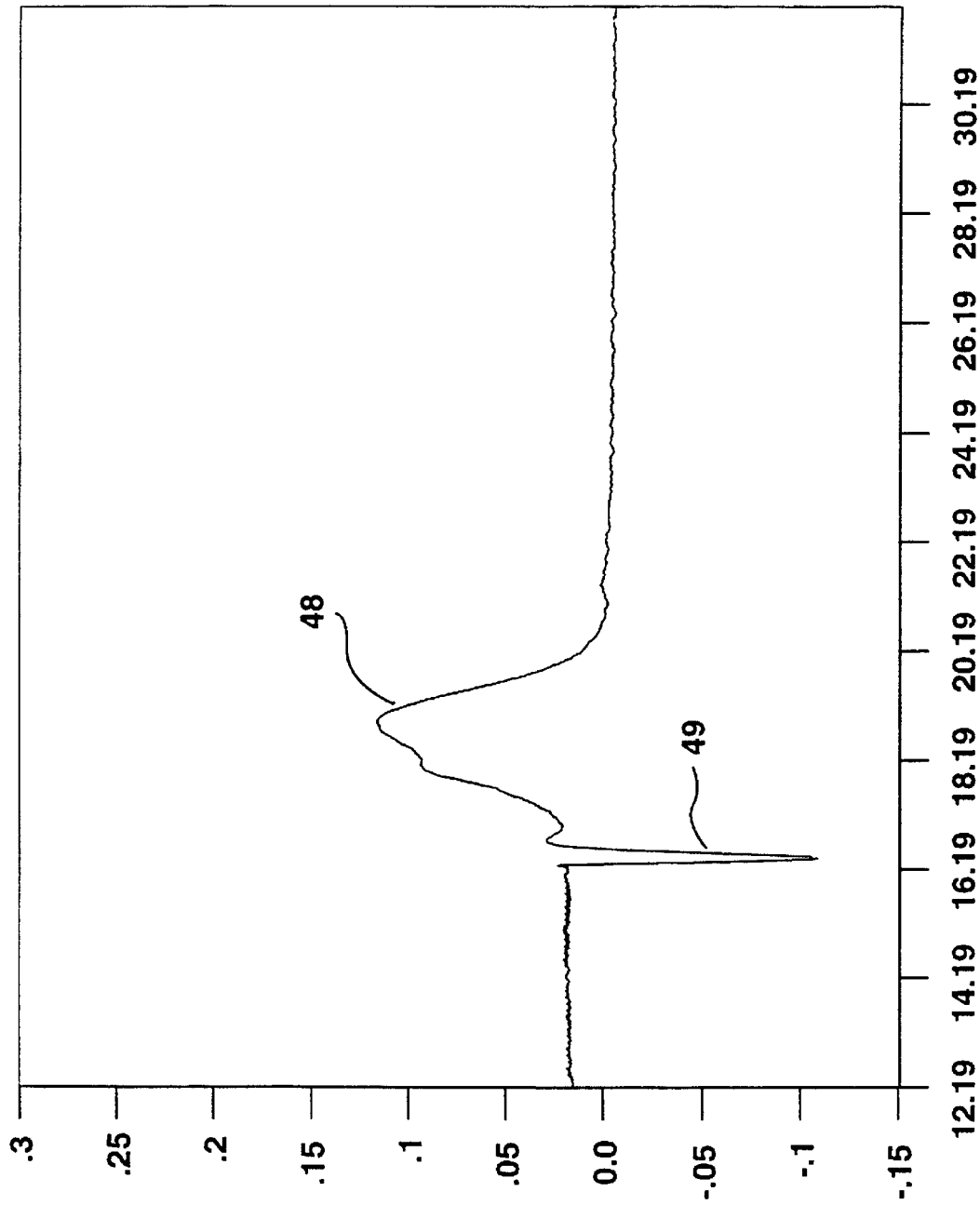
Figure 10E:
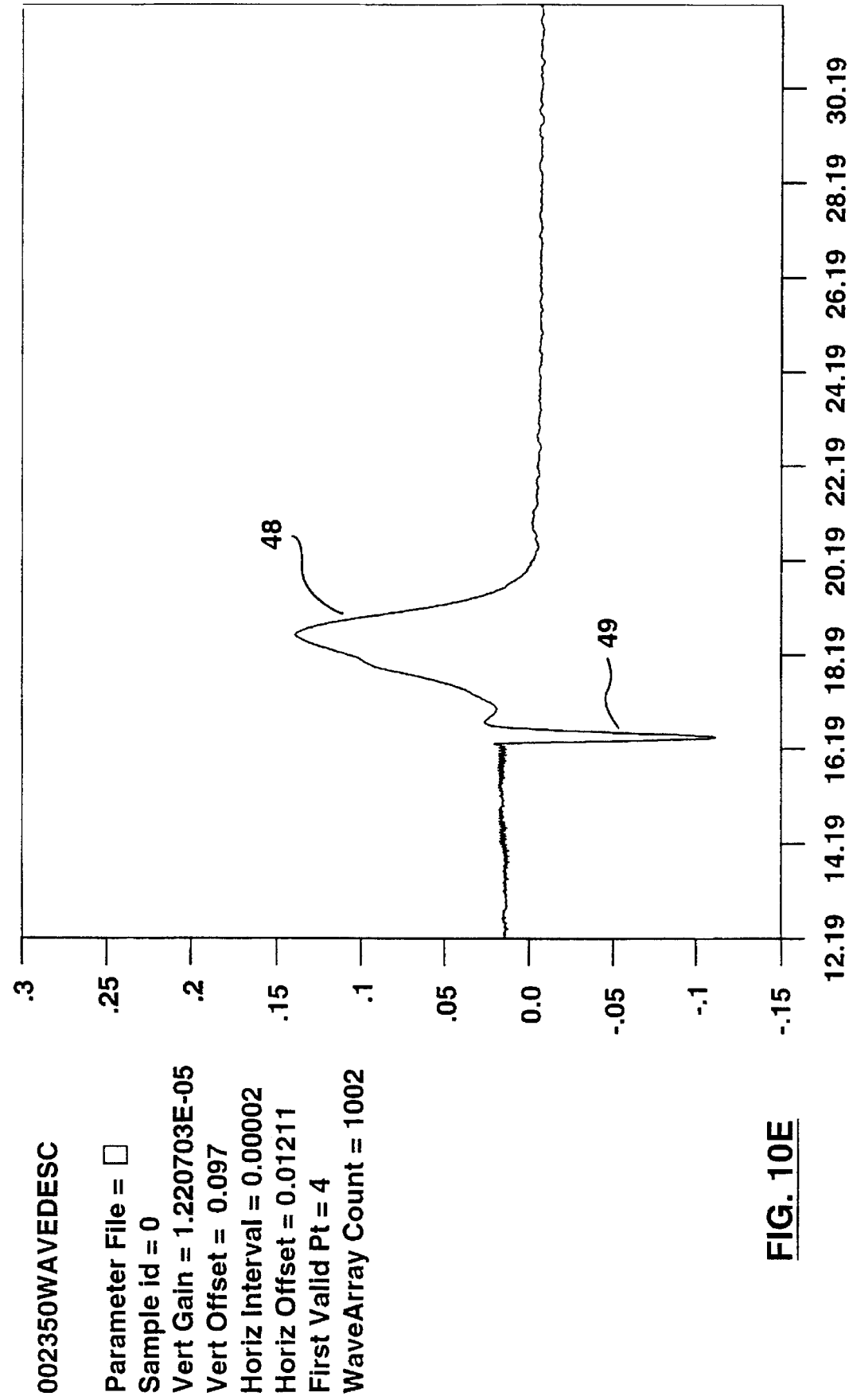
Figure 10F:
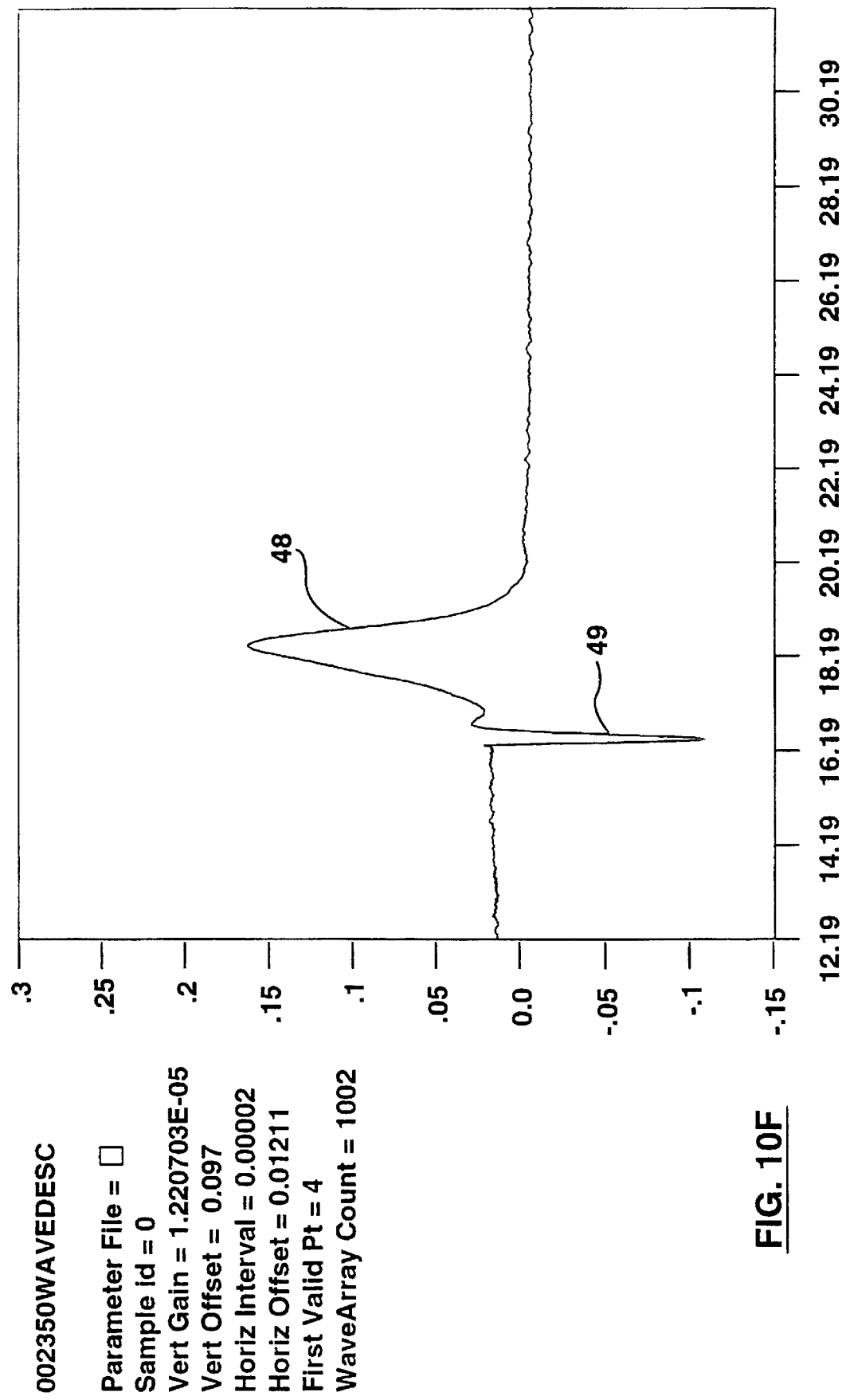
Figure 10G:
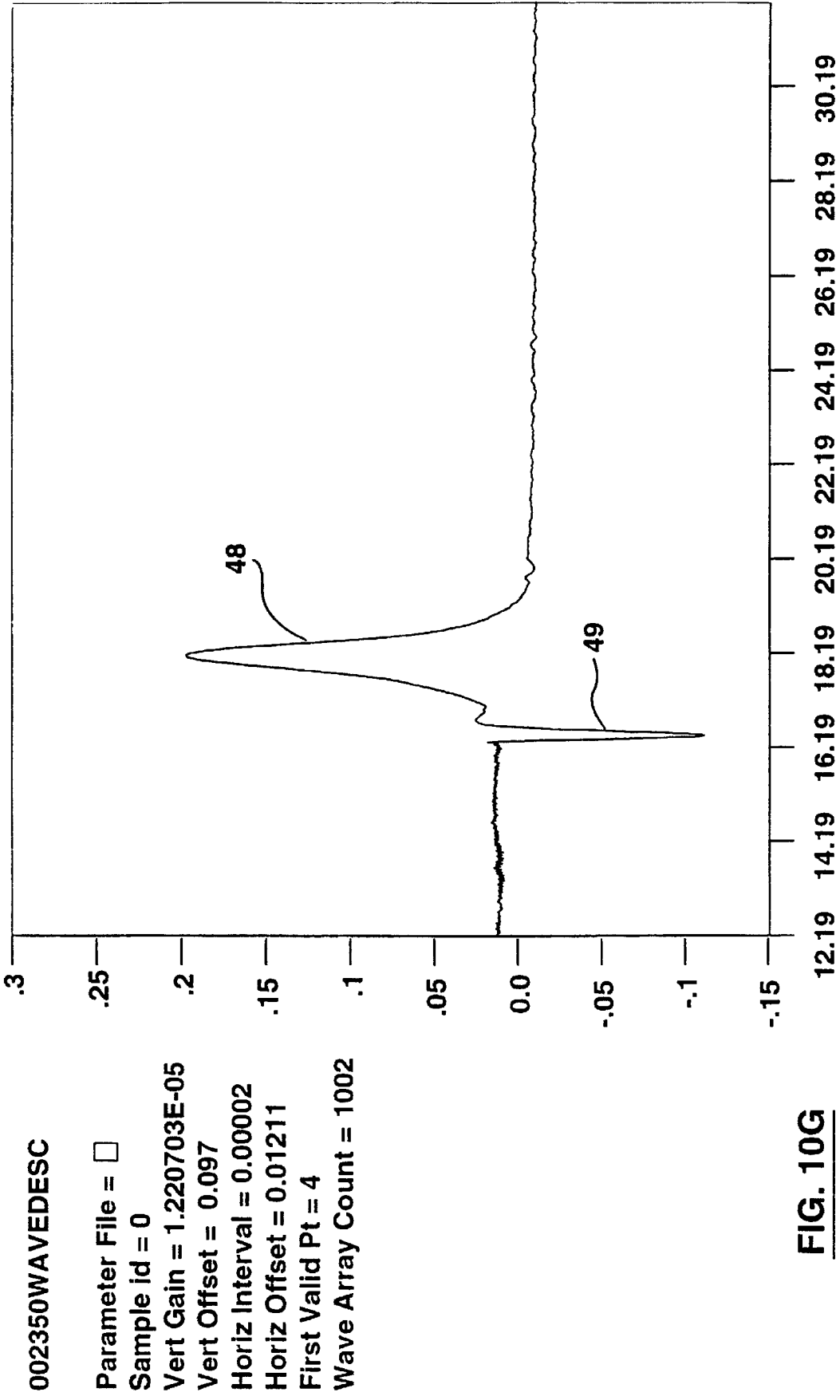
Figure 10H:
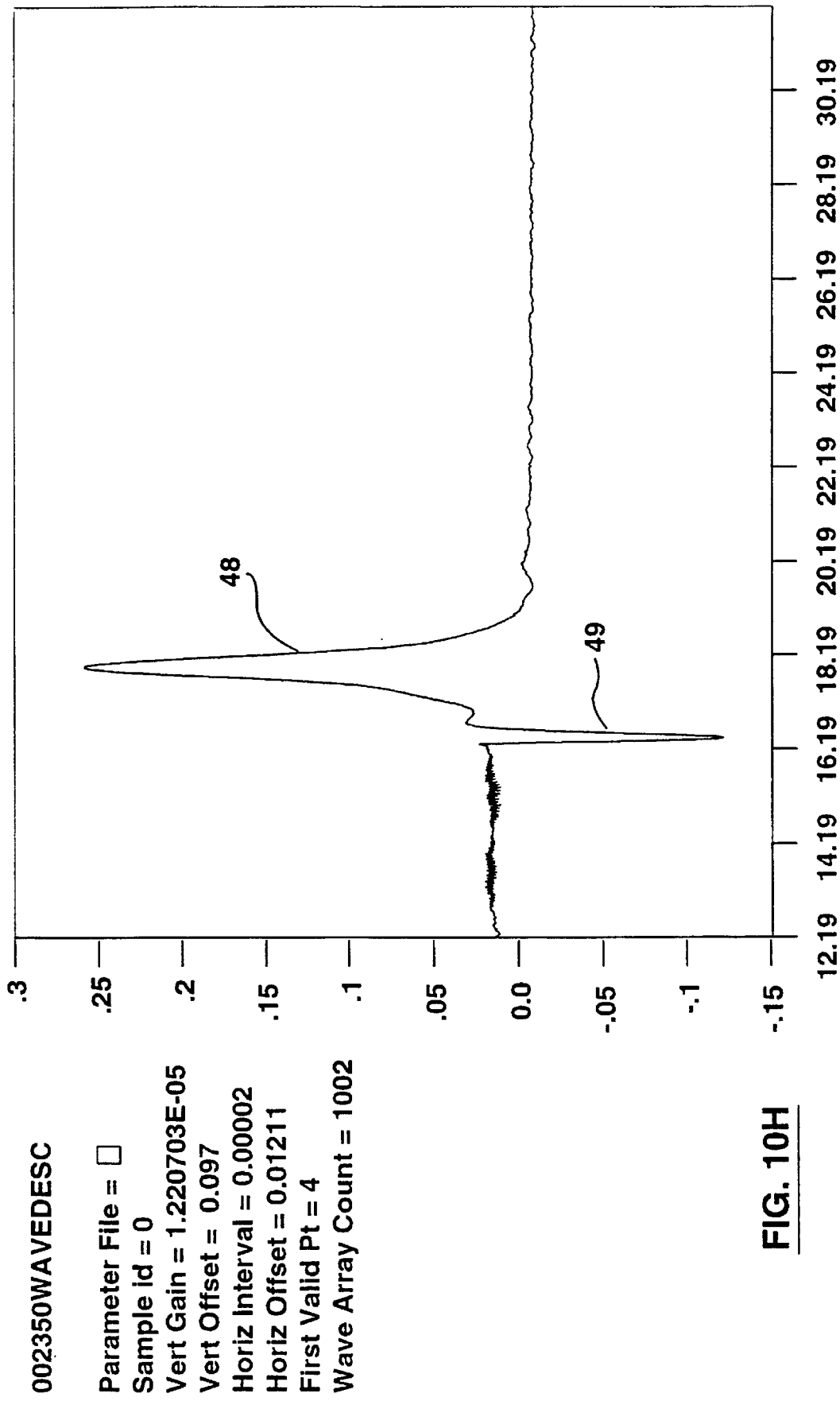
Figure 10I:
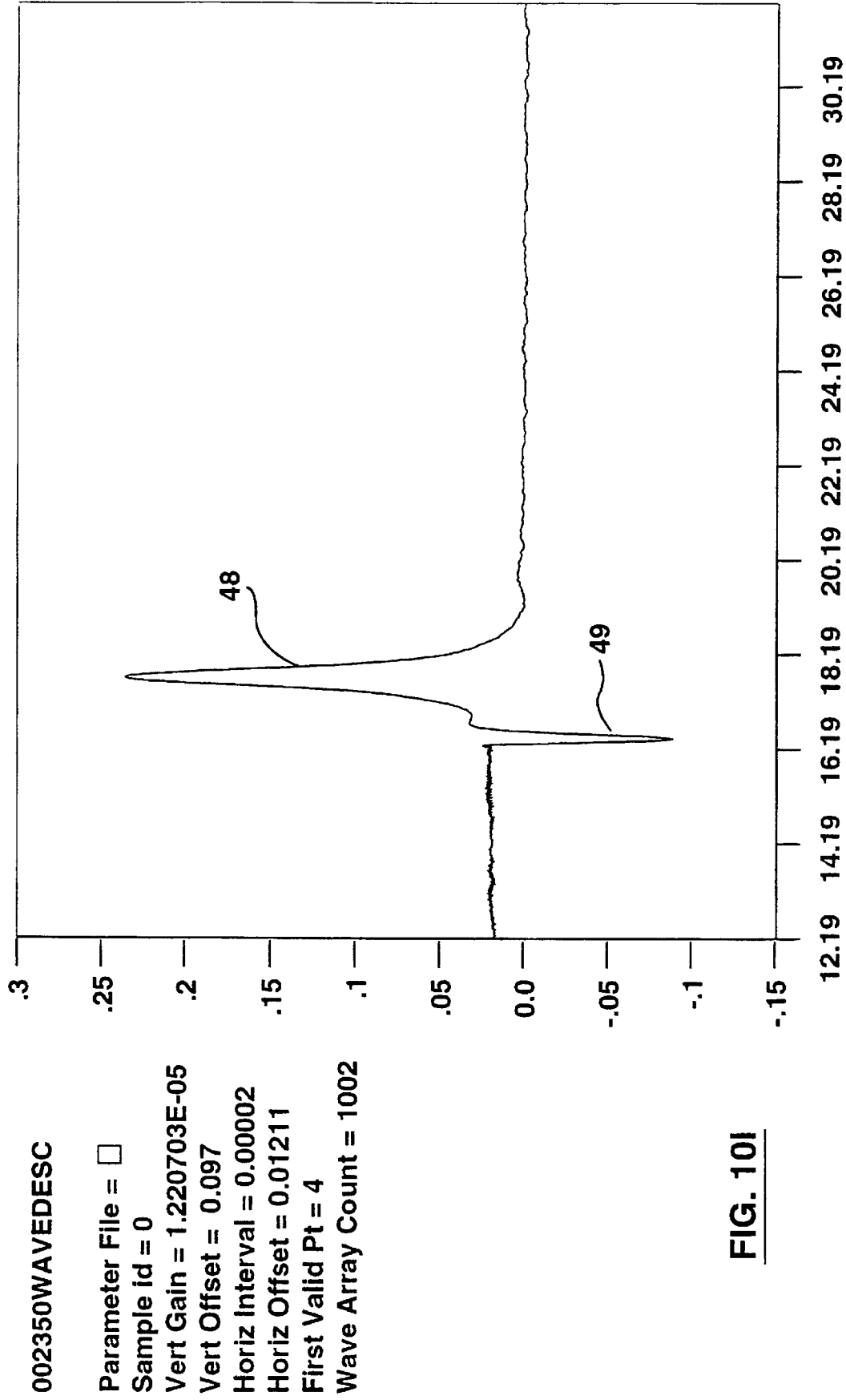

Now referring to FIGS. 10A through 10I, experimental results with the FAIMS-R2-prototype 40 are shown. The dimensions of the electrodes were described above, for FIGS. 9A and 9B. The DV was approximately 2000 V, CV was −12 V, and the gas flow through the device was 0.9 L/min. The DV and CV were applied to the inner electrode for about 16 ms, then these voltages were replaced by an extraction voltage applied to the inner electrode 42. The DC extraction voltage applied to the inner electrode 42 pushes the ions away from the inner electrode 42 towards the exit grid 46, whereby the gas flow carries these ions through the grid 46 (with some percentage of the ions lost in collisions with this grid 46). The traces in FIG. 10A through 10I represent results for the ions extracted with voltages ranging from +1 V (FIG. 10A) to +30 V (FIG. 10I). The extraction of trapped ions results in a positive pulse 48 recorded in FIGS. 10A–10I. The negative pulse 49 shown in the figures is the electronic transient noise that occurs when the DV and CV are removed and replaced by the extraction voltage. It is clear from the data shown in FIGS. 10A–10I that an increase in the extraction voltage will yield a shorter, more intense ion signal 48. This occurs since the ions are pulsed out of the trap more vigorously with the +30 V than the +1 V. The experimental results shown in FIGS. 10A–10I verify the hypothesis that a cloud of ions accumulates near the terminus 42T of the inner electrode 42. A pulse of ions, as shown in FIG. 10I, could not be extracted from the FAIMS-R2-prototype 40 unless some ions were available near the terminus 42T of the inner electrode 42.

FAIMS-R3-Prototype

Figure 11A:
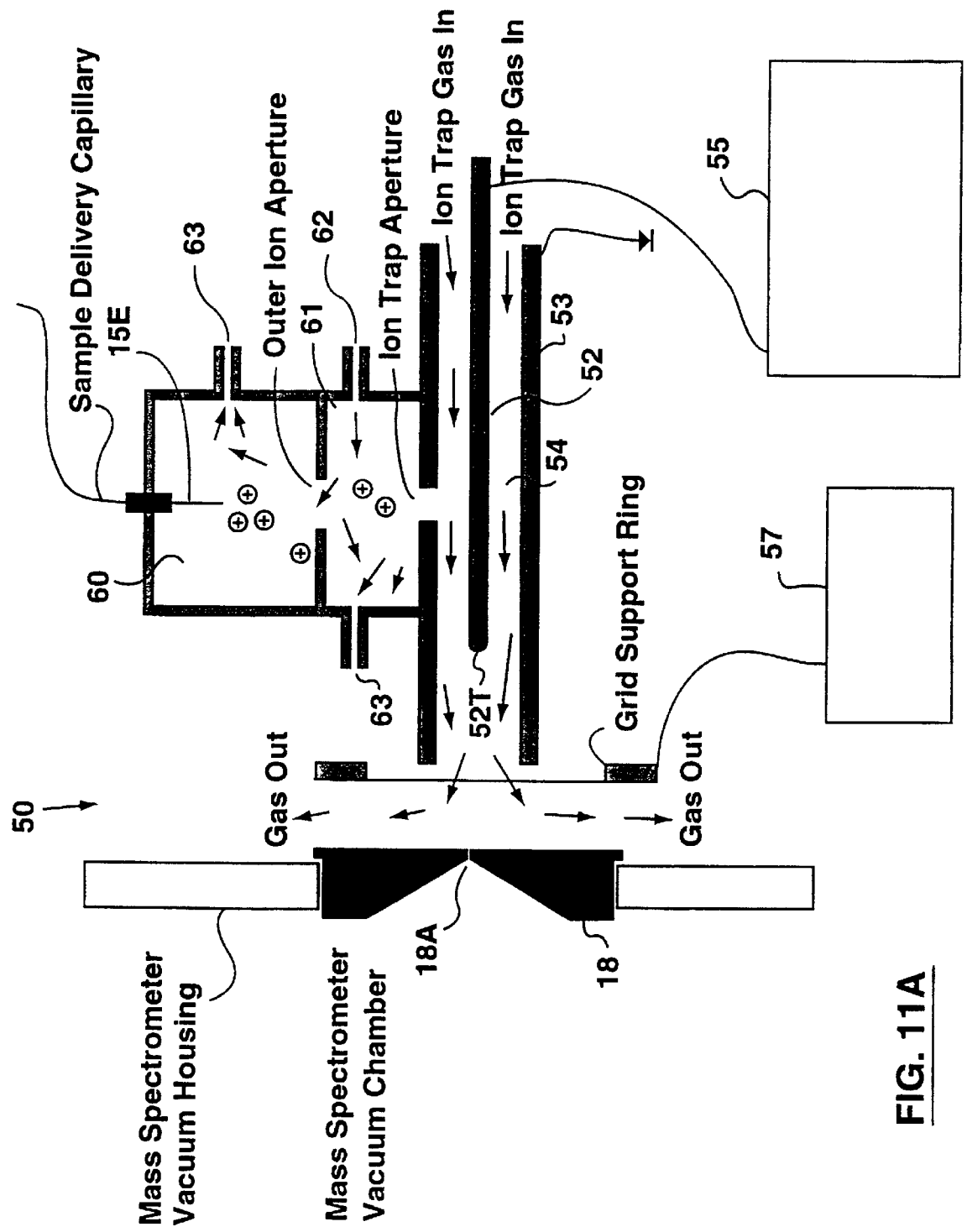
FIGS. 11A–11C show a second embodiment of a 3-dimensional atmospheric pressure high field asymmetrical waveform ion trap, referred to as the FAIMS-R3-prototype.
Figure 11B:
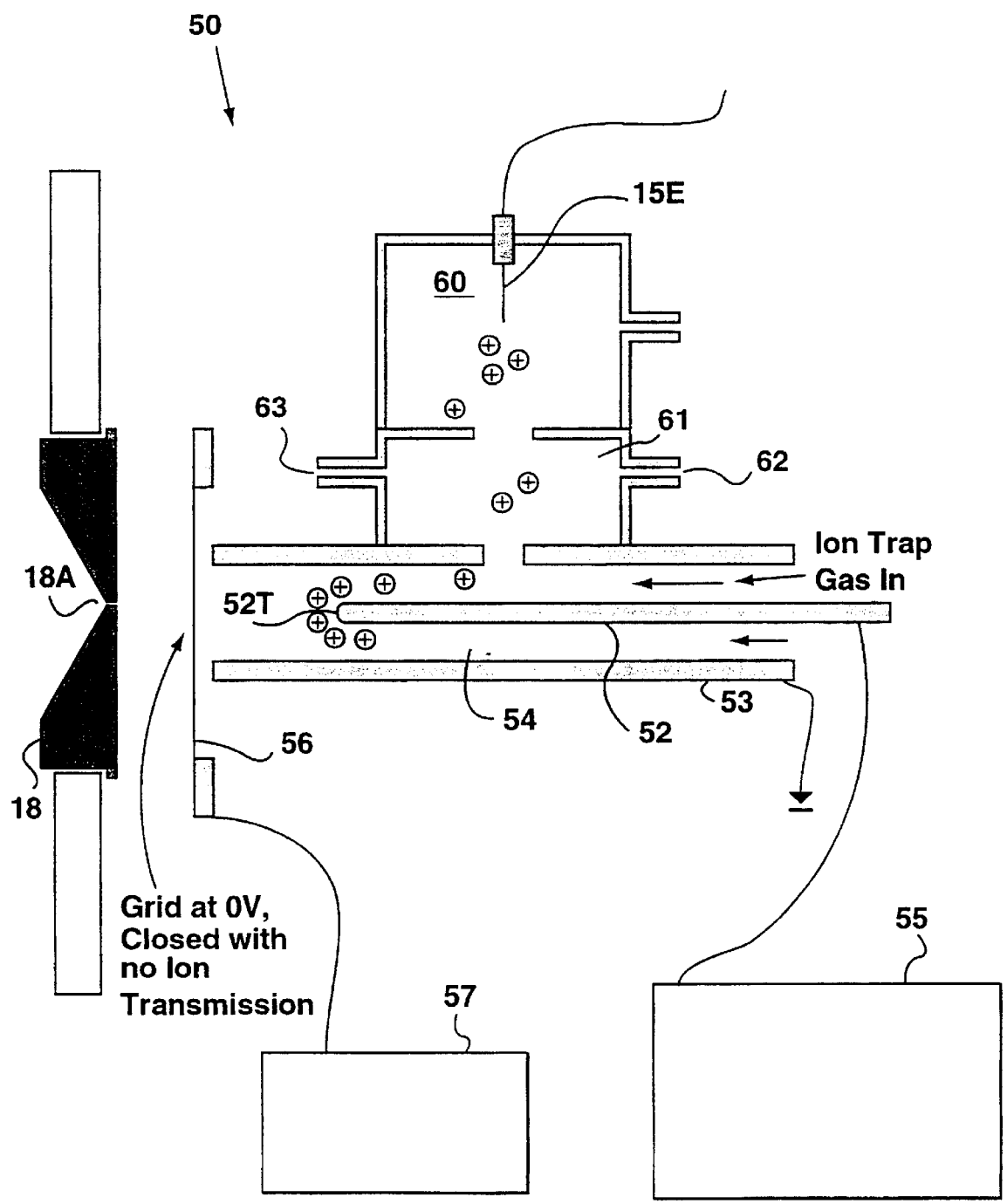
Figure 11C:
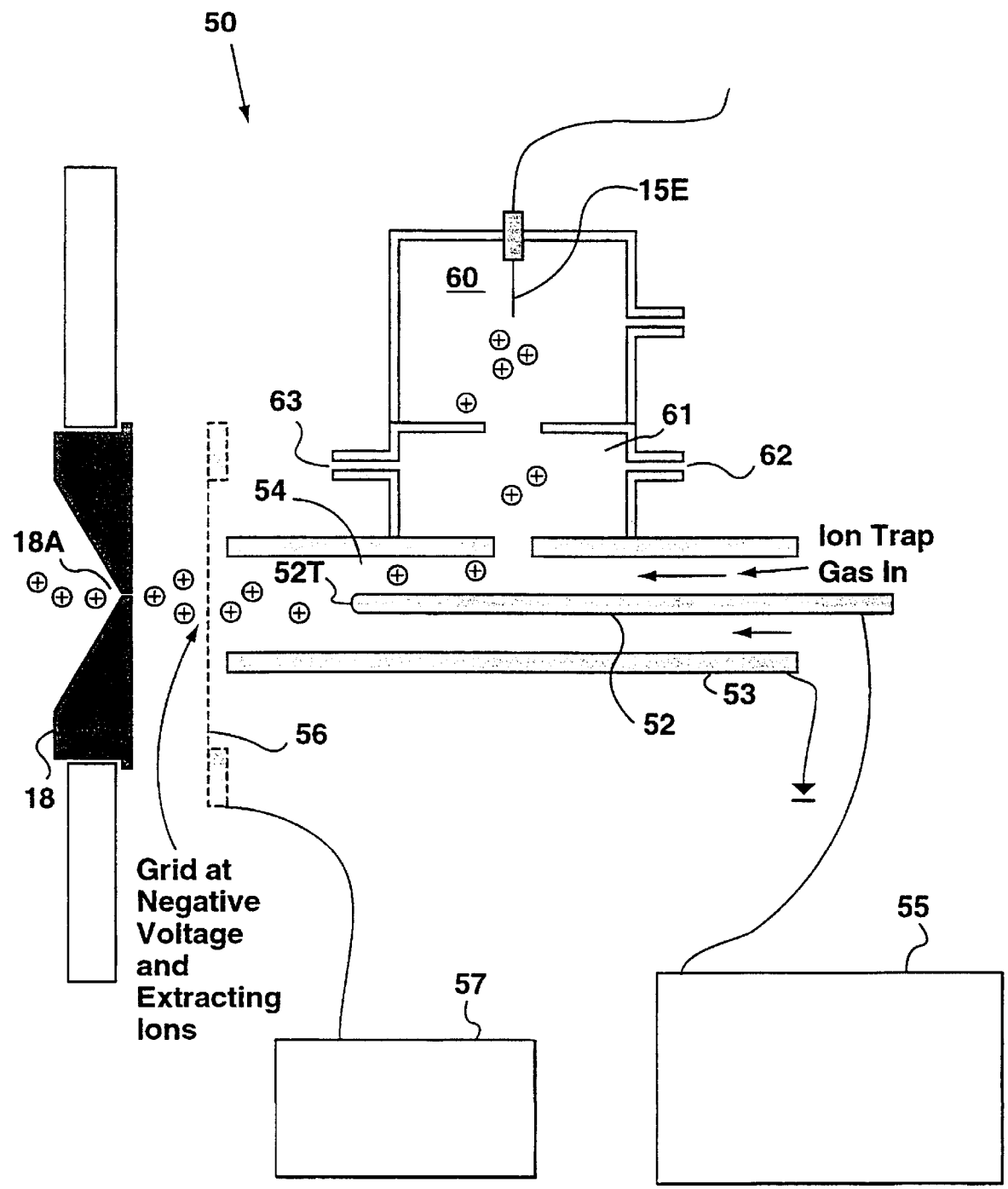

Now referring to FIGS. 11A through 11C, the FAIMS-R3-prototype 50 is shown. This device is configured for detection by mass spectrometry, and a sampler cone 18, through which gas and ions are pulled into the vacuum chamber of a mass spectrometer is shown on the left side of FIGS. 11A–11C. The right side of the vacuum housing, and sampling cone 18, is substantially at atmospheric pressure. The left side of those components is labelled "Mass Spectrometric Vacuum Chamber", and is typically below 1 torr pressure. In most systems a second orifice (not shown) leads to the mass analyzer region of the mass spectrometer which is usually below $10^{-5}$ torr pressure.

The FAIMS-R3-prototype analyzer 50 shown in FIG. 11A consists of an inner, solid, cylindrical electrode 52 of about 2 mm diameter, and an outer electrode 53 which is about 6 mm inner diameter. The center electrode 52 is powered, through an electrical connection, by an asymmetric waveform generator power supply 55. Both DV and CV are supplied by this generator 55. The waveforms, and the timing diagram are shown in FIG. 11D. As shown in FIG. 11D, the asymmetric waveform is applied continuously to the inner electrode 52.

Referring back to FIG. 11A, gas enters the FAIMS-R3-prototype 50 from the right side and flows along the annular space comprising the FAIMS analyzer region 54, and out through the open end of the outer electrode 53. Adjacent to the open end (left side) of the outer cylinder 53 is an exit grid 56 comprising a fine, thin-wired metallic grid which is electrically isolated from the outer electrode 53, and has an electrical connection to a grid electric pulse generator power supply 57. The voltage on the grid 56 can be changed step-wise using this power supply. The grid voltage and timing diagram is shown in FIG. 11D. The grid is typically maintained between −5 and +5 V during the ion storage time (e.g. 0 V) shown in FIG. 11D. The grid will then be stepped (100 ns transition) to between −5 V and −50 V (e.g. −15 V in FIG. 11D) in order to extract the ions from the 3-dimensional atmospheric pressure trap which is located at the spherical terminus 52T of the inner electrode. FIG. 11B shows schematically the approximate location of the ions during the storage period. It should be kept in mind that the ions trapped here must have the correct high field ion mobility (see FIG. 1) so that their "net" motion is zero at the combination of CV and DV being applied to the storage device (the term "net" is used because the ion is constantly moving back-and-forth due to the application of the asymmetric waveform: if the ion returns to the same location repeatedly, then the "net" motion caused by the application of DV and CV is zero). For example, the $(H_2O)_nH^+$ ions will be stored in the geometry shown in FIGS. 11A–11C at a DV of about +2000 V and a CV of approximately −10 V (typical of P1 mode ). At conditions very different (e.g. at DV 2000 and CV +10 V) from this combination of DV and CV, the $(H_2O)_nH^+$ ions will not assemble into one physical location as shown in FIG. 11B. Instead, these ions will collide with the walls of the cylinders 52, 53. At a second set of DV and CV conditions, such as the DV 2500 and CV −5 V, another ion (e.g. (Leucine)H⁺) may be able to collect at the tip 52T of the inner electrode 52 as shown in FIG. 11B.

Near the terminus 52T of the inner electrode 52 shown in FIG. 11B, the ions are restricted in motion because of several contrary forces. The gas flowing along the FAIMS analyzer region 54 applies a force which will prevent migration of ions from the left to right (FIG. 11B) back toward the ion trap gas inlet, and this force will also tend to pull the ions out of the trap towards the exit grid 56 shown at the left end of the outer electrode. The electrical forces characteristic of FAIMS maintain the ions at a fixed distance from the sides of the inner electrode 52: (1) the ions which are too distant from the inner electrode 52 are attracted to the inner electrode 52 because of the negative polarity of the applied dc offset, i.e. a negative CV; and (2) the ions close to the inner electrode 52 are pushed away because of the increase of the ion mobility at high field (see FIG. 1) assuming the ions are of type P1. Details of the ion motions are presented below.

FIG. 11C illustrates the removal of ions from the 3-dimensional atmospheric pressure trap via a stepwise change to the voltage applied to the grid electrode 56. If the voltage applied to the grid 56 is decreased from, say, 0 V to −15 V as shown in the timing diagram FIG. 11D, the well depth of the ion trap is reduced or eliminated, and the ions are free to escape under the influence of the gas flow, or by the electric field which might pull the ions toward the exit grid 56.

The FAIMS-R3-prototype 50 shown in FIGS. 11A–11C is appropriate for detection of ions produced by electrospray ionization (ESI). FAIMS is highly sensitive to moisture and contaminants in the gas entering the analyzer region. It is common that contaminants, or too much water vapor, will result in complete loss of signal, and failure of the FAIMS to function in the manner described in this document. Since electrospray ionization involves the high-voltage-assisted-atomization of a solvent mixture, the amount of water and other volatile solvents is far too high to be tolerated in the FAIMS analyzer region 54. This will mean that the ESI-FAIMS combination will always require a type of gas-isolation, curtain gas, or counter-current gas flow, to prevent neutral solvent molecules from entering the FAIMS analyzer region 54. One method to accomplish this is shown in FIGS. 11A–11C. The FAIMS is separated from the ESI chamber 60 by a small chamber 61 which has provision for gas inlets 62 and gas outlets 63. If a flow of gas enters this intermediate chamber 61, and a portion of the gas flows toward the ESI chamber, then the neutral solvent molecules will exit via the port on the ESI chamber, and will be prevented from entering the ion trap aperature. The electrospray needle 15E, shown in FIGS. 11A–11C is more likely to be in a horizontal plane or lower than the FAIMS analyzer region 54, rather than the higher, vertical position shown. This minimizes the tendency for very large droplets to fall via gravity, into the FAIMS analyzer region 54. In a horizontal or lower configuration the large droplets will fall into the bottom of the ESI chamber 60, which could (optionally) have a drain for removal of excess solvent. Alternatively, if the ion trap gas inlet is closed off, gas entering the purge gas inlet could be used to both, help in desolvation, and a portion of this gas flow would be used to carry the ions along the FAIMS analyzer region 54 from right to left in FIG. 12.

Figure 12:
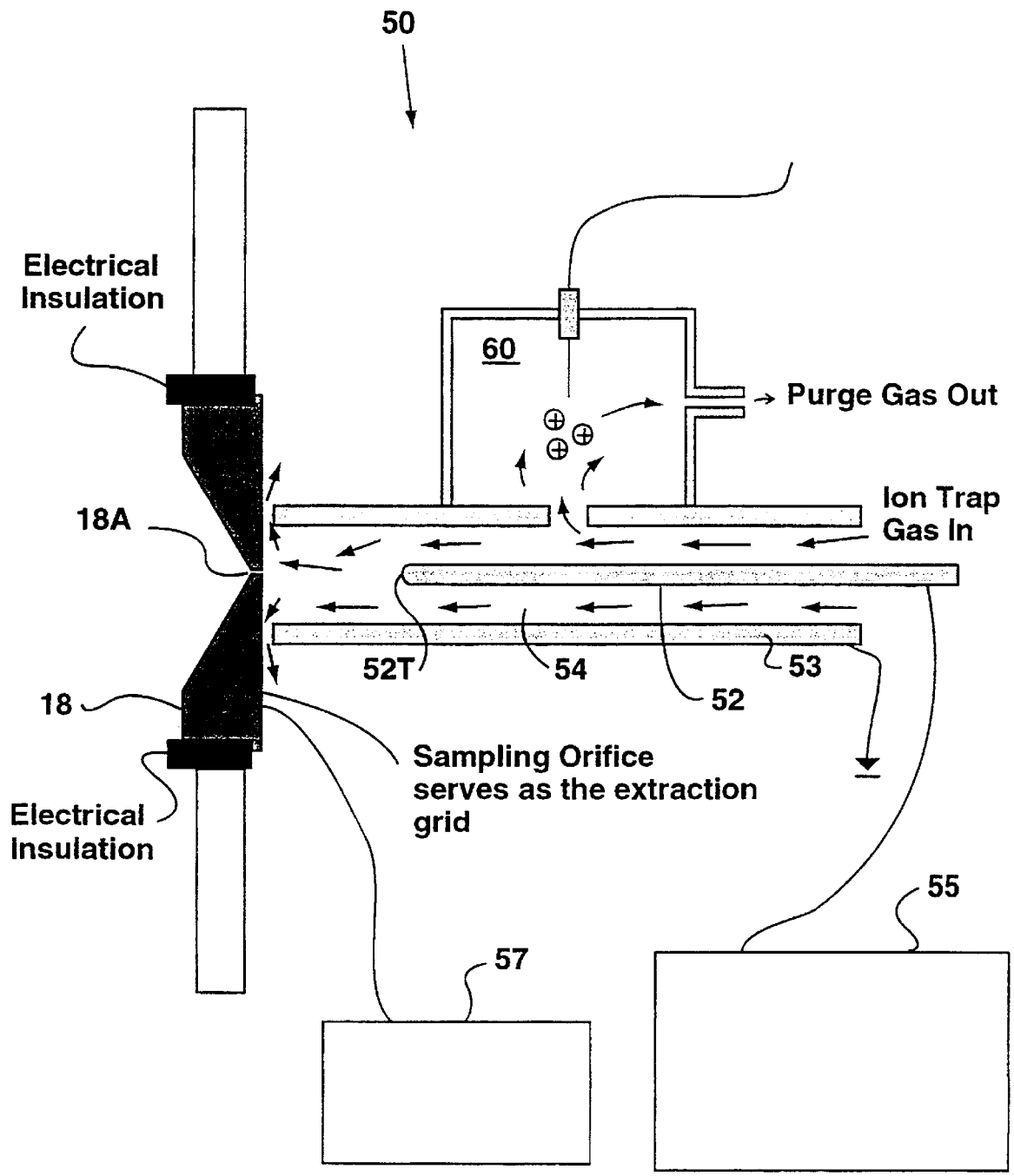
FIG. 12 shows an alternative embodiment of the FAIMS apparatus of FIGS. 11A–11C, having a simplified electrospray ionization chamber, and using the sampler cone as an extraction grid.

The counter-current of gas can be achieved in a second way shown in FIG. 12 (gas flows are emphasized, and most of the ions are omitted). If the FAIMS analyzer gas flow is adjusted so that some of the gas will exit the FAIMS analyzer region 54 into the ESI chamber 60, the entrance of neutral contaminants can be avoided. This may result in higher ion transmission than that for the device shown in FIGS. 11A–11C. Note also that the exit grid electrode 56 (FIGS. 11A–11C) has not been shown in FIG. 12. In this embodiment the 'extraction' pulse that destroys the ion trap is applied to the mass spectrometer sampling cone 18.

FAIMS Ion Trapping Mass Spectrometry Experiments: Instrumental Overview

Figure 13A:
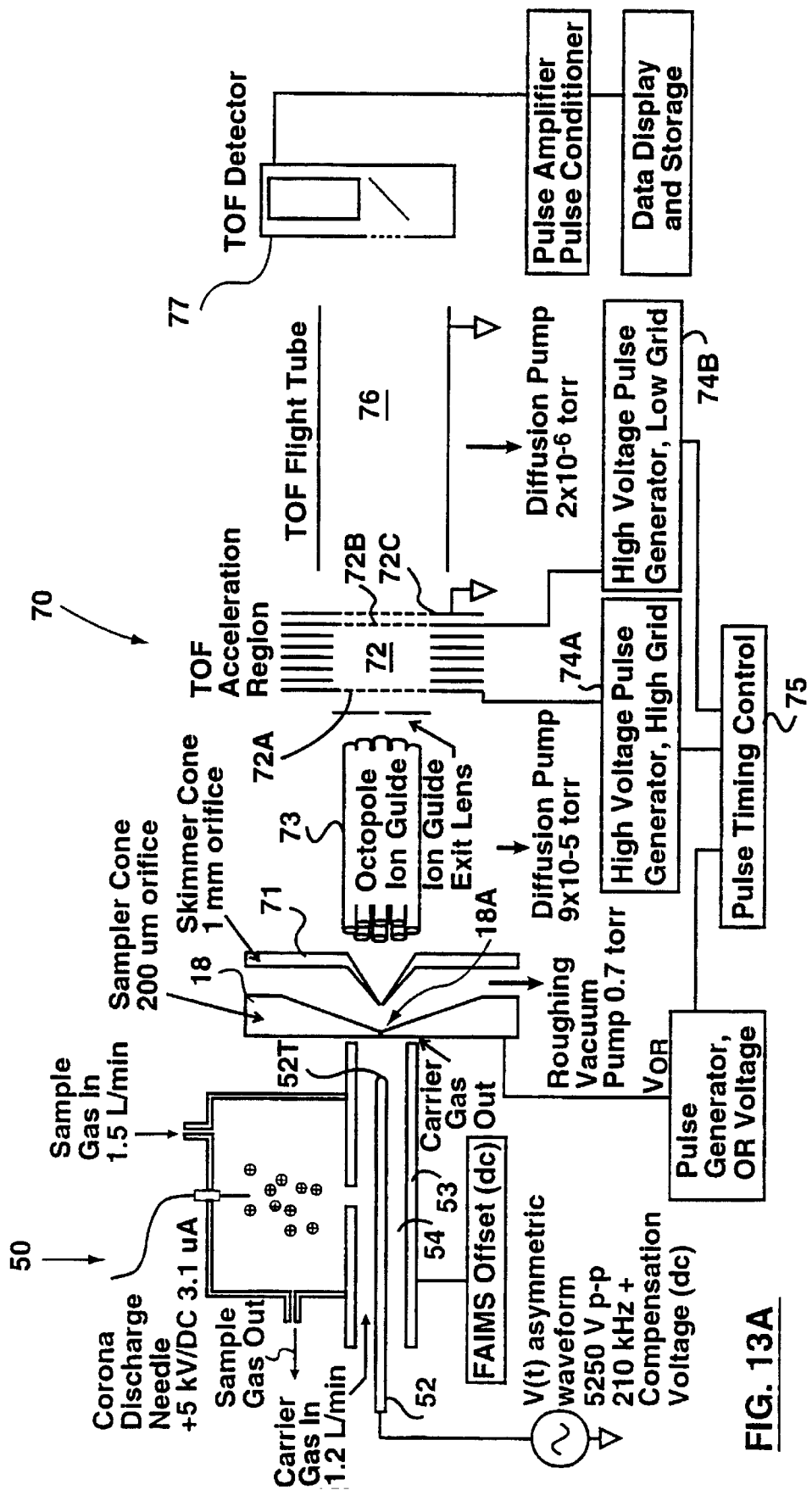
FIG. 13A is a schematic view of a system comprising an apparatus similar to the FAIMS apparatus disclosed in FIG. 12, and a time-of-flight (TOF) mass spectrometer.
Figure 13B:
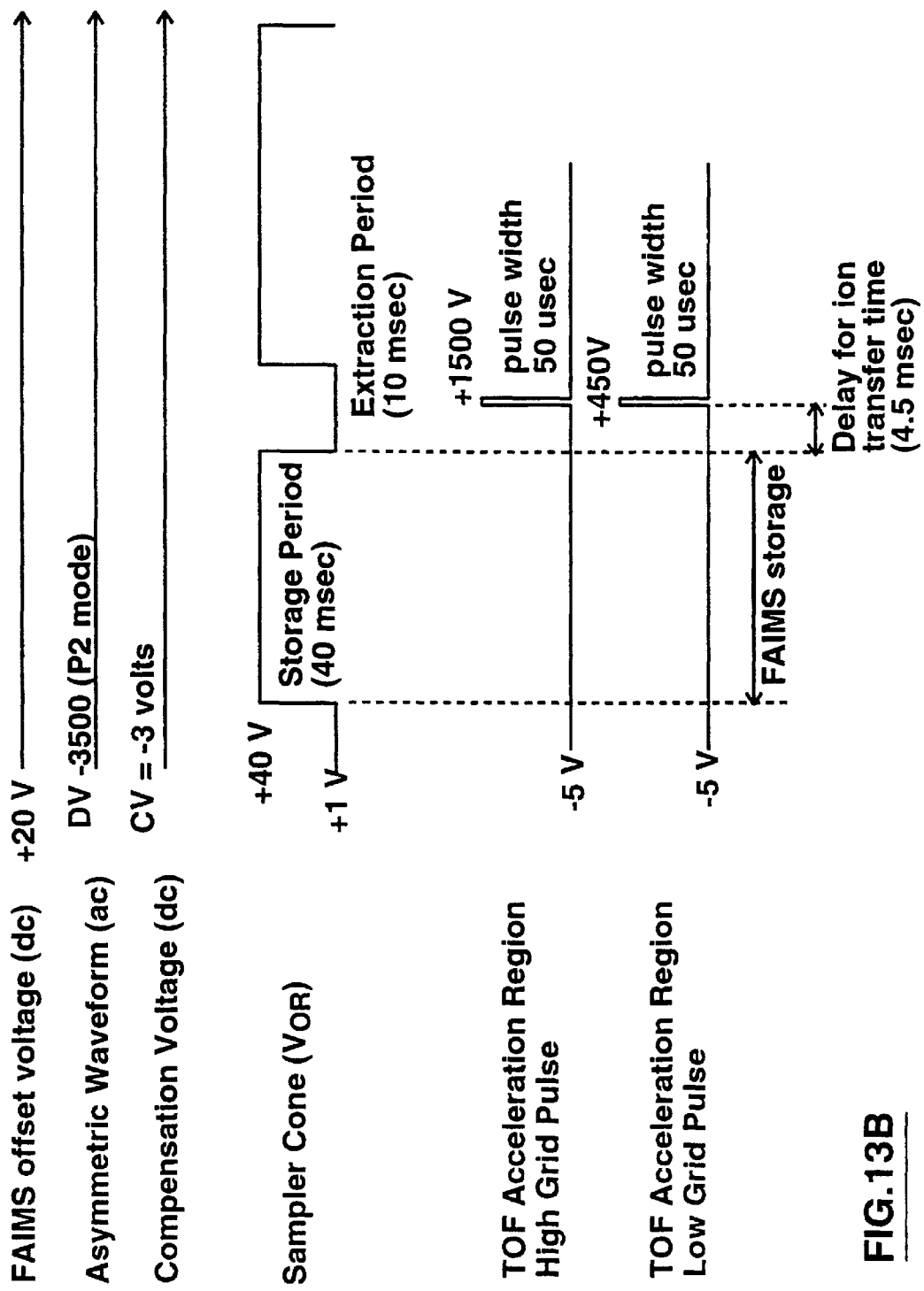
FIG. 13B shows a timing diagram for control of the FAIMS apparatus and the TOF mass spectrometer of FIG. 13A.

Now referring to FIGS. 13A–13J, a system of using a time-of-flight (TOF) mass spectrometer, in conjunction with the FAIMS-R3-prototype 50, is discussed. As shown in FIG. 13A, the assembly of the FAIMS, the ion production, and gas controls are similar to that shown in FIG. 12. For the purposes of further elucidation of the operating details of this system, and the experimental results, the diagram has been extended to show the internal components of the time-of-flight (TOF) mass spectrometer 70 used for this work. The timing diagram for control of the dispersion voltage, compensation voltage, sampler cone voltage $V_{OR}$, and the TOF acceleration pulse appears in FIG. 13B.

FIG. 13A shows that there is an electrical connection to the sampler cone. This electrical connection is used to control the sampler cone voltage $V_{OR}$, the voltage used to gate the ions out of the ion trap. For example, in a typical experiment, the $V_{OR}$ may be set at +40 V during trapping of the ions and at +1 V for ion extraction (e.g., at FAIMS offset voltage +20 V, and compensation voltage −3 V). These voltages would be applied for time periods, for example, 40 ms for trapping and 10 ms for ion extraction. After the initiation of the ion extraction, a cloud of ions, which was located near the terminus 52T of the inner electrode 52, would move towards the sampler cone 18. Because of the electric field between the sampler cone 18 and the FAIMS 50, and the high flow of gas through the sampler cone orifice 18A and into the vacuum system, some ions would be transported into the low pressure (1 torr) region between the sampler cone 18 and the skimmer cone 71. The skimmer 71 is typically held at ground potential. The 1 V difference between the sampler cone 18 and the skimmer 71 is sufficient to draw the ions through the skimmer 71, after which they enter a low pressure region ($9\times10^{-5}$ torr) and are transported to the entrance of the TOF acceleration region 72 via an octopole ion guide 73. The octopole guide 73 is operated at low pressure so that the delay and broadening of the pulse during transport of the pulse through the octopole 73 is minimized. The octopole 73 is typically operated using a DC offset of −4 V, and a 1.2 MHz applied waveform of 700 V (peak-to-peak) to confine the ions. An exit aperture lens of the octopole ion guide (not shown) is held at −5.5 V. The ions pass through the octopole exit lens and through a series of grids which compose the ion acceleration region 72 of the TOF mass spectrometer 70.

Still referring to FIG. 13A, the acceleration region 72 of the TOF is connected to two high voltage pulse generators 74A, 74B, and operates as follows. The device includes 3 fine mesh metal grids 72A, 72B, 72C. The grid 72C which is located closest to the flight tube is held at constant ground potential. The other two grids 72A, 72B are each connected to a high voltage pulse generator 74A, 74B respectively. The grids 72A, 72 Bare found at two possible voltage states, controlled by external pulse generator digital logic 75. In one voltage state both of the grids 72A, 72B are held at one voltage, our experiments used −5.5 V. In this state, the ions that travel from the exit lens of the octopole ion guide 73, will pass through the grids 72A, 72B. The grids 72A, 72B are also held at a second, high voltage condition obtained by applying a pulse (less than 0.1 µs risetime) of about 50 µs duration. There will be some ions which are located in the regions between these grids 72A, 72B when the pulse is applied, and these ions will be accelerated in the direction of the flight tube 76 and the detector 77 shown in FIG. 13A. These ions pass through the second grid 72B and are further accelerated because of the high electric field between the second grid 72B and the third grid 72C, which is at ground potential. Once these ions have passed out of the acceleration region 72, and are travelling along the flight tube 76, the voltages on the two variable grids 72A, 72B in the acceleration region 72 are returned to the low voltage condition, and new ions can enter the space between the grids 72A, 72B. The grids 72A, 72B are typically maintained at high voltage for about 50 $\mu$s.

In principle, the ions which pass down the flight tube 76 separate according to mass (for this discussion, we assume charge (Z)=+1) because all of the ions have the same energy (as a first approximation), defined by the voltage drop between the pulsed voltage grids 72A, 72B and the fixed grounded grid 72C. The ion energy is defined by $E_t = mv^2/2$, therefore ions of different mass, m, hade different ion velocities, v, so that $E_t$, the energy, is constant. The ions arrive at the TOF detector 77 in sequence of ion mass. The lowest mass ions have the highest velocity and arrive at the detector 77 first, and the highest mass ions arrive last.

In practice, however, not the all of the ions leaving the acceleration region 72 have identical voltages. The ions have energy in part dictated by their starting location between the two pulsed acceleration grids. This difference in energy allows the device the capability of 'spatial' focussing, which means that all of the ions with a given m/z, regardless of their starting position in the acceleration region 72, will reach the detector 77 simultaneously. This use of the word 'focussing' in this context is much like the focussing of light in an optical system (e.g., camera). Ions accelerated from between the second grid 72B and the grounded grid 72C have a wide range of energy and contribute to unwanted 'background' noise. This is minimized by locating the second grid 72B very close (2 mm) to the grounded grid 72C.

The TOF acceleration region 72 is pulsed at fixed delay times following the pulse applied to the sampler cone 18 ($V_{OR}$). There will be a finite delay time for the pulse of ions to be extracted from FAIM 50, pass through the vacuum interface 18, 71, thro ugh the octopole 73, and into the acceleration region 72. TOF mass spectra are collected at a series of delay times after the extraction pulse is applied to the sampler cone 18. The arrival of the pulse of ions is characterized by the appearance of a strong, transient signal, followed by a decay of signal intensity down to a constant level which corresponds to the uniform signal which would be detected if the sampler cone was held at the low voltage (i.e., +1 V) state continuously.

TOF Mass Spectra, and CV Spectra for the Study of Ion Trapping

The low mass ions produced by corona discharge ionization, particularly protonated water ions were at very high ion density (abundance), and were therefore expected to either fill the trap too rapidly, or have too short lifetimes for the present study. Therefore, it was decided to look for higher mass ions in P2 mode. The a bundance of these ions were expected to be low since they were only formed from trace contaminants in the carrier gas. No additional sample compounds or gases were added to the system. The ions s tudied here were formed by corona discharge ionization in the "clean" nitrogen atmosphere. The ion source, and the FAIMS device wer e operated in as clean a condition as possible.

Figure 13C:
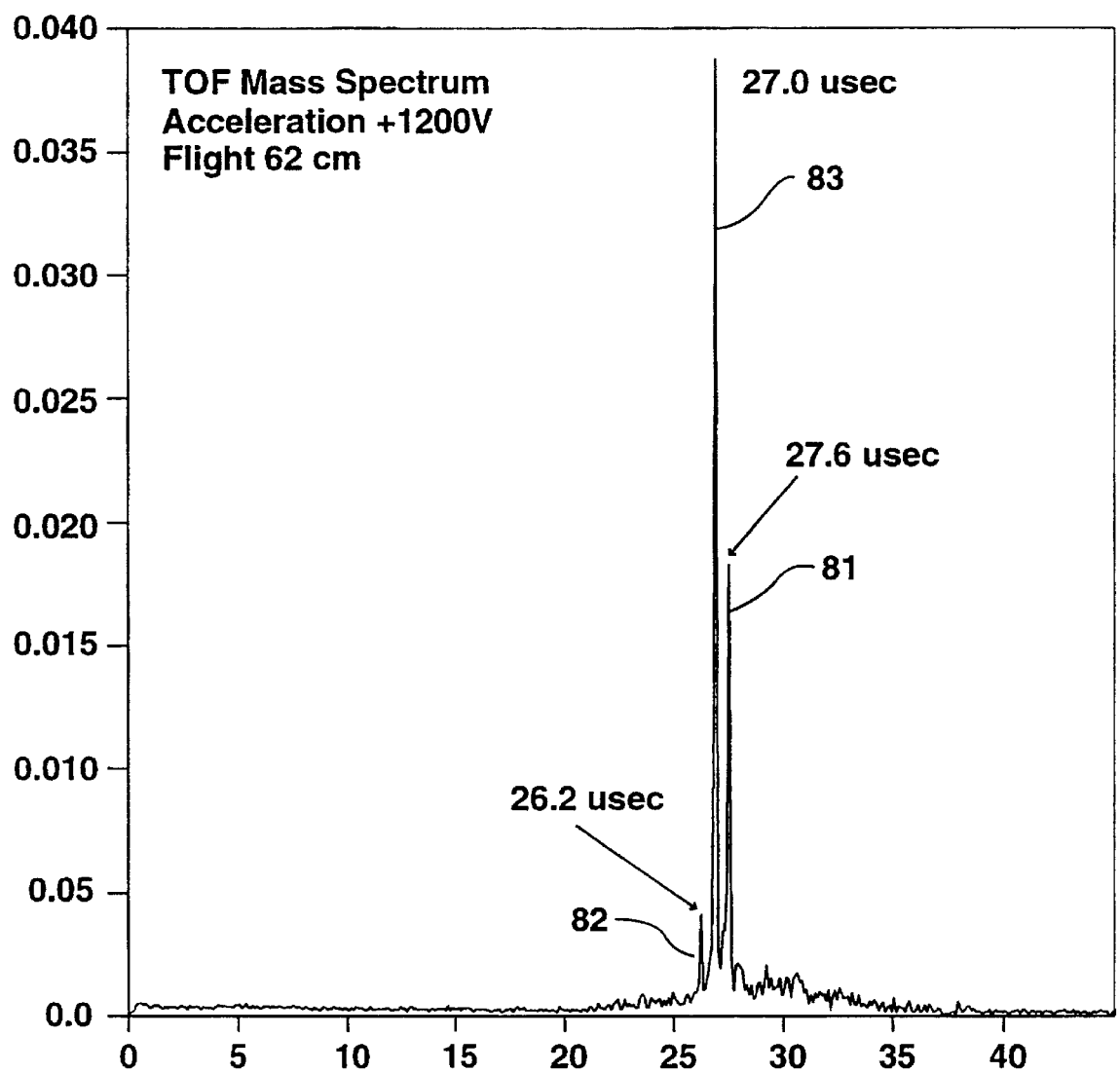
FIG. 13C illustrates a TOF mass spectrum acquired using the system shown in FIG. 13A.

FIG. 13C illustrates a typical mass spectrum acquired for this study. The exact mass was not determined, since this would require a known calibration compound, however the approximate mass was determined using the flight times for some lower mass ions including the protonated water ions. Several impurity ions 81, 82 appear in the spectrum, however only the ion 83 of highest abundance (flight time 27.0 $\mu$s) was considered for the present study. This ion 83 has a m/z of about 380 (±10 m/z).

Figure 13D:
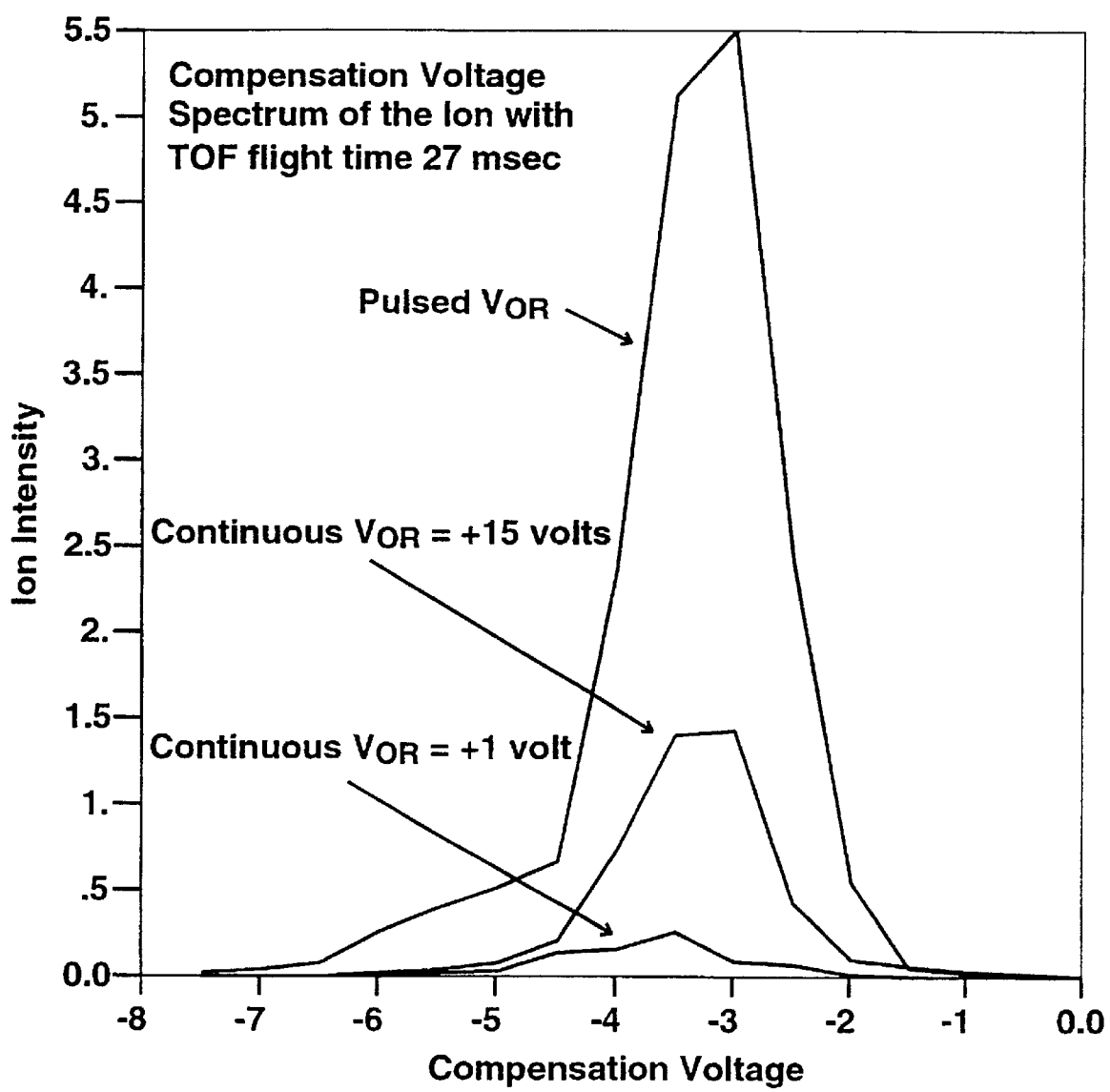
FIG. 13D illustrates a compensation voltage spectrum of an ion with a TOF flight time of 27.0 $\mu$s.

FIG. 13D illustrates the compensation voltage scan for detection of the ion 83 with flight time of 27.0 $\mu$s (m/z about 380) at an applied dispersion voltage of −3500 V. This polarity of DV is referred to as P2 mode, and the ions typically passing through FAIMS in P2 mode usually have mass above m/z 300. The ions that are usually present in P2 mode have ion mobilities that decrease as the electric field increases (ion type C, FIG. 1). One limitation of P2 mode is that the ions are typically found at low CV, and therefore the strength of the ion trapping is weak. On the other hand, one advantage of higher mass ions is that the ion mobility is usually lower, and therefore the distances travelled during the application of the high voltage asymmetric waveform are reduced, and the rate of ion loss to the walls via diffusion is expected to be minimized.

The ion intensity at each experimental point in FIG. 13D was acquired by averaging the spectra recorded from 5000 repeat TOF acceleration pulses. The compensation voltages were adjusted manually, with a digital voltmeter used to read out the voltages set by a power supply. Three traces appear in FIG. 13D, corresponding to the collection of compensation voltage sweeps in three operating methods including: (1) pulsed sampler cone 18 with detection at 4.5 ms after the 'down' edge (transition) of the $V_{OR}$; (2) continuous ion transport from FAIMS through to the TOF with the $V_{OR}$ set at +1 V; and (3) continuous ion transport from FAIMS to the TOF with $V_{OR}$ at +15 V. The compensation voltage corresponding to the maximum detected ion transmission was comparable for these three methods of data acquisition. From FIG. 13D, the ion with flight time 20.0 $\mu$s was transmitted through the FAIMS-device 50 at DV=−3500 V and a compensation voltage between about −2.5 V and −4 V.

Ion Transport Delays within the Ion Optics of the TOF

Figure 13E:
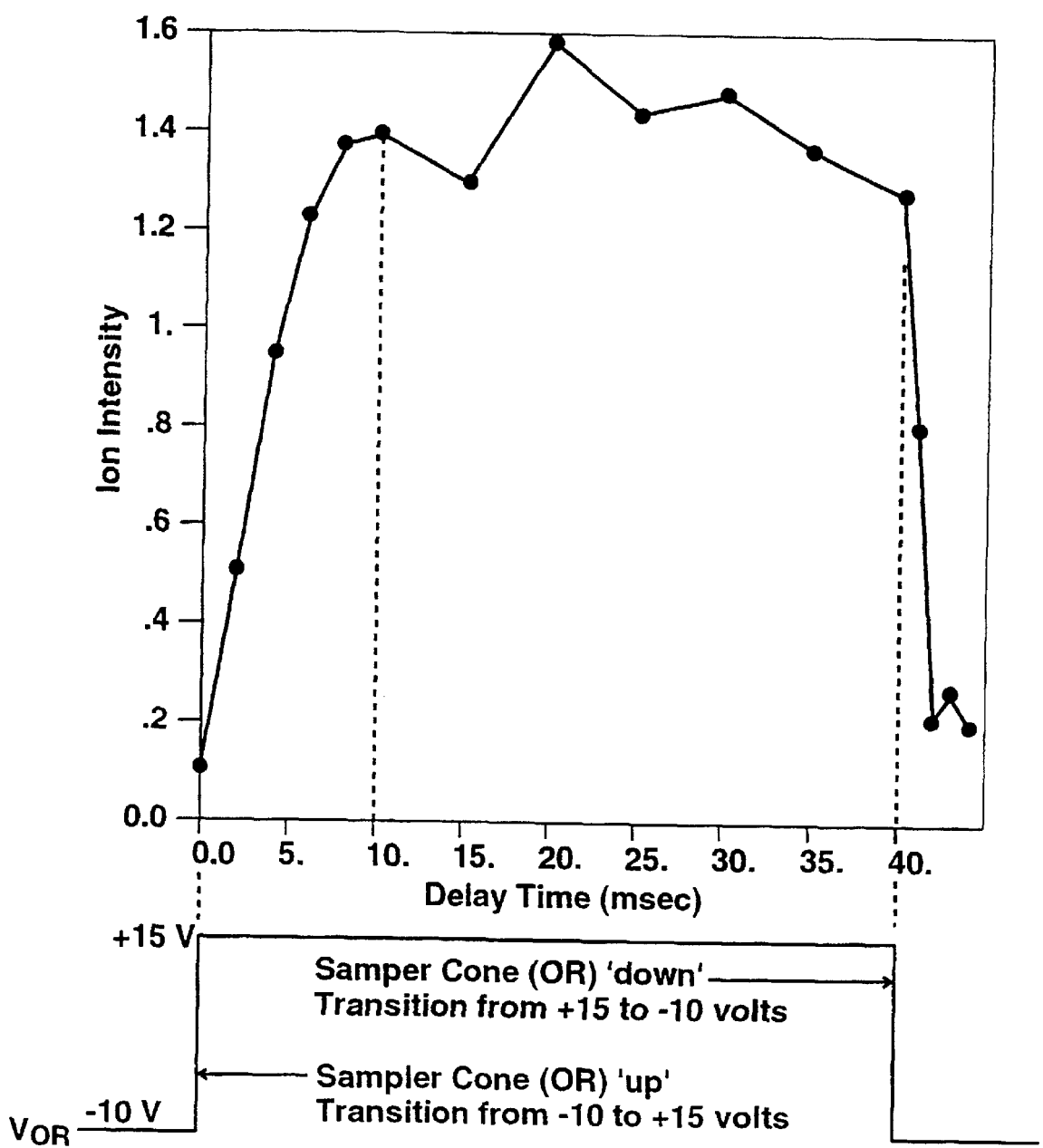
FIG. 13E shows graphically the results of an experiment designed to determine the overall response time of the system shown in FIG. 13A.

Now referring to FIG. 13E, the results of an experiment designed to determine the response time of the entire system are shown. The $V_{OR}$ was stepped between two values, one (+15 V) which was suitable for ion transmission through the FAIMS and into the vacuum system, and the second voltage (−10 V) which was unsuitable for either trapping or ion transmission. FIG. 13E illustrates the intensity of mass spectra collected at a series of time delays between the $V_{OR}$ transitions of both possible types, namely from high to low voltage, and also from low to high voltage. For the discussion below, these transitions will be considered the 'down' and 'up' edges of the change in $V_{OR}$, respectively. The origin of the delay, and the length of delay, is different for the two cases. The reasons are considered next.

In the case of high to low voltage transition, 'down', which occurs at 40 ms in FIG. 13E, the low voltage applied to sampler cone 18 will prevent any (positively charged) ions from passing between the sampler cone 18 (i.e., VOR at −10 V) and the skimmer cone 71 (at 0 V), and thus the "down" transition will create an extremely abrupt decrease in ion flux passing into the octopole ion guide 73. At one extreme it might therefore be expected that the intensity of spectra taken by the TOF might decrease to zero abruptly. Experimentally, the abrupt decrease in ion density will be 'blurred' due to ions moving back into the low ion density region. This broadening is expected: (a) because not every ion will have identical kinetic energy, and those ions with slightly less energy will fall behind, and (b) because collisions between the ions and the residual gas within the octopole housing 73 will affect the kinetic energy of some fraction of the ions. Since the octopole 73 is an ion guide, this longitudinal spreading will be accentuated since ions which have undergone collision with the residual gas will remain contained within the octopole 73. Because of their lowered kinetic energy, these ions will travel through the octopole 73 and arrive at the acceleration region 72 of the TOF with long delay times. FIG. 13E shows that the ions continue to arrive at the TOF acceleration grids for about 2 ms after the $V_{OR}$ is shifted from +15 V down to −10 V. Note that this 'down' transition occurs at 40 ms on FIG. 13E.

The 'up' voltage transition of the sampler cone from low to high voltage has a slightly different effect. This transition occurs at time 0 ms in FIG. 13E. As shown in FIG. 13E, the time required for the intensity of the TOF spectra to reach a plateau is about 10 ms. Several delays are expected. When $V_{OR}$ is raised, the relatively low density of ions which are located in front of the terminus 52T of the inner cylinder 52 of FAIMS 50 must be augmented by newly arriving ions which have been passing along the annular region 54 between the FAIMS cylinders 52, 53. Secondly those ions must start to pass through the sampler cone 18 to the skimmer 71 region, and subsequently through the octopole 73. From the discussion of the 'down' edge of the $V_{OR}$ pulse described above, it requires a minimum of 2 ms for changes in ion density (of the ion which is monitored) to be transmitted through the octopole 73. The additional time delays required prior to ion abundance increases in the TOF spectra (i.e., the difference between 2 ms and 10 ms) are therefore attributed to delays in appearance of ions in front of the sampler cone 18, and secondly due to the transmission through the sampler cone 18 to the skimmer 71 region.

Experimental Verification of Ion Trapping in FAIMS

Figure 13F:
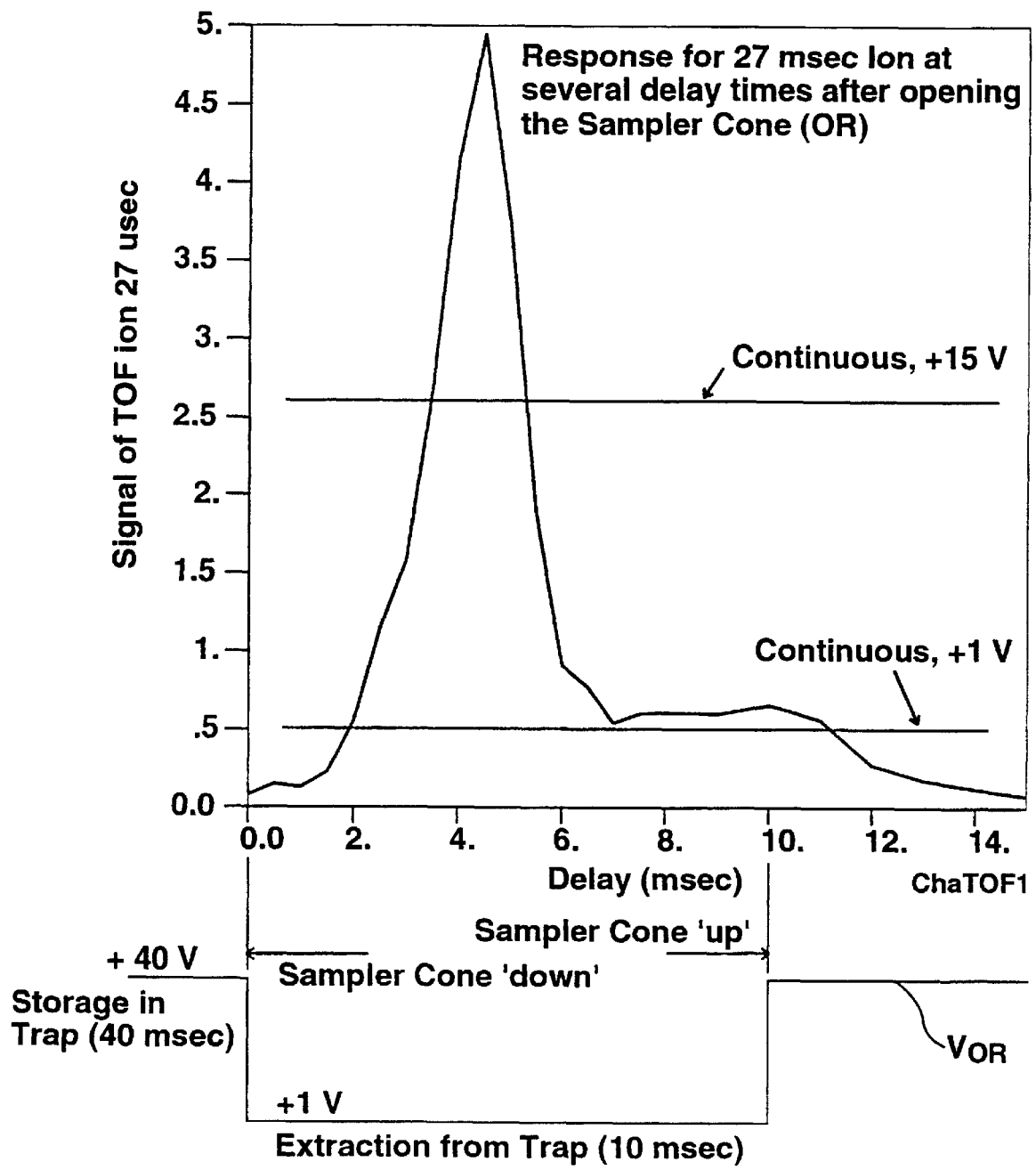
FIGS. 13F and 13G illustrate experimental verification of the 3-dimensional ion trap using the system of FIG. 13A.
Figure 13G:
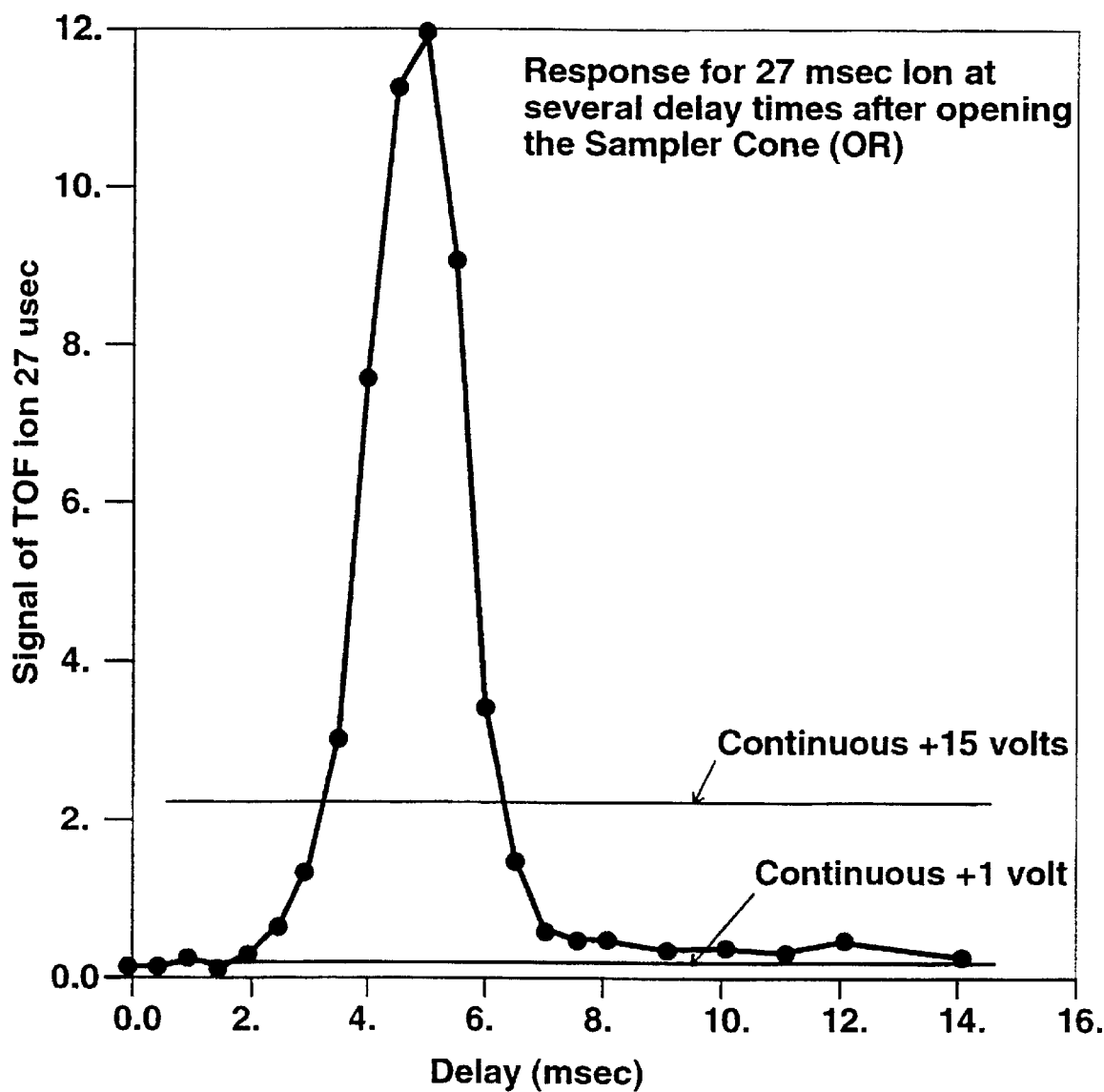

Now referring to FIGS. 13F and 13G, the experimental verification of the 3-dimensional ion trap located near the spherical terminus 52T of the inner electrode 52 of the FAIMS 50 is illustrated. The experimental conditions for collection of the data for FIGS. 13F and 13G were identical, except that the carrier gas flow into FAIMS 50 was decreased for collection of FIG. 13G. The data for these plots were collected in independent experiments, about 1 week apart.

The plots in FIGS. 13F and 13G show the measured intensity of the ion with flight time 27.0 μs (about m/z 380) collected at various times after the 'down' transition of the sampler cone 18. The timing of these pulses is shown at the bottom of FIG. 13F. Time zero represents the time at which the sampler sone 18 is pulsed from the high voltage state ($V_{OR}$+40 V) to its low voltage state ($V_{OR}$=+1 volt), thereby extracting ions from the FAIMS trap. The ions require about 5 ms to travel through the system to the TOF acceleration region 72. The pulse of ions is widened during passage, and appears to be about 3 ms wide (at half height) when detected by the present system.

FIGS. 13F and 13G also include two horizontal lines corresponding to collection of non-pulsing mode data at two different settings of $V_{OR}$. The lower intensity data was collected with $V_{OR}$=+1 V, which corresponds to the 'low' state of the sampler cone 18 when operating in pulsed mode. The higher intensity, horizontal trace, was collected at an experimentally optimized setting for the sampler cone 18 (at $V_{OR}$=+15 V). At this setting the dc level of the sampler cone 18 resulted in the maximum possible TOF spectrum intensity for the non-pulsing mode. Note that the intensity of signals for $V_{OR}$=+15 V for FIGS. 13F and 13G are comparable although the data was collected on different occasions and with different FAIMS gas flow conditions. Ion trajectory modelling has shown that the ions passing around the terminus 52T of the inner electrode 52 can be focused towards the center channel as they pass by the end of the electrode 52. In this way the ions will tend to be transmitted into the sampler cone orifice 18A leading to the vacuum with maximum sensitivity. An example of this trajectory calculation that indicates that this ion focussing will occur is shown in FIGS. 19C and 19D (below).

Ion Storage Time Period

Figure 13H:
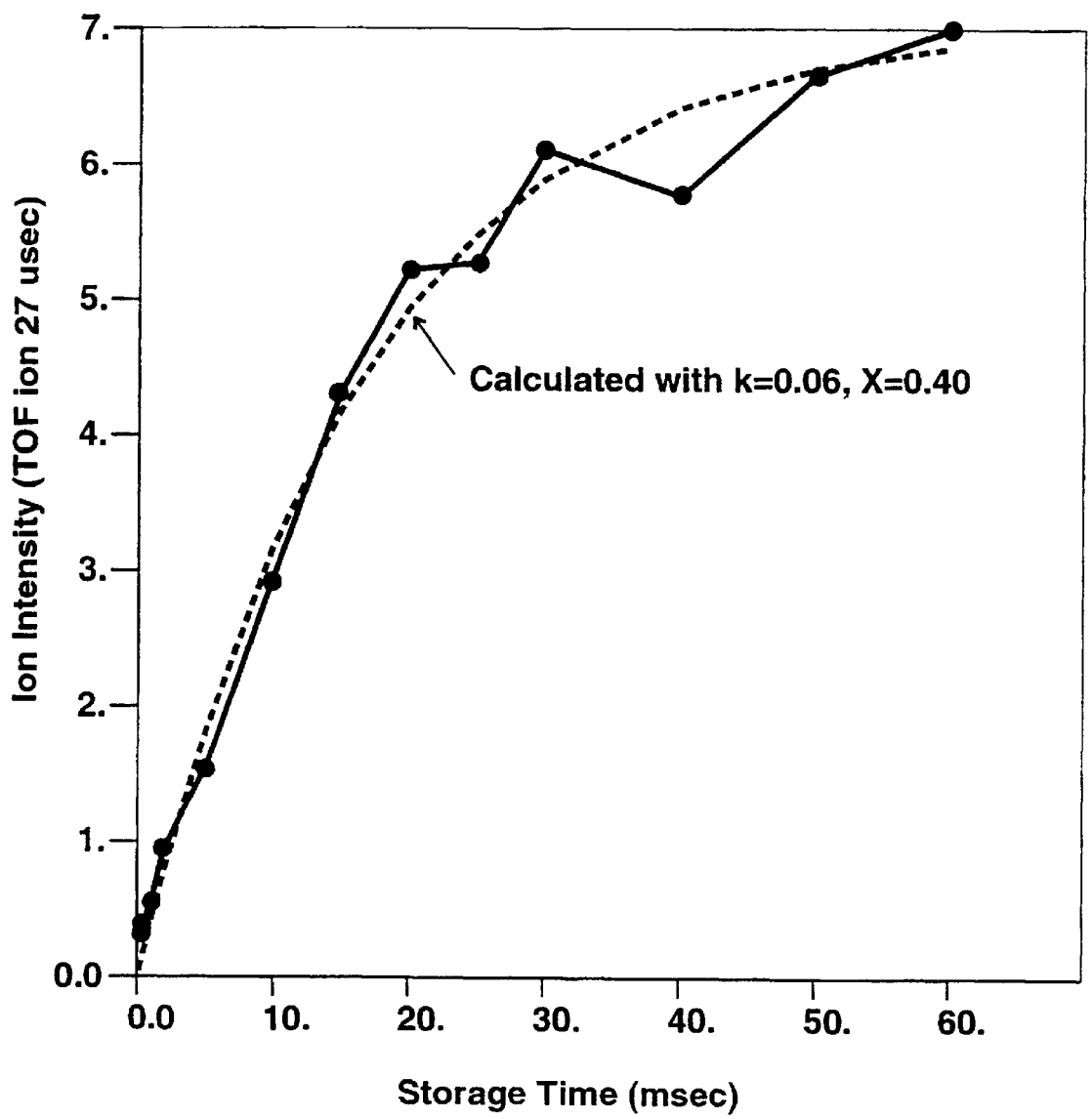
FIGS. 13H, 13I and 13J, show the intensity of the TOF peak for variable ion trapping periods from 1 ms to 60 ms, at three compensation voltages.
Figure 13I:
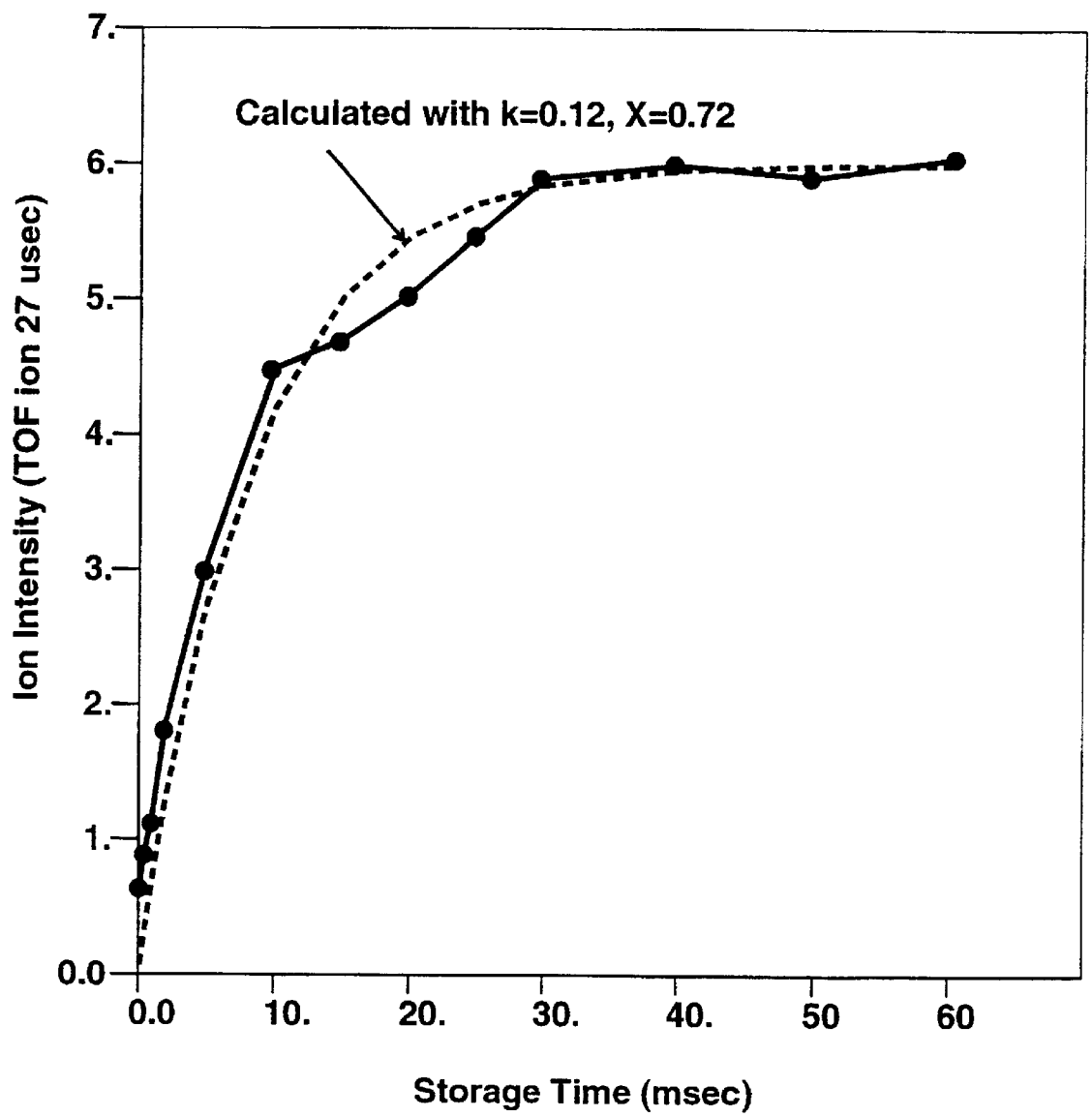
Figure 13J:
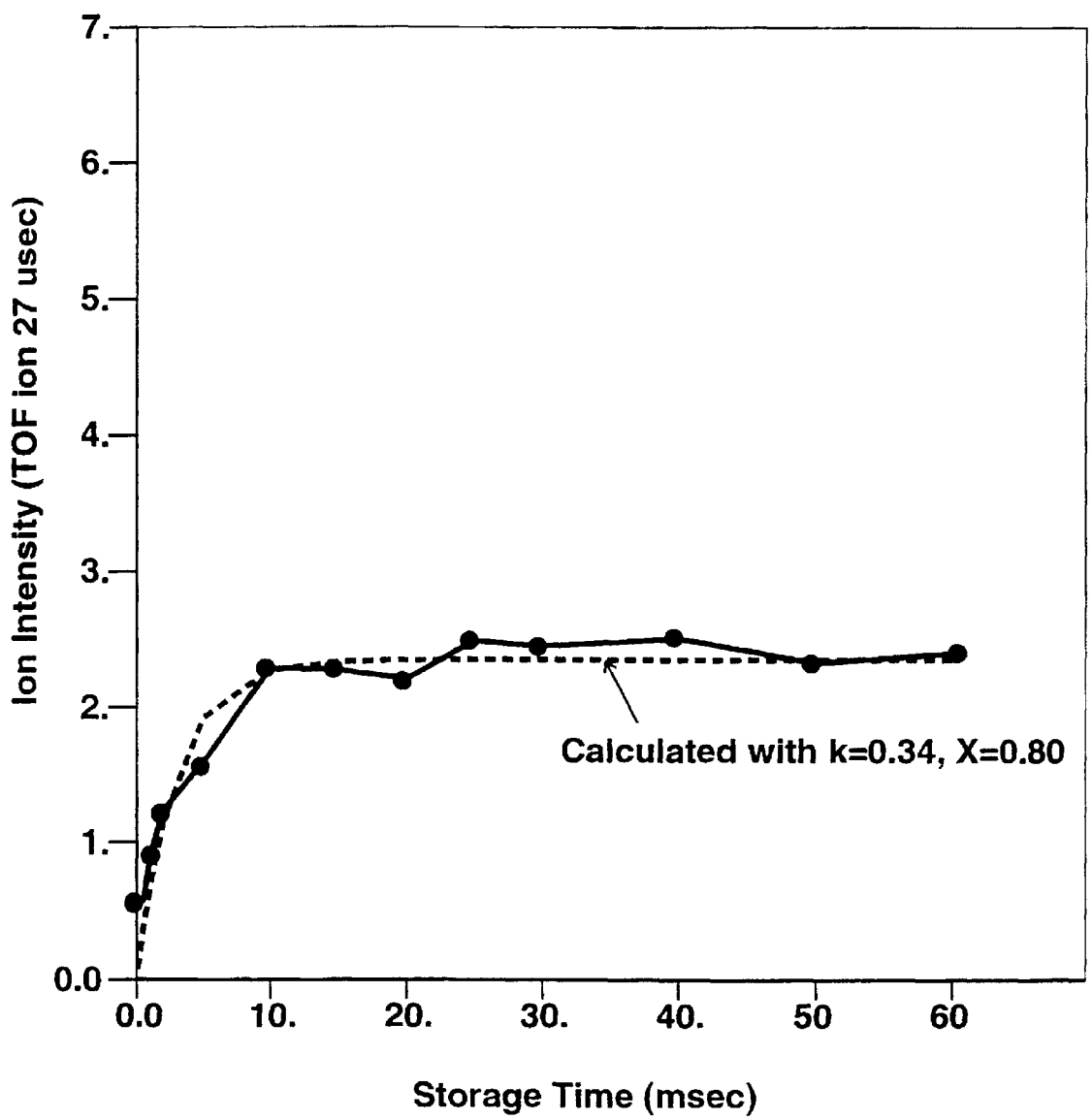

An experiment was performed to determine the effect of the ion storage period on the intensity of the detected pulse of ions resulting from extracting the ions from the storage zone near the end of the inner FAIMS electrode. The intensity of the TOF peak for the ion at flight time 27.0 μs, plotted as a function of the length of the storage time period is shown in FIGS. 13H, 13I and 13J. The waveform applied to the sampler cone 18 was composed of a constant period of time (10 ms) at low voltage ($V_{OR}$=+1 V) during which the ions were permitted to enter the TOF. The signal intensity was measured by activating the TOF acceleration grids 72A, 72B about 4.5 ms after the sampler cone grid voltage $V_{OR}$ was lowered. $V_{OR}$ was held at a high value ($V_{OR}$=+40 V) for periods of time shown on the x-axis of FIGS. 13H–13J. Three traces appear in FIGS. 13H, 13I and 13J, corresponding to data collected at various settings of compensation voltage CV. The ion intensity for a non-optimum compensation voltage, CV=−4 V (FIG. 13J), suggests that the ion trap is relatively inefficient, and the maximum number of ions which can be held in the trap is reached relatively rapidly, i.e., about 10 ms. On the other hand, at CV=−3 V (FIG. 13H) and −3.5 V (FIG. 13I), the intensity rises for over 30 ms. This suggests that the lifetime of the ion, i.e., with drift time 27.0 μs, within the FAIMS ion trap is at least 5 ms. At high trapping times it is assumed that the trap has filled and that the influx of ions is balanced by losses by diffusion and gas flows. This experiment can be considered to be a simple kinetics problem. The influx of ions is X ions/sec. The loss of ions, Y ions/sec, is proportional to the number of ions in the trap. The increase in the number of ions in the trap, Z ions total, will continue until steady state is reached and X=Y=kZ, where k is the rate constant for the function describing the rate of ion loss from the trap. At a short delay time Z is small and kZ is small. It therefore can be assumed that Z=Xt where t is the time. The solution to the differential equation dZ/dt=X−kZ is $Z(t)=X(1-e^{-kt})/k$, if Z at time zero is zero. The data set can be fit to this function to determine X and k. FIGS. 13H, 13I and 13J show the experimental data, and calculated curves based on the equation above used to fit the data. The k values were 0.06, 0.12 and 0.34 for the CV curves −3, −3.5 and −4 V respectively. The corresponding X values were 0.4, 0.72 and 0.8 respectively. High values of k represent conditions wherein the rate of ion loss is high. High values of X correspond to a high rate of ion input into the trap.

FAIMS-R4-prototype

Figure 14A:
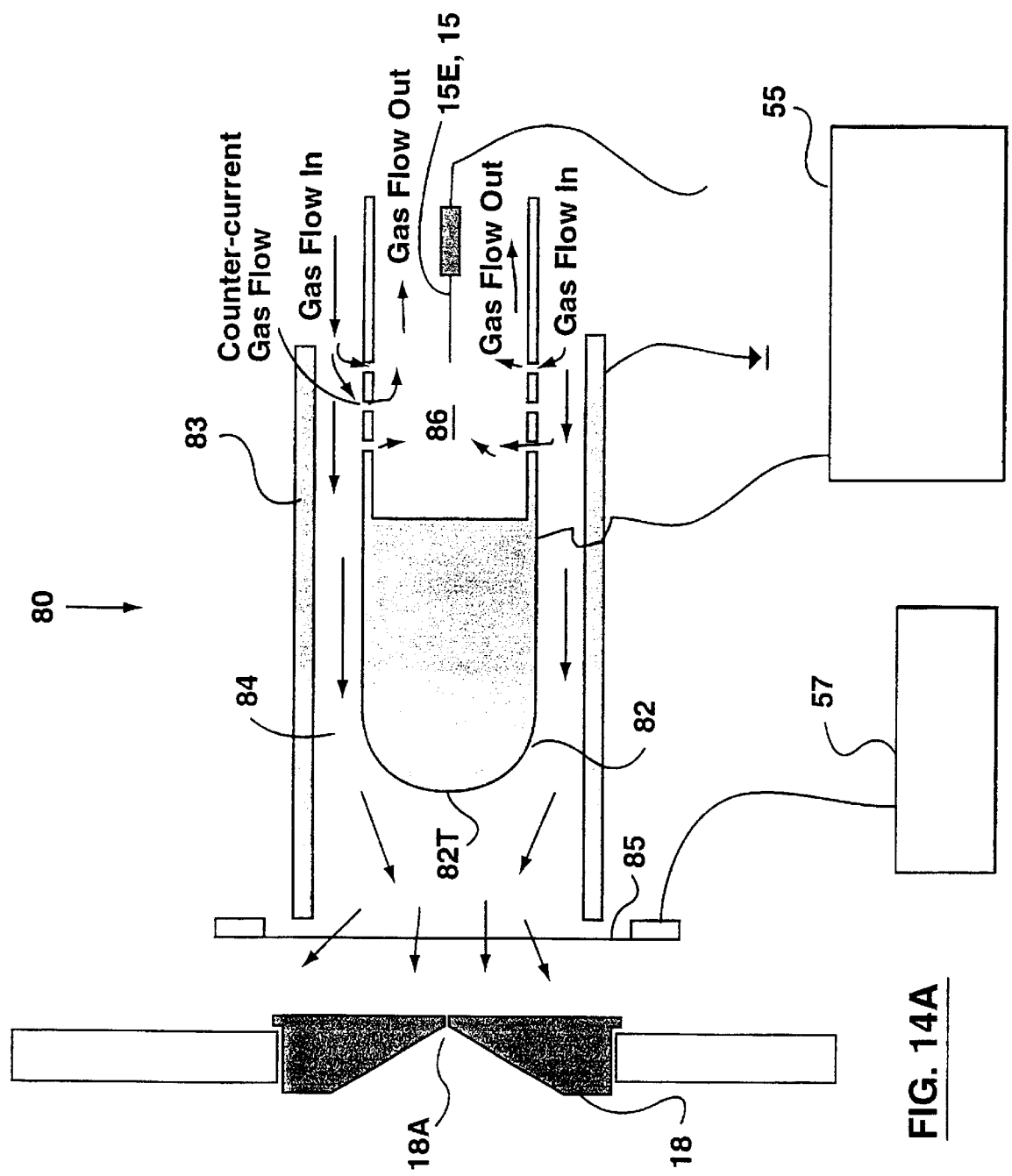
FIGS. 14A–14C show schematically an alternative embodiment of a 3-dimensional atmospheric pressure high field asymmetric waveform ion trap.
Figure 14B:
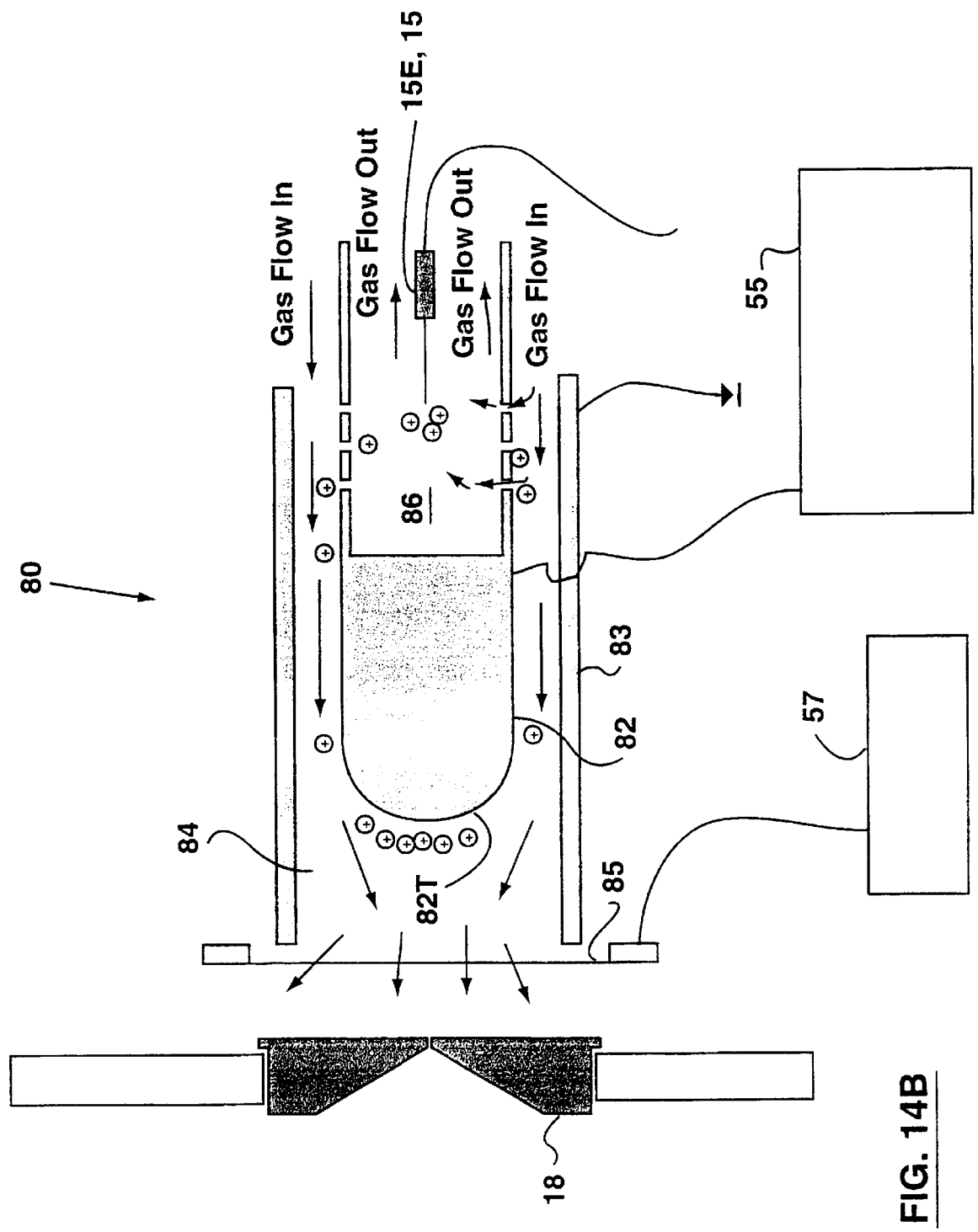
Figure 14C:
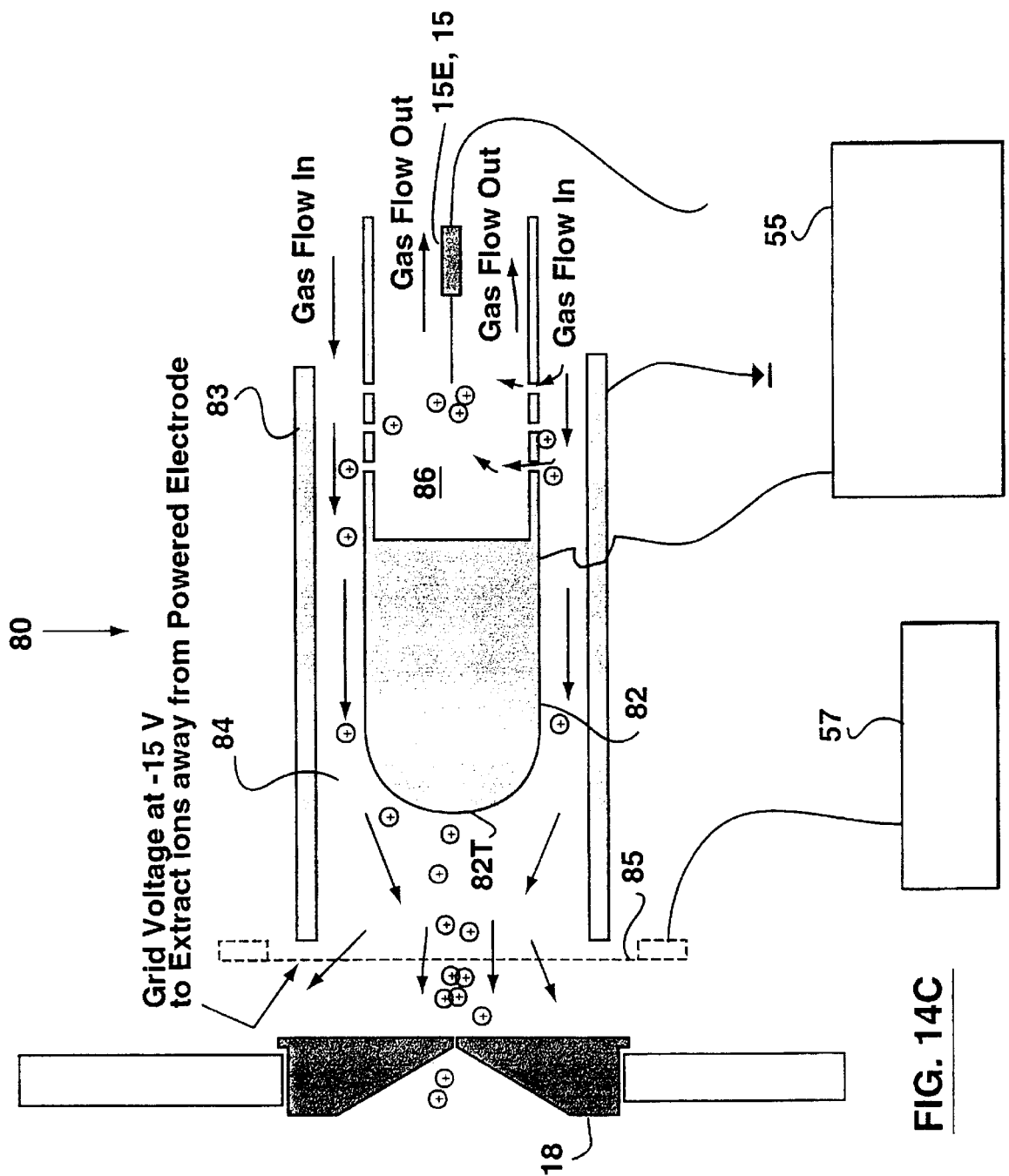

Now referring to an alternative embodiment shown in FIGS. 14A–14C, referred to as FAIMS-R4-prototype 80, a FAIMS 3-dimensional atmospheric pressure ion trap is shown in which the electrospray (or other ionization) occurs within the radius of the inner electrode 82. This is the configuration preferred in the Mine Safety Appliances Company version of the FAIMS. A modified version of this device is shown schematically in FIGS. 3A and 3B. In general, ions may be introduced to the FAIMS analyzer region 84 either from outside (external) to the outer electrode 83, or from inside (internal) the inner electrode 82. The latter is less convenient because the dimensions are small, and the radius of the inner electrode 82 must be much larger than can be used in devices using the external ion source. Moreover, the ionization source (e.g. corona discharge needle) may be susceptible to the influence of the high voltages applied in the asymmetric waveform. The electrode immediately surrounding the ion source is electrically grounded in the FAIMS shown schematically in FIGS. 3A and 3B.

In the device shown in FIGS. 14A–14C, the inner electrode 82 would be about 14 mm outer diameter, and the outer electrode 83 about 18 mm inner diameter, with about 2 mm annular space (FAIMS analyzer region 84) between these two concentric cylinders 82, 83. The end of the inner cylinder 82T (left end in FIGS. 14A–14C) is closed, and shaped as appropriate to maintain the electric fields suitable for FAIMS ion trapping in all locations near the end of the electrode 82T.

The inside of the outer cylinder electrode 83 is shown to be uniform in diameter in FIGS. 14A–14C, but with wide diameter inner electrodes 82 such as shown in FIGS. 14A–14C, it is very likely that the FAIMS analysis conditions will be better maintained if the inner surface of the outer electrode 83 is contoured very much like that shown in FIGS. 9A and 9B. This will maintain substantially constant distance between the inner electrode 82, and the outer electrode 83 near the spherically shaped (or conical etc.), closed end 82T of the inner electrode 82. While the spacing between the inner and outer electrodes near the end of the electrode 82T may be substantially uniform, it will be understood that the spacing may also be non-uniform, as long as equilibrium conditions can be maintained at loations near the end of the electrde 82T.

Gas flows enter the end of the FAIMS analyzer region 84 shown in FIGS. 14A–14C (right hand side of the FAIMS in the figure), and flow toward the closed end or terminus 82T of the inner electrode 82. Beyond the terminus 82T of the inner electrode 82 the gas flow passes through an exit grid 85 comprising a high transparency, fine-wire grid, and exits through the space between the mass spectrometer sampler cone 18 and the exit grid 85. A portion of the gas flows into the orifice of the sampler cone 18, drawn by the vacuum of the mass spectrometer. Some of the ions which have passed through the exit grid 85 during the extraction time period will also be drawn into the mass spectrometer, by gas flows and by electrical fields.

Some of the gas entering the FAIMS analyzer region 84 shown in FIGS. 14A–14C must be permitted to flow inwards (i.e. the counter current gas flow) from the analyzer region 84 into the ionization region 86, thereby preventing neutral molecules, large liquid droplets and other unwanted non-charged components from passing into the FAIMS analyzer region 84. These components would contaminate the gas in the FAIMS analyzer region 84, and the ion focussing and trapping described elsewhere in this document may be degraded. The device therefore may fail if the gas flow from the FAIMS analyzer into the ionization region is reversed during electrospray experiments. If the ionization occurs in a very clean non-contaminated gas, then this restriction on the gas flow direction may be relaxed (e.g. ionization of clean gas with radioactive $^{63}$Ni foil, corona discharge ionization, ionization by UV light radiation etc.). During operation in P2 mode the requirement for high purity gas is somewhat relaxed.

The device shown in FIGS. 14A–14C operates in a manner analogous to that described previously. The ions pass radially out of the ionization region 86, transported by electric fields against the radially inward flowing gas. Having passed into the FAIMS analyzer region 84 the electric fields will either confine the ions inside the analyzer region 84 (focussing or trapping) or the ions, because of application of DV and CV which are not appropriate, will collide with the walls of the device. Assuming that the DV and CV are appropriate for one of the ions in the sample, that ion will be focused in the FAIMS analyzer region 84, and flow with the gas (since in the FAIMS analyzer region 84 the gas and electric fields act perpendicularly to each other) toward the closed, dome-shaped terminus 82T of the inner electrode 82. If the trapping fields (electrical potential well) remain appropriate, the ions will assemble near the terminus 82T of the inner electrode 82 as shown in FIG. 14B. This will occur because the ions cannot return toward the ion source against the flow of gas, and the ions cannot flow with the gas out of the grid 85 because of the confining action of the electric fields near the terminus 82T of the inner electrode. As long as the following conditions are maintained, this trap will exist: (1) the DV and CV must be applied, and the voltages remain appropriate for the ion being trapped; (2) the voltages on the outer electrode and the grid remain fixed, e.g. near 0 V, as appropriate for the ion being trapped; and (3) the gas flow is maintained. If any condition changes the ions may leave the trap. If it is desired to have the ions travel to the sampler cone 18 of the mass spectrometer after passing out of the trapping region, and through the grid 85 as shown in FIG. 14C, then one of the above conditions may be optionally changed to achieve this result. This could occur in a number of ways:

(1) The grid 85 voltage may be lowered (from its value during trapping) relative to the inner electrode 82, and relative to the outer electrode 83. This will have the effect of attracting (positively charged ions) away from the FAIMS trapping region (near the terminus 82T), and thereby breaking the hold of the trap. The ions will leave the trap, and travel toward the grid 85. Some ions will strike the grid wires, and some will travel through (assisted by the gas flow). Since all of the voltages in the device must be considered relative to each other, the same effect can be achieved by changes in the voltages applied to the outer electrode 83, and to the inner electrode 82. For example, an increase in voltage applied to both the outer electrode 83 and to the inner electrode 82, will have exactly the same effect as a decrease in the voltage applied to the grid 85.

(2) The DV or CV can be changed in many ways which alter the ion motion in the vicinity of the FAIMS trapping region. If the CV is made more negative the ions (positive ions) will tend to collide with the inner electrode 82, and if the CV is more positive the ions will be positioned farther from the inner electrode 82, and at some voltage the FAIMS trap will no longer exist for this ion and the ion will travel with the gas flow and under the influence of the average dc electric field, to the grid 85, as noted in (1) above. If DV is removed the trap will no longer function. If CV is altered, e.g. more positive, and DV is removed, (positively charged) ions will be repelled from the inner electrode 82, and may travel to the grid 85.

(3) The gas flow can be changed. If the gas flow is sufficiently high to overcome the trapping action of the electric fields near the closed end of the inner electrode 82T, the ions will be pushed out of the trap and toward the grid 85, as described above. If the gas flow is decreased, or stopped, the ions will move via diffusion, and via chemical changes. The diffusion will permit the ions to return back toward the ion source, thereby de-populating the FAIMS trapping region near the terminus 82T of the inner electrode 82. Even in the presence of gas flows the ions may soon de-populate the trap because of chemical effects. If the ion collides with a neutral molecule and temporarily forms a stable complex, this complex may drift out of the FAIMS trapping region because this new complex has high field mobility properties which were different from the original ion.

Other Versions of FAIMS-Rx-prototypes

The primary objective of the atmospheric pressure FAIMS ion trap is to collect, confine and increase the concentration of ions in some location in space. This can be achieved using the devices described in the paragraphs above. Several simple variations on these devices can be visualized.

(1) The geometry of the end of the inner electrode has been assumed to be spherical, but the surface may be conical, or some variation on these shapes. The shape will be selected to establish the non-uniform electric fields which are necessary to create the FAIMS focussing of ions and FAIMS trapping of ions that is described above.

(2) The geometry of the inside of the outer electrode may be varied. Most of the examples shown have simple cylindrical geometry, for ease in mechanical fabrication. A non uniform surface is more difficult to fabricate, but will be advantageous in some cases, especially if the inner electrode has an outer diameter in excess of approximately 4 mm.

(3) The inner and outer electrodes have been shown to have walls that are parallel to the central longitudinal axis, but this is not essential. The inner electrode may have an outer diameter which varies linearly or non-linearly along its length. The outer electrode may have an inner diameter which varies along its length. This will be advantageous in those geometries in which the ionization source is located within the radial distance of the inner electrode, for example, as shown in FIGS. 3A, 3B, 14A, 14B and 14C.

(4) The gas flows shown in the devices illustrated in this document serve two independent and identifiable purposes. First, the gas flow serves to carry the ions along the length of the FAIMS analyzer region since the electric fields are acting perpendicularly to the length of the region, and therefore cannot help to transport the ions along the length of the device. Secondly the gas flows are always arranged to maintain the FAIMS analyzer and FAIMS trapping regions clean, and relatively free of gas phase water and chemical contaminants. Where possible, the ions must travel upstream, counter-current, to the flowing gas prior to entering the FAIMS analyzer region, in order to avoid entrance of neutrals and droplets into the FAIMS analyzer region. The embodiments of the atmospheric pressure, 3-dimensional ion traps that have been described above may permit the replacement of one or another function of the gas flow. For example, the transport of ions along the length of the FAIMS could be accomplished via electrical means. For example, if an electrical gradient is established along the length of the FAIMS analyzer which will serve to carry the ions along its length, this would replace one of the functions of the gas flow noted above. The electrical gradient can be created in two ways. First, the inner and/or outer electrodes can be segmented, with a slightly different constant, dc, voltage applied to each segment in such a way as to create another voltage gradient from one end of the device to the other. This is entirely feasible if the device can simultaneously maintain the DV and CV and geometric conditions which are necessary to maintain the ion focussing or trapping conditions. Secondly, one or more of the electrodes may be fabricated in such a way as to permit a voltage gradient to be established along the length of the device. The has been accomplished using insulating electrodes coated with a semiconductive layer. If a different voltage is applied to each end of such an electrode, the electrode acts like a resistive device, and the voltage gradient sits along its length. The voltage gradient can be linear, or non-linear depending on the application of the semi-conducting layer. The methods for ion motion modelling described below permit evaluation of such approaches without construction of prototypes. Modelling has shown that these devices are feasible.

(5) The electrode to which the asymmetric waveform is applied has in most cases been the so-called "inner electrode" in the discussion above. The "outer electrode" surrounds the inner electrode, and is usually held at $V_{FAIMS}$. As explained earlier, in one case (FIGS. 6A and 6B), the asymmetric waveform was applied to the "outer electrode". There is no theoretical reason for applying the DV and/or CV to the inner electrode. In all of the configurations described in this disclosure, it is possible to apply the asymmetric waveform and/or the offset CV to either the inner or outer electrodes. In some cases, including the case illustrated in FIGS. 14A–14C, there is significant advantage to application of the waveform to the outer electrode.

(6) DV and CV need not be applied to the same electrode. For example in order to achieve a CV of –11 V, the –11 V is either applied to the inner electrode, or +11 V is applied to the outer electrode. Exactly the same logic applies to DV. If a condition for trapping an ion requires DV 2500 V (applied to the inner electrode), then exactly the same behavior can be expected when DV –2500 V is applied to the outer electrode. As was discussed in the text describing the hardware shown in FIGS. 6A and 6B, it was understood that these changes in voltage polarity are required, therefore the text for FIGS. 6A and 6B was simplified and the polarity was described as if the waveform DV and CV was applied to the inner electrode. This was done to simplify comparisons amongst the devices described in other sections.

(7) The geometry of the mass spectrometer sampler cone has not been discussed. The sampler cone 18 shown in FIGS. 11A–11C for example has been drawn (for simplicity) as flat on the side facing the FAIMS device. There is some advantage to be gained by use of a sampler cone which has a raised (pointed) front surface, with the orifice itself at the apex of the cone. The ions are generally attracted toward the pointed surface, and the ion transmission across the space between the grid, and through the orifice may be improved.

(8) The applied asymmetric waveform may be operated with small transient changes in voltage, phase shifts, and polarity. For example, if an ion is focused or trapped with DV 2500 V, and CV –11 V in a certain geometry, short (ms) changes of DV will affect the capability for ion separations. The voltage of DV may be changed for millisecond periods, the polarity reversed for millisecond periods, and the relative time periods of high and low voltage can be changed for small periods of time. This will create conditions whereby ions which are focused or trapped in a marginal way will be rejected from the FAIMS. For example, two ions which have almost the same high field ion mobility properties, my co-exist in the FAIMS analyzer region or the FAIMS trapping region. Unless steps are taken to selectively remove one of the ions, both will reach the detector (electrometer or mass spectrometer). Small voltage changes to DV or CV, and transient changes in voltages and phases of the waveform may help to eject one of the ions.

(9) The exit grid electrode can take many forms, and in some cases may not be necessary. The exit grid electrode serves 3 functions, including (1) completing the electric fields around the inner electrode, so that the ion trap is formed, (2) forming the electrode described in (1) but simultaneously permitting the gas flow to pass through this region substantially unimpeded and (3) allowing a mechanism by which to form, and destroy the trap without modification to the voltages applied to the inner electrode. Clearly these functions can be carried out by other parts of the device. For example in FIG. 9, the ion trap is controlled via the voltages applied to the inner electrode. The extraction voltage used to eliminate the ion trap may be applied to the outer electrode, or to the inner electrode. Moreover, the grid can be totally eliminated if the sampler cone of the mass spectrometer is placed substantially near the end of the outer cylindrical of the FAIMS. This is the case shown in FIG. 13.

Figure 15:
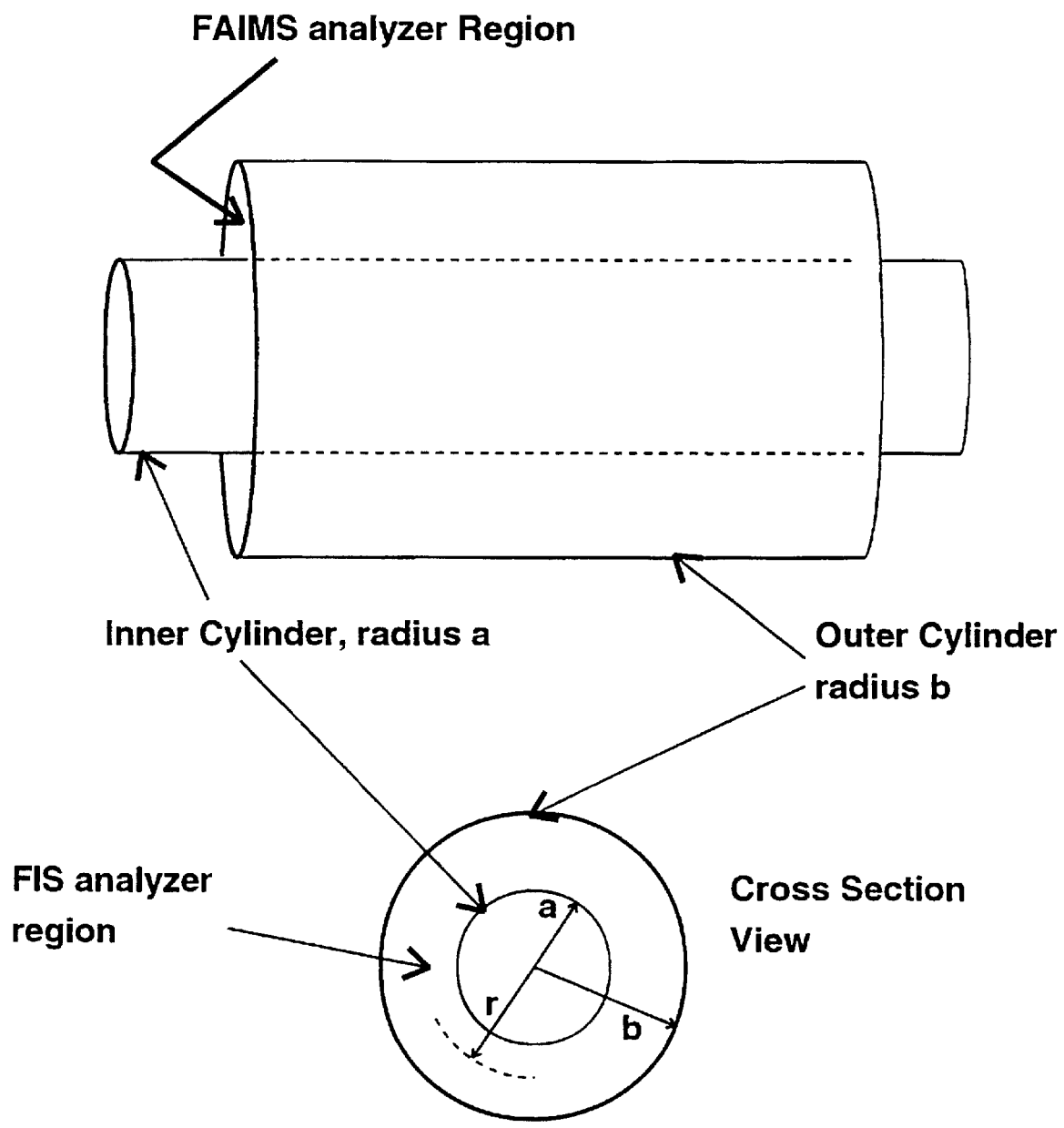
FIG. 15 shows the relevant dimensions of a FAIMS apparatus required for calculation of the voltage within the FAIMS analyzer region.

Modelling the Ion Motion in the FAIMS-E, FAIMS-MS, 2-dimensional and 3-dimensional Ion Traps The ion motion in the FAIMS was modeled using a combination of experimental and theoretical considerations. First, consider the two cylinders used in FAIMS shown in FIG. 15. When a voltage is applied to the inner cylinder, the voltage at any point between the two cylinders can be calculated using the following formula: $V_r=V (\ln(r/b)/\ln(a/b))$ where $V_r$ is the potential at radial distance r (assuming that r falls in the space between the two cylinders), V is the potential applied to the inner electrode, the outer diameter of the inner cylinder is "a" (cm), and the inner diameter of the outer cylinder is "b" (cm). The outer electrode is electrically grounded, i.e. 0 V applied. The annular space (called the FAIMS analyzer region) falls in the radial distance between a and b. This is shown in FIG. 15. The voltage between the tubes is not linear, and the electric field (which is the derivative of the voltage i.e. dV/dr) is also non-linear. The electric field between the tubes (at location r) can be shown to be: $E=-V (1/(r \ln (a/b))$ where E is the electric field (V/cm) and V is the voltage applied to the inner electrode, while the outer electrode is at 0 V. Variables a and b (cm) are defined above, and shown in FIG. 15.

The motion of an ion in an electric field at atmospheric pressure is described by: v=KE where v is the ion driftvelocity (cm/sec) and E is the electric field (V/cm). The "constant" of proportionality for a given set of conditions is called the "ion mobility constant" K. Note however that many changes in conditions can change the value of K. The obvious conditions that change the velocity of an ion in an electric field include: (1) temperature and (2) gas pressure. As discussed above, K also varies with the electric field.

Figure 16:
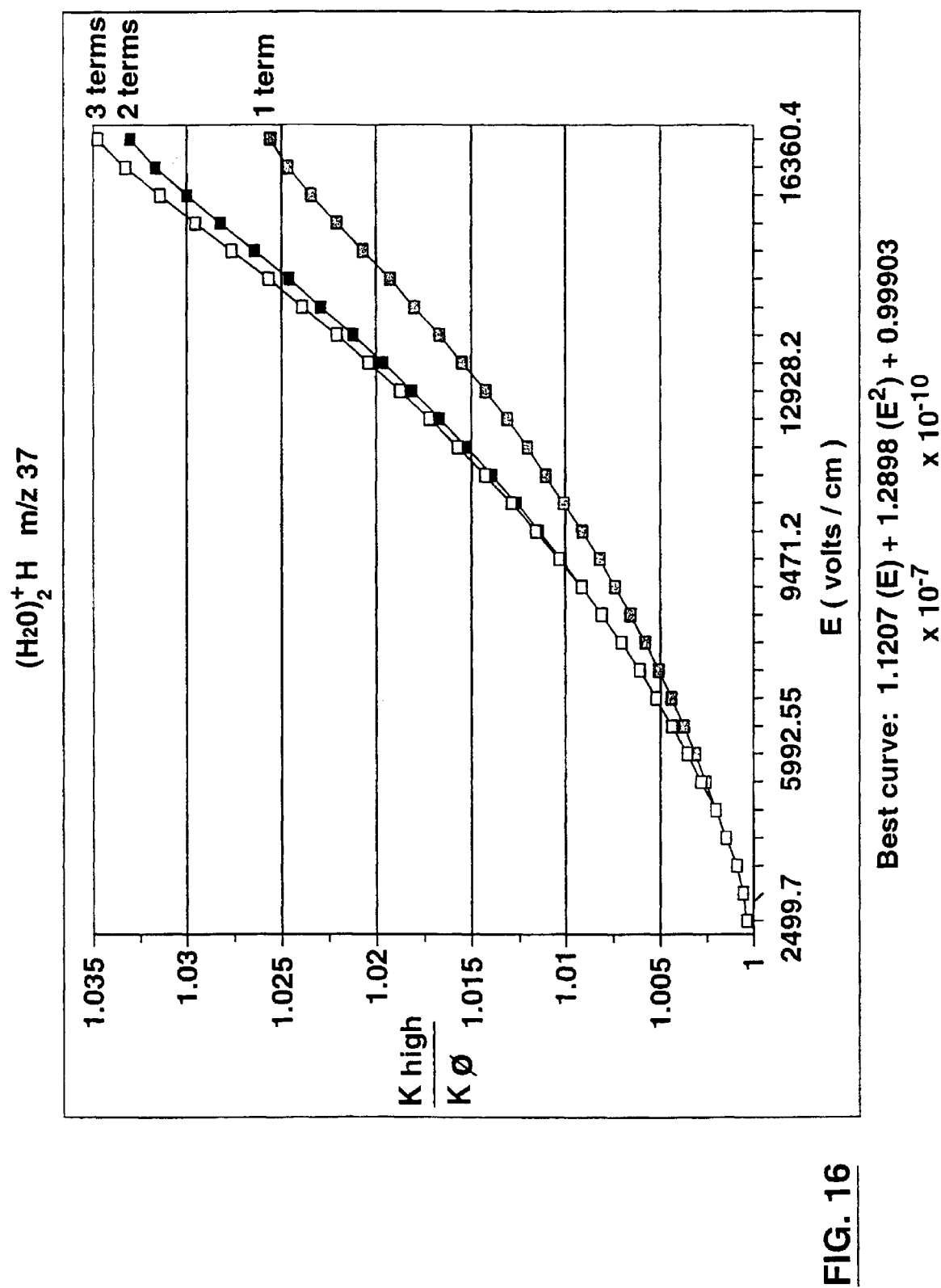
FIG. 16 shows the change in the $K_h/K$ ratio for $(H_2O)_nH^+$ as a function of electric field E.
Figure 17:
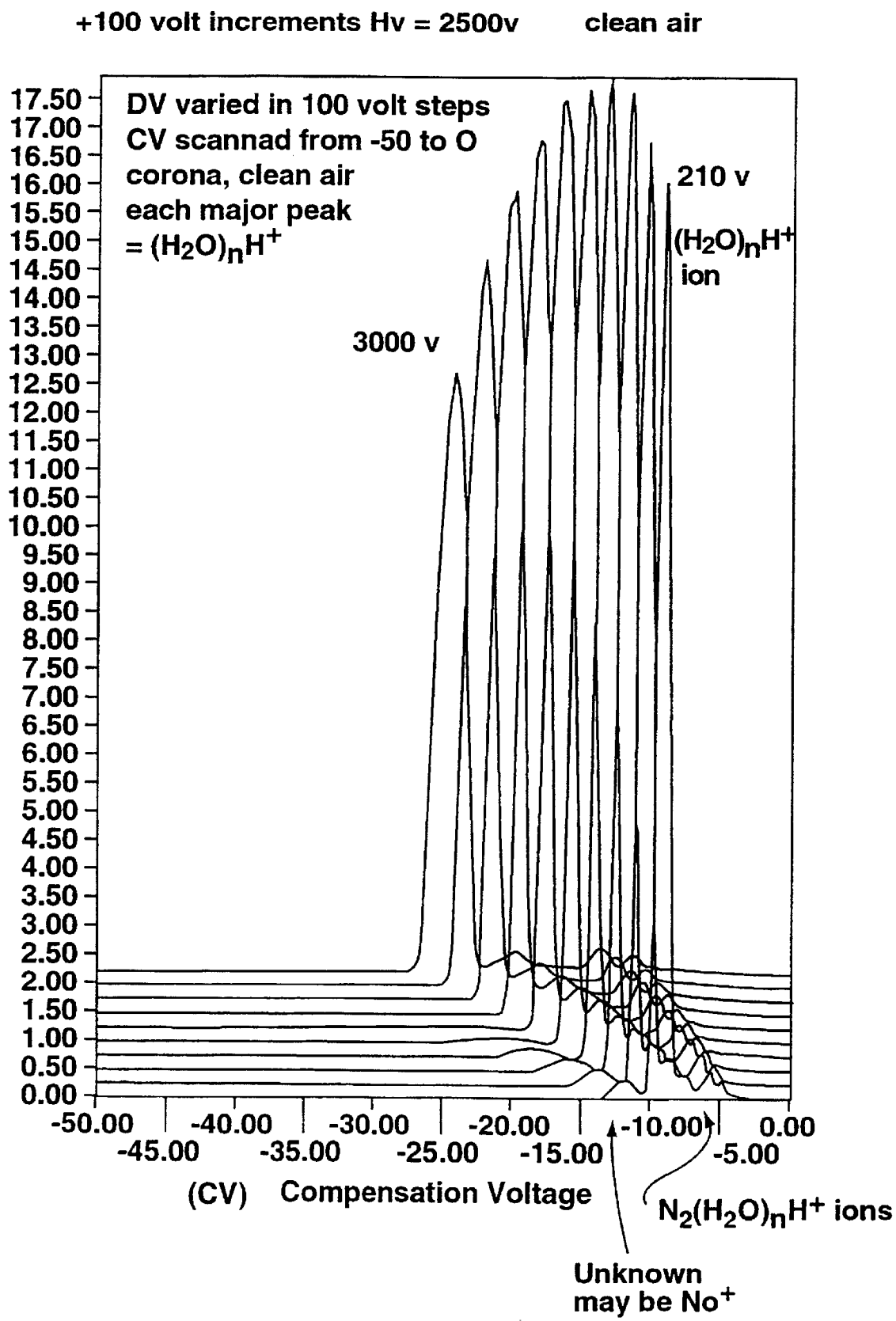
FIG. 17 provides a portion of the original data that was used to calculate the high field mobility $K_h$ of $(H_2O)_nH^+$.

Although it will not be shown here, the ion mobility at high field (called $K_h$ in the discussion above) can be estimated using the modified FAIMS-E 10 instrument shown in FIGS. 3A and 3B. FIG. 16 shows the change in ion mobility of one type of ion, $(H_2O)_nH^+$, at high electric field. The word "terms" in FIG. 16 refers to the cyclic refinement of correction factors for the ion mobility during the low field portion of the asymmetric waveform. In practice, during a waveform (e.g. FIG. 4) at DV 3000 V, the low voltage portion of the waveform is at about −3000/2 or −1500 V. Even at this lower voltage, the electric field is sufficiently high that the ion mobility cannot be assumed to be at it's "low field" value that is shown at the left axis of FIG. 1. This requires a correction, that can be repeated in a cyclic manner to get the best estimates of the ion mobility ratio $K_h/K$ at very high electric field. FIG. 17 provide a portion of the original data that was used to calculate the high field mobility that was used to produce the curves shown in FIG. 16. The details will not be discussed here. Note also that the calculations are based on a square asymmetric waveform (e.g. V(t) in FIG. 2) while the actual asymmetric waveform is shown in FIG. 4 (waveform 1).

Assuming that the high electric field change in the ion mobility of $(H_2O)_nH^+$ is represented by the curve shown in FIG. 16, the trajectory of this ion within the cylindrical geometry shown in FIG. 15 can be calculated. As a first approximation, it can be shown that: $R_{final}=\text{sqrt}(2tK(V/\ln(a/b))+R_{initial}^2)$ where $R_{final}$ is the radial location of the ion after a time period of length t, and $R_{initial}$ was the radial location before the time period t. The sqrt( ) is the square root function. Again, this equation only applies if the ion spends all of its time between the radial distances a and b shown in FIG. 15. Moreover the equation only gives useful values of final radial distance if the electric field does not vary significantly between $R_{initial}$ and $R_{final}$. The voltage applied to the inner electrode is V, and the ion mobility is K. For this calculation K is assumed to be constant for the trajectory distance (distance the ion travels), but recall that K is calculated from the high field behavior shown in FIG. 16. For example, if the ion is located at a distance r, and at some selected time (during application of the asymmetric waveform) that the voltage applied to the inner electrode results in an electric field of about 10,000 V/cm, then the ion mobility is calculated to be about K*1.01 where the 1.01 is the value taken from FIG. 16. The value of K is about 2.3 $cm^2$/V-s for $(H_2O)_nH^+$ at room temperature. This mobility, K, cannot be easily determined using the FAIMS instrument, but can be found in the conventional ion mobility spectrometry (IMS) literature.

Figure 18A:
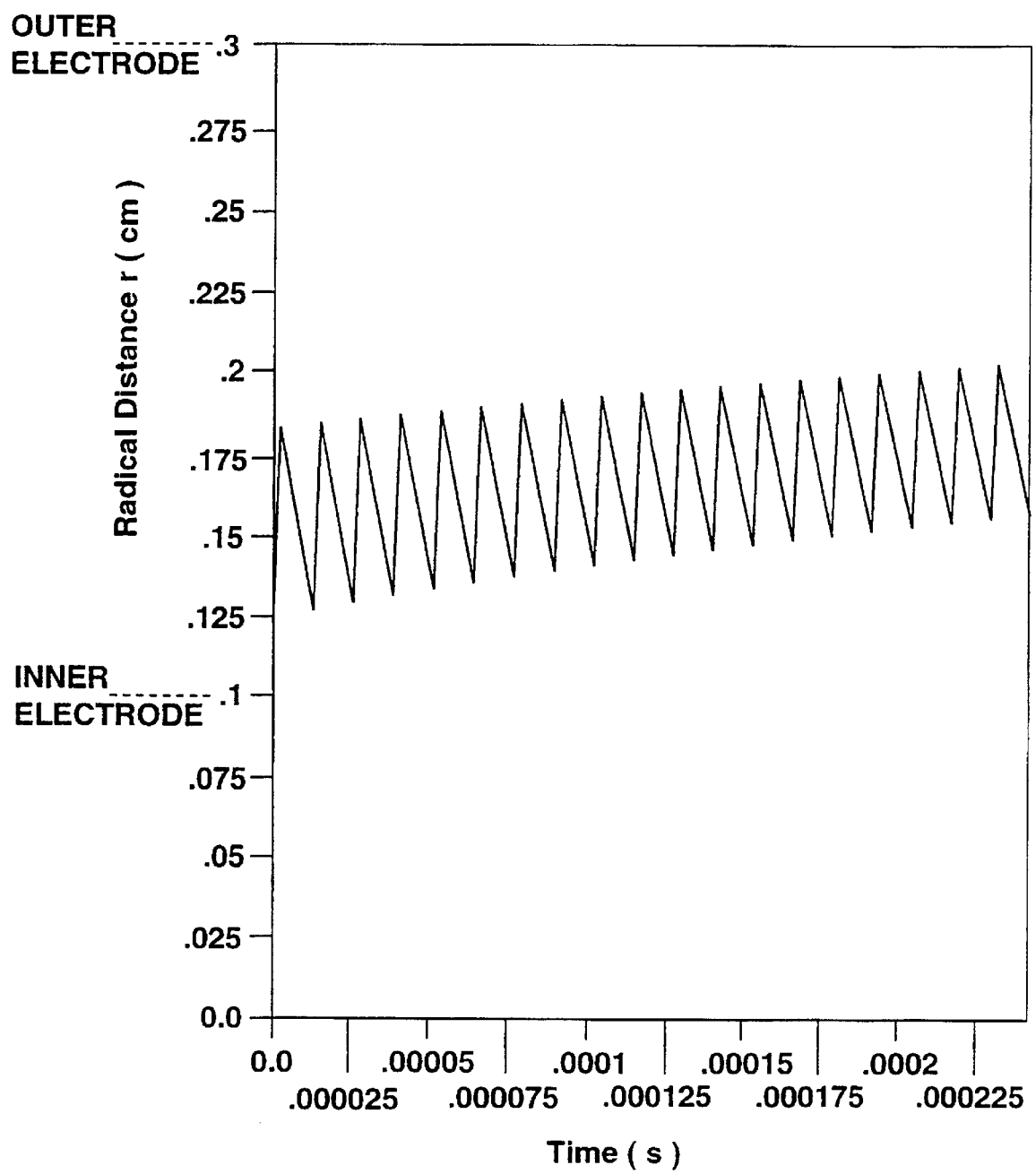
FIGS. 18A–18D show the trajectory of an ion with the high electric field properties shown by the curves in FIG. 16.

FIGS. 18A–18D show the trajectory of an ion with the high field properties shown by the curve in FIG. 16. FIG. 18A shows very few oscillation motions caused by the applied asymmetric waveform of the type shown in FIG. 2.

Figure 18B:
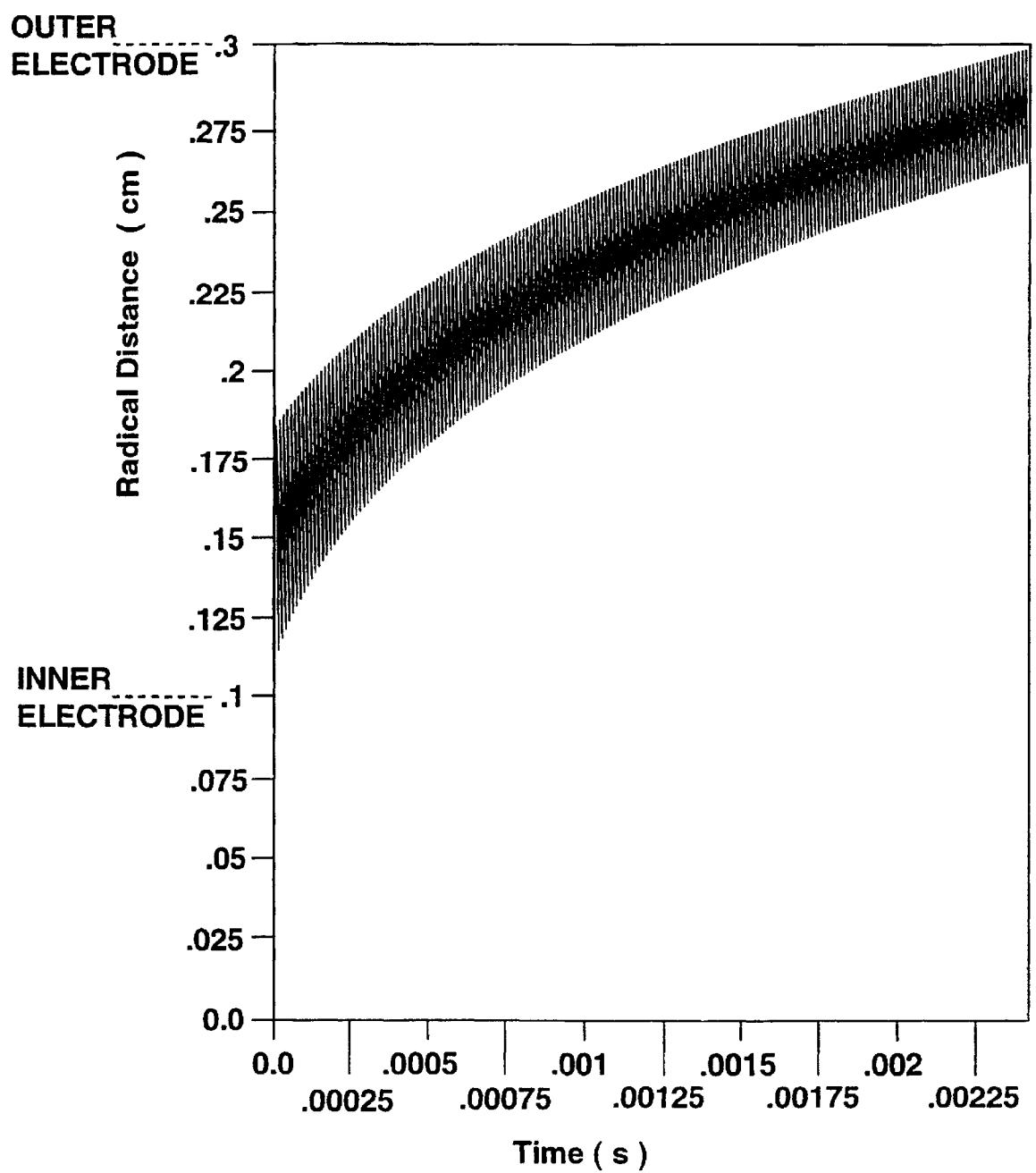
Figure 18C:
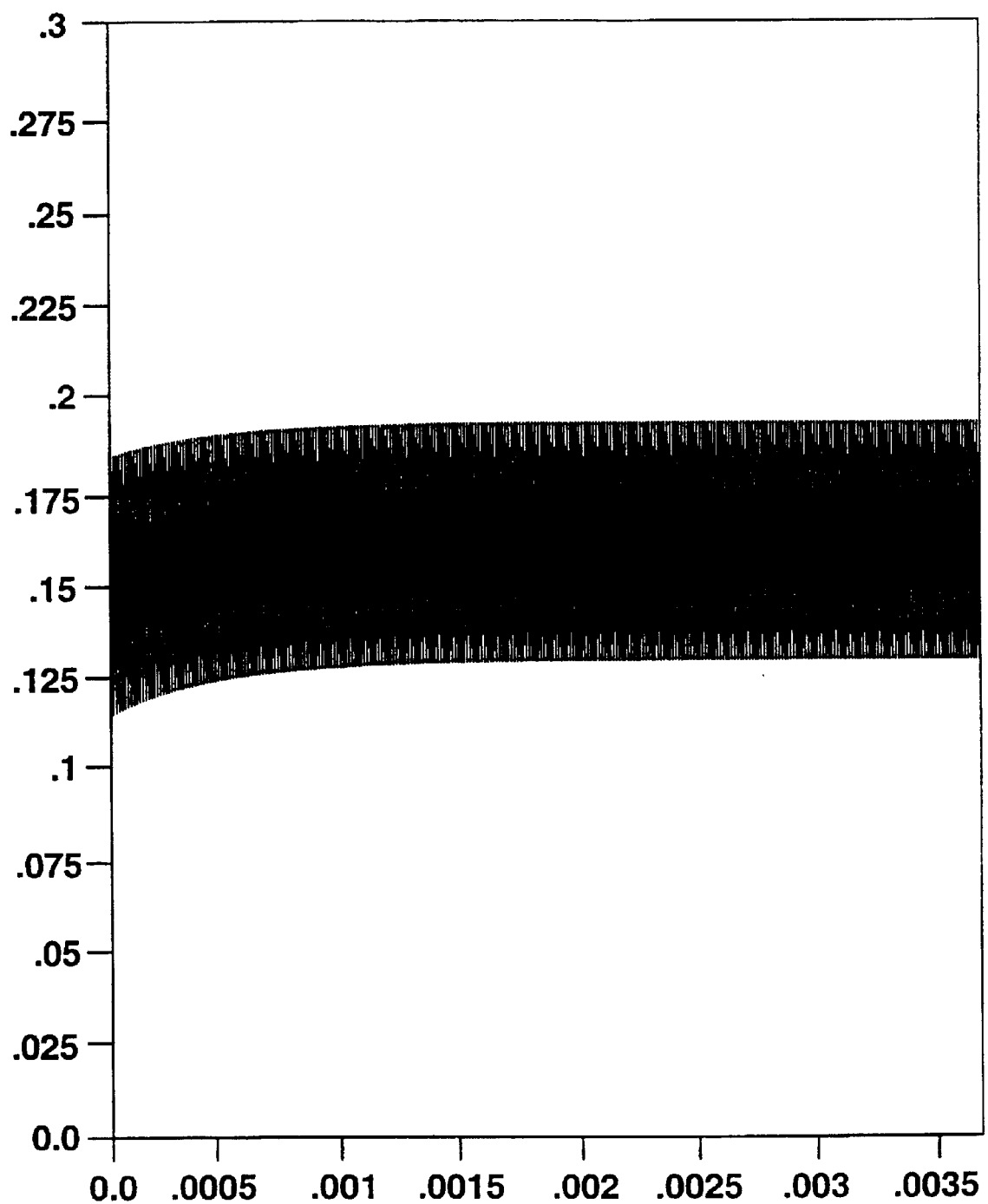
Figure 18D:
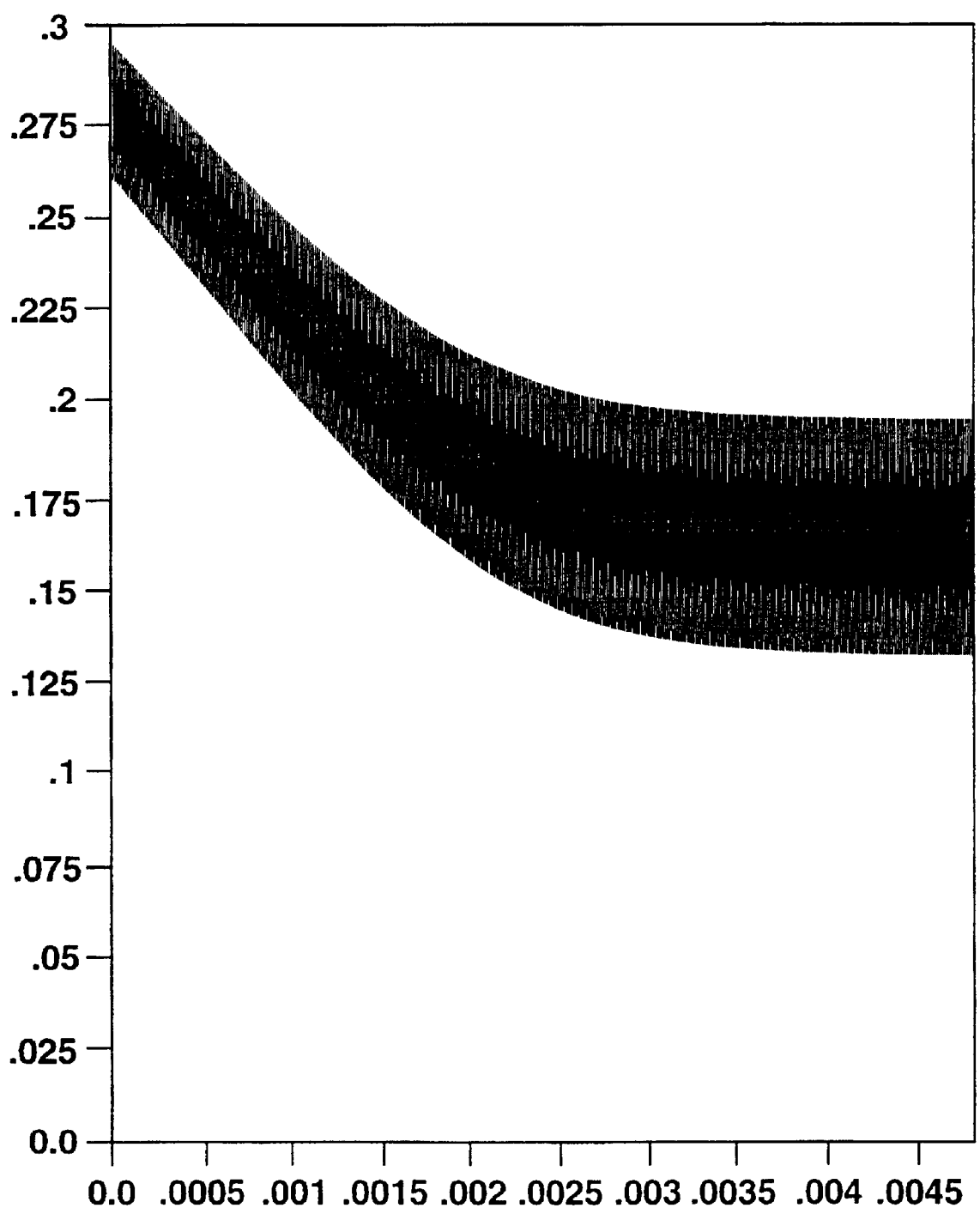

By way of illustration, the cylindrical geometry shown in FIG. 15 may have an inner cylinder having an outer radius of 0.1 cm and an outer cylinder having an inner radius of 0.3 cm. This means that all of the calculations giving rise to the trajectory must be done with a=0.1 and b=0.3 cm, and the trajectory must not extend past these limits. The ion trajectory shown in FIG. 18A is calculated with the ion initially at 0.11 cm radial distance. This is shown as the left-most point in FIG. 18A. The ion will oscillate as a result of the applied waveform and this is shown as an increase and decrease in the radial distance of the ion. The gas flow which transports the ions in the FAIMS analyzer region is simulated (for figure clarity) by showing the trajectory as a function of time (x-axis) in FIG. 18A. The applied voltages for the trajectory simulation were: CV=0 V, DV=2500 V, frequency=83000 Hz, relative ratio of low voltage to high voltage ($t_1$ and $t_2$ in FIG. 2) was 5 to 1. FIG. 18A shows that the ion does not travel exactly the same distances during the low field, and high field portions of the waveform, and the ion experiences a "net" drift. The "net" drift refers to the general motion of the ion radially outward (in the case of FIG. 18A). The simulation was repeated several times, and the results shown in FIGS. 18B through 18D. FIG. 18B was simulated in exactly the same manner as FIG. 18A, except that the number of oscillations of the waveform, and thus of the ion motion, are significantly higher in FIG. 18B. This shows that the ion will eventually cross over the FAIMS analyzer region, and collide with the outer wall which is located in FIG. 18B at the top of the Figure, at radial distance of 0.3 cm. Therefore, the DV and CV conditions that were used to simulate the motion of $(H_2O)_nH^+$ ion in FIGS. 18A and 18B, would not be suitable for the focussing or trapping in an FAIMS with the physical geometry described above. The condition which would be suitable for ion storage is shown in FIG. 18C. The conditions are: CV=−11 V, DV=2500 V, frequency=83000 Hz, relative ratio of low voltage to high voltage ($t_1$ and $t_2$ in FIG. 2) of 5:1. This could have been predicted from FIG. 18B, since the outward drift of the ion might be expected to be retarded by the application of a negative dc potential to the inner electrode. FIG. 18C shows that the ion will experience a net drift from its starting position of 0.1 cm radial distance outwards, but quickly the drift stops (note the ion oscillates because of application of the asymmetric waveform), and the ion progresses neither inward nor outward. FIG. 18D shows the calculated ion trajectory for the same conditions as FIG. 18C except that the original radial starting point for the ion motion was selected to be about 0.26 cm. The ion experiences a drift toward the inner electrode, and stabilizes at exactly the same radial distance as the ion shown in FIG. 18C. This means that an ion, irrespective of its starting position will fall into the ion focussing region. The focussing characteristics of the FAIMS are therefore demonstrated by ion trajectory calculations.

The radial location of the optimum focussing of an ion depends on the high field mobility properties of the ion, and the DV and CV, and geometry of the FAIMS analyzer region. For the example shown above, the $(H_2O)_nH^+$ ion was selected because the high field ion mobility behavior of this ion had previously been established. The optimum combination of DV and CV for the $(H_2O)_nH^+$ ion can be calculated for various FAIMS hardware geometries. The trajectory of the ion can be calculated based upon the principles described in the paragraphs above.

FIGS. 19A–19D show the ion trajectory for a geometry that is shown in FIGS. 11A–11C, the device referred to as the FAIMS-R3-prototype (one of the 3-dimensional, atmospheric pressure ion trapping devices). Because the geometry is not a simple cylinder the ion trajectory calculation is more complex. The calculation is composed of two independent calculations. In the first, the mechanical geometry of the device is entered into a computer program which then calculates the strength of the electric fields around the components. This is done by a method called "relaxation" Jacobi iteration Richardson method), and involves a repetitive series of approximations of the field at every point in the physical space. The field at a given point is calculated as the 'average' of the points in each direction around it. This is repeated for every point in the space. Once this calculation has been completed for every point in the entire space, then the process is started again at the first point, now using the estimations from the previous calculation. This is shown below in 1-dimension. Let us assume that the following are the voltages at several adjacent points in an imaginary 1-dimensional world (before the 'relaxation' calculation has begun). The point at the left most of the array is an electrode at 100 V, and that at the right most point is an electrode at 0 V. We begin by assuming every point is at 0 V, except the electrode at 100 V. The array is shown in the next line:

| 100 | 0 | 0 | 0 | 0 | 0 | 0 | 0 |
|---|---|---|---|---|---|---|---|

Consider the result if we make each point the average of its neighbors:

| 100 | 50 | 0 | 0 | 0 | 0 | 0 | 0 |
|---|---|---|---|---|---|---|---|

And again:

| 100 | 50 | 25 | 0 | 0 | 0 | 0 | 0 |
|---|---|---|---|---|---|---|---|
| 100 | 62.5 | 25 | 12.5 | 0 | 0 | 0 | 0 |
| 100 | 62.5 | 37.5 | 12.5 | 6.25 | 0 | 0 | 0 |

This calculation must be repeated until no further change in the data points is occurring, or at least until the changes in the data array are within specified error limits. The 2 and 3-dimensional versions of the calculation are analogous.

The "relaxation" and "successive over relaxation" methods for numerically solving Laplace and Poisson equations are described in most text books of fluid dynamics (see M. B. Abbot and D. R. Basco, Computational Fluid Dynamics, An Introduction for Engineers (Longmans, London, 1989), Chap. 8). The calculation for a cylindrical geometry must include a small correction for the fact that the points in the radial direction cannot be used with equal weight in the 'average' used to calculate the new value of a point in space. The points in the axial direction (along the length of this cylindrical geometry) are equivalent to each other, but are not equivalent to a point at smaller or larger radial dimension. The surrounding 4 points used for the average of a point in cylindrical geometry must therefore be weighted, two axial points are identical, and the inner and outer points in the radial direction are weighted independently from each other, and from the axial points. Nevertheless the overall method of calculation of electric potential using the 'relaxation' method is the same for all geometries.

The second calculation which is necessary to determine the ion trajectory in an arbitrary geometry is the calculation of the motion itself, given that the electric fields have been established as discussed above. The trajectory is calculated by breaking the ion motion down into small steps in time. At each step in time the ion location, the electric field, phase of the applied asymmetric waveform, etc. are determined. From the strength of the electric field at the point in space/time, the ion mobility at high electric field is calculated (as was demonstrated for $(H_2O)_nH^+$ above). The ion velocity is estimated to be v=KE (or $v=K_hE$), in the manner described above, and the distance travelled is distance= (velocity)(duration of time step). The distance (cm) travelled for the single time step is determined from the velocity (cm/sec) multiplied by the time duration (sec). The new ion location is calculated from the old location, and the distance travelled in the time step. This is repeated, now beginning at the new ion location just calculated in the previous iteration. The iterations are repeated, with the strength of the electric fields due to the asymmetric waveform being constantly adjusted (as appropriate for the frequency of the waveform, and the relative times of the high and low voltage periods in the waveform). The calculation may also include an adjustment of the ion location due to the external forces of a gas flow, or if necessary to clarify the motion of the ion (since a simple back and forth motion doesn't demonstrate the motion very clearly).

Figure 19A:
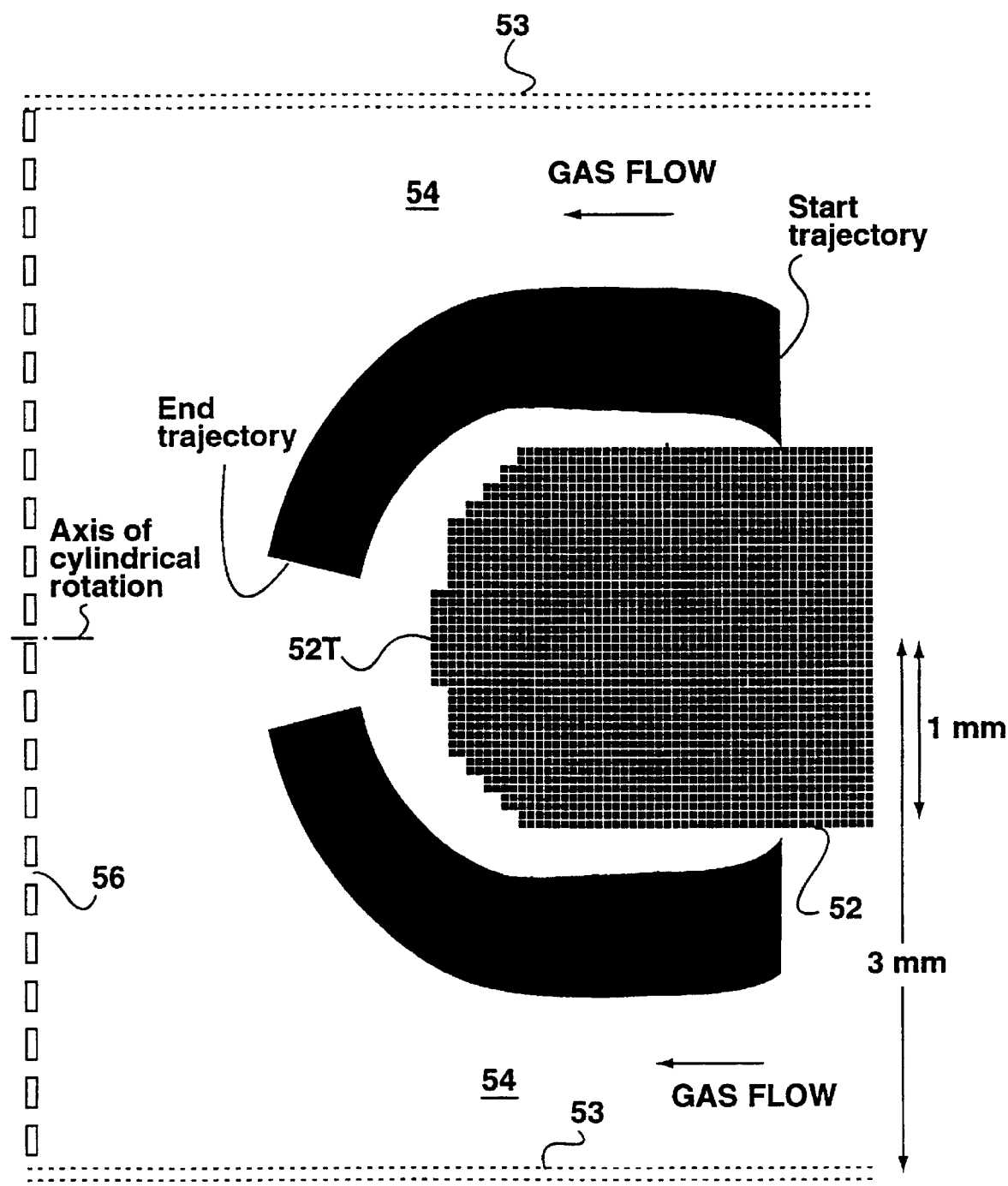
FIGS. 19A–19D illustrate ion trajectory calculations near the terminus of an inner electrode, calculated using the FAIMS apparatus and method described in FIGS. 11A–11D.
Figure 19B:
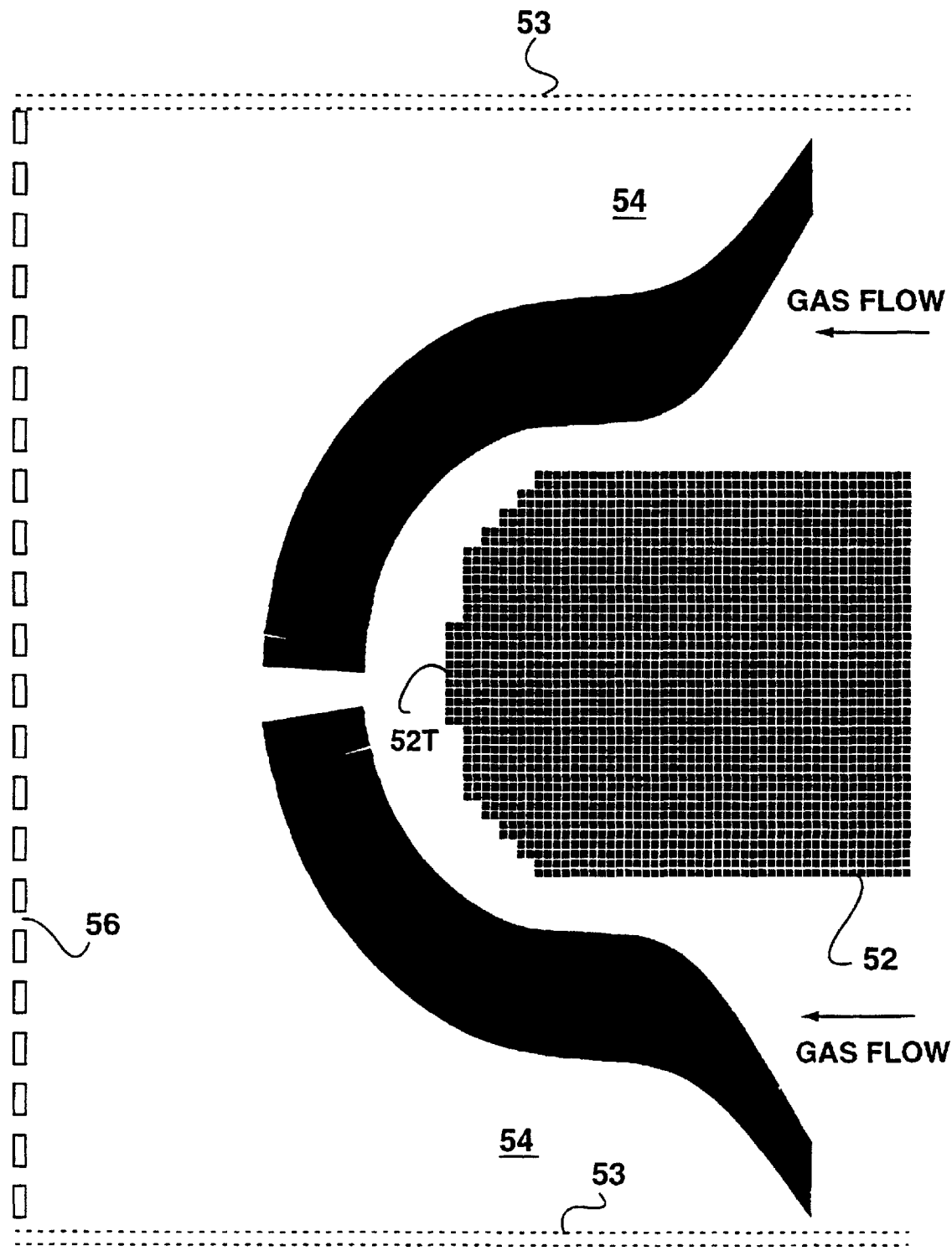
Figure 19C:
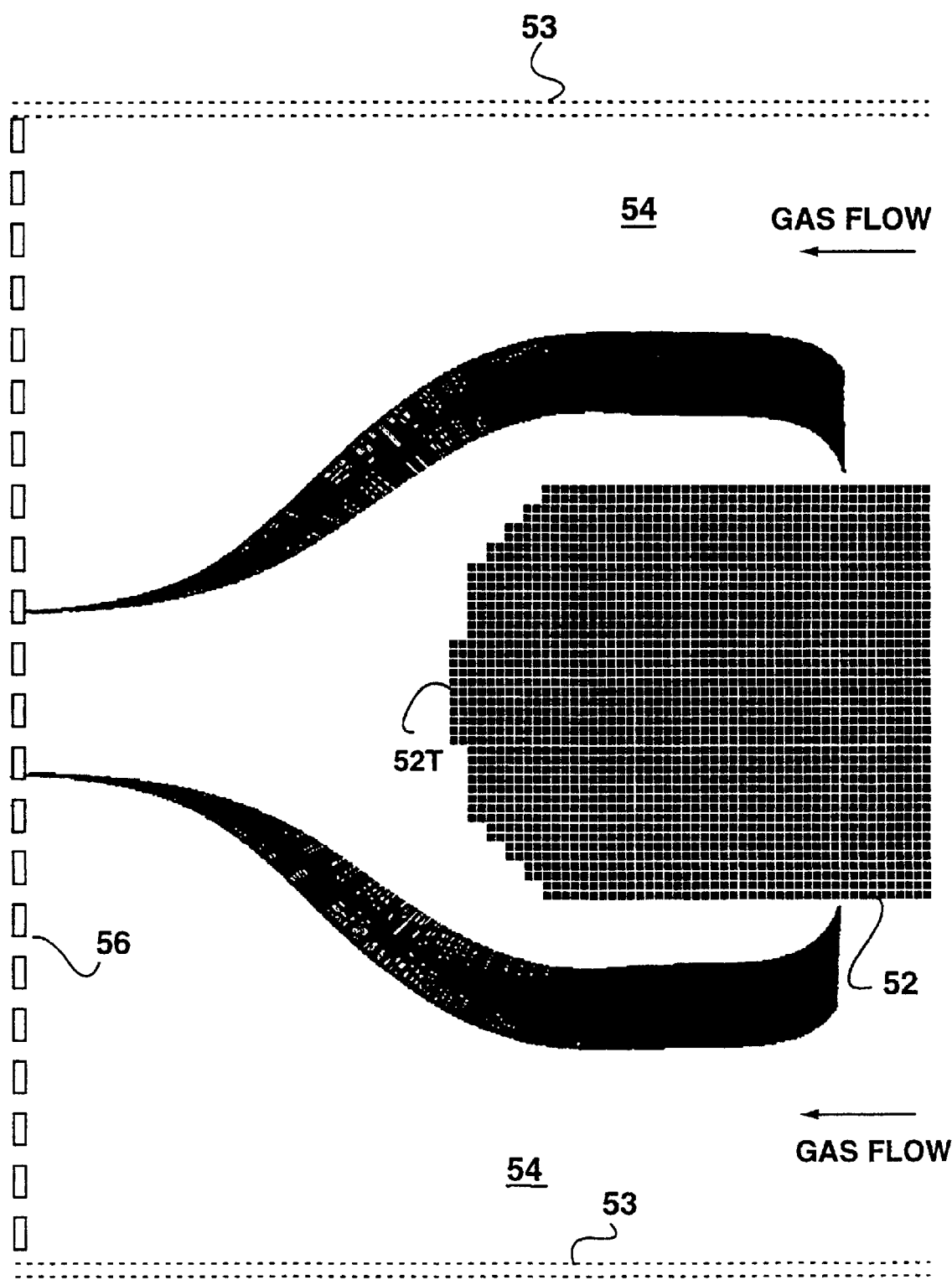
Figure 19D:
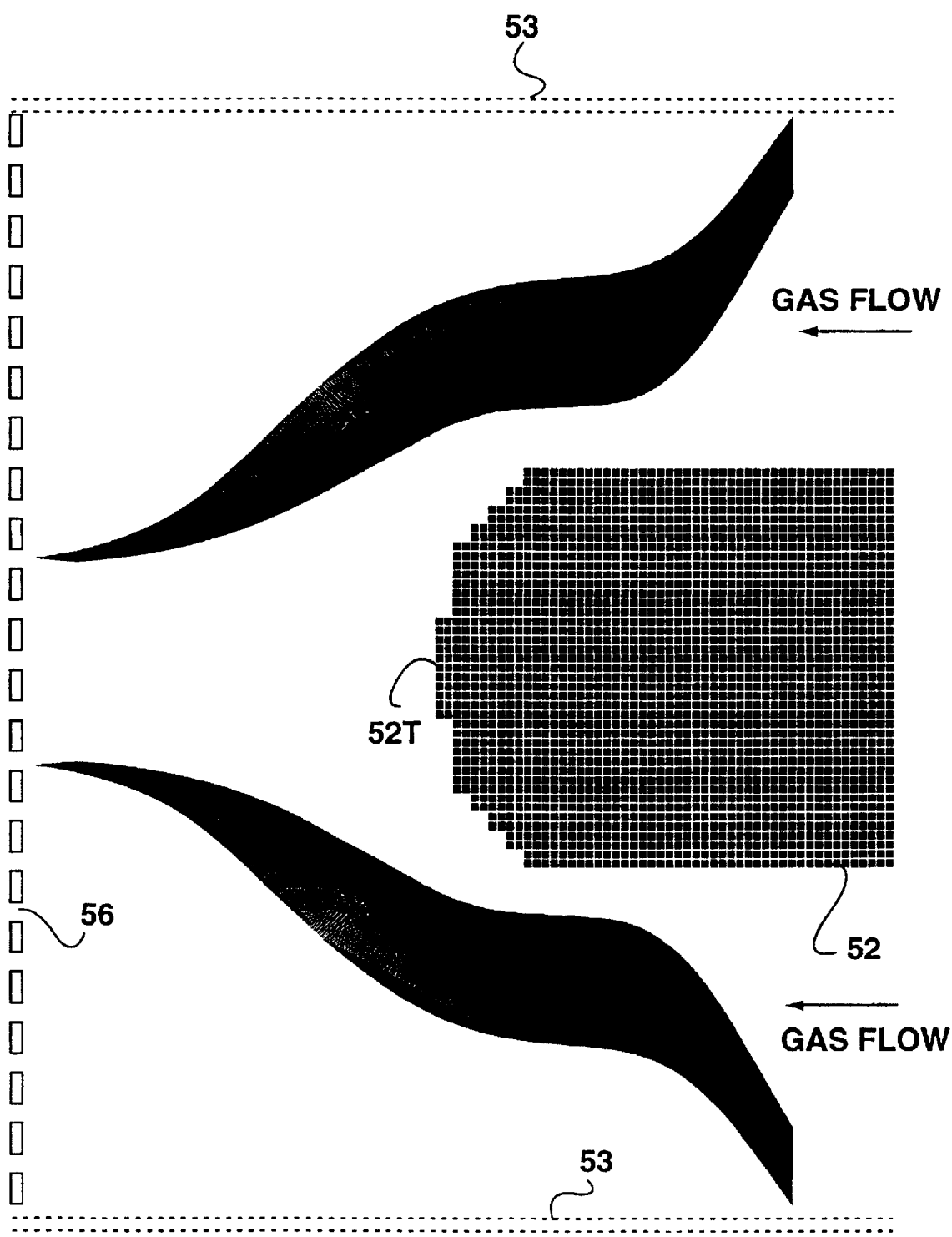

FIG. 19A illustrates an ion trajectory calculated in the method described above, for the geometry shown in FIGS. 11A–11C. The inner electrode is about 2 mm outer diameter, and the outer electrode is about 6 mm inner diameter. This is the same size as the cylinders used in the trajectory calculations shown in FIGS. 18A–18D. The conditions were: CV=−11 V, DV=2500 V, frequency=83000 Hz, relative ratio of low voltage to high voltage ($t_1$ and $t_2$ in FIG. 2) was 5:1, outer electrode=0V, grid electrode=0V. Three electrodes appear in FIG. 19A, exactly corresponding to the hardware illustrated in FIGS. 11A–11C. The inner electrode 52 is solid and ends in a spherical shape 52T near the center of the FIG. 19A. The top and bottom edges are the outer electrode 53, and the left edge of the FIG. is the grid electrode 56 shown in FIGS. 11A–11C. The ion trajectory was initiated near the inner electrode, and an artificial (gas flow) horizontal motion was added to carry the ion from right to left on the FIGS. 11A–11C. The ion oscillated because of the applied asymmetric waveform, and two types of net motion are observed in FIG. 19A. The ion initially moves away from the inner electrode 52, then the distance from the electrode becomes constant. This is exactly the condition shown in FIG. 18C where the net motion in the radial direction soon becomes zero. The ion also drifts because of the added 'gas flow', an artificially imposed longitudinal velocity. Note that the ion progresses along the electrode at constant distance from the inner electrode 52, then follows its curvature 52T. The ion will not leave the location near the terminus 52T of the electrode even with the applied artificial axial direction 'gas flow' velocity. The ion has become trapped near the terminus 52T of the electrode. FIG. 19B shows the motion if the ion trajectory is initiated at larger radial distance (as in FIG. 18D). As explained before, the ion cannot escape the 3-dimensional ion trap near the tip of the electrode 52T.

FIGS. 19C and 19D represent the same physical geometry as FIGS. 19A and 19B, and the ion trajectory begins in analogous locations in radial and axial directions. The conditions are: CV=−11 V, DV=2500 V, frequency=83000 Hz, relative ratio of low voltage to high voltage ($t_1$ and $t_2$ in FIG. 2) was 5 to 1, outer electrode=0V, grid electrode=−7 V. The only difference between the FIGS. 19A–19D is that the latter two (FIGS. 19C and 19D) were calculated with the exit grid 56 voltage negative relative to the outer electrode 53. Under these conditions the ion trap has been removed and the ions will travel toward the grid 56. Initially, the trajectory takes the same form as shown in FIGS. 19A and 19B as the ion will first move toward the optimum balance point for the DV and CV and geometry being used. However, the conditions are not maintained in the vicinity of the spherical terminus 52T of the inner electrode 52, and the exit grid 56 voltage modifies the ion motion, and attracts the (positively charged) ions away from the inner electrode 52, and toward the exit grid 56. Both the attractive force of the grid 56 voltage, and the artificially applied 'gas flow' axial motion will contribute to the ion trajectory as it leaves the vicinity of the inner electrode 52, and approaches the exit grid 56. Note also that the magnitude of the 'oscillation' of the ion due to the asymmetric waveform decreases significantly as the ion moves away from the inner electrode 52.

While 3-dimensional trapping is not achieved in FIGS. 19C and 19D, the behaviour of the ions shown may nevertheless be very useful. When operated in a compromised condition, i.e., non-trapping, but very near trapping conditions, the ions follow the curved surface of the spherical end 52T of the electrode and tend to move toward the center axis. If they are not completely trapped, the ions will essentially escape from the end 52T of the electrode, but they are confined to a small radial distance along the center axis of the inner electrode 52. If the flow of ions is directed into the sampler cone orifice 18A leading to the vacuum chamber, the signal sensitivity will be greatly enhanced in conditions where this 'partial focussing' takes place. It is possible to visualize a commercial version of FAIMS wherein this signal enhancing behavior of the spherical terminus 52T of the electrode is the only part of FAIMS which is exploited. All of the embodiments of the 3-dimensional ion trap of FAIMS described above might be used for this signal enhancement even if the "3-dimensional trapping" is not used per se.

Figure 19E:
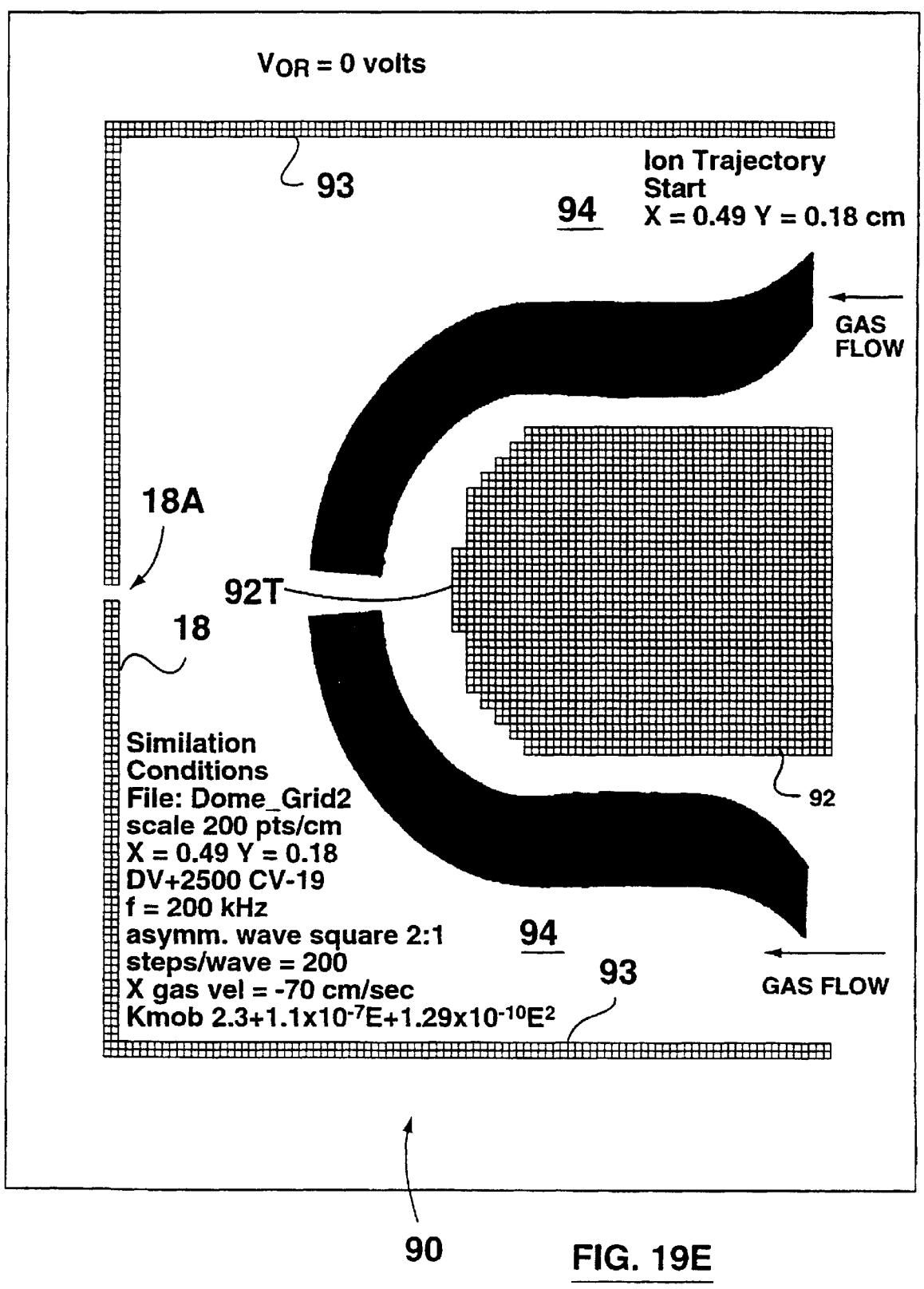
FIGS. 19E–19I illustrate the results of ion trajectory calculations near the terminus of an inner electrode, using various sampler cone voltages in the FAIMS apparatus shown in FIG. 13A.
Figure 19F:
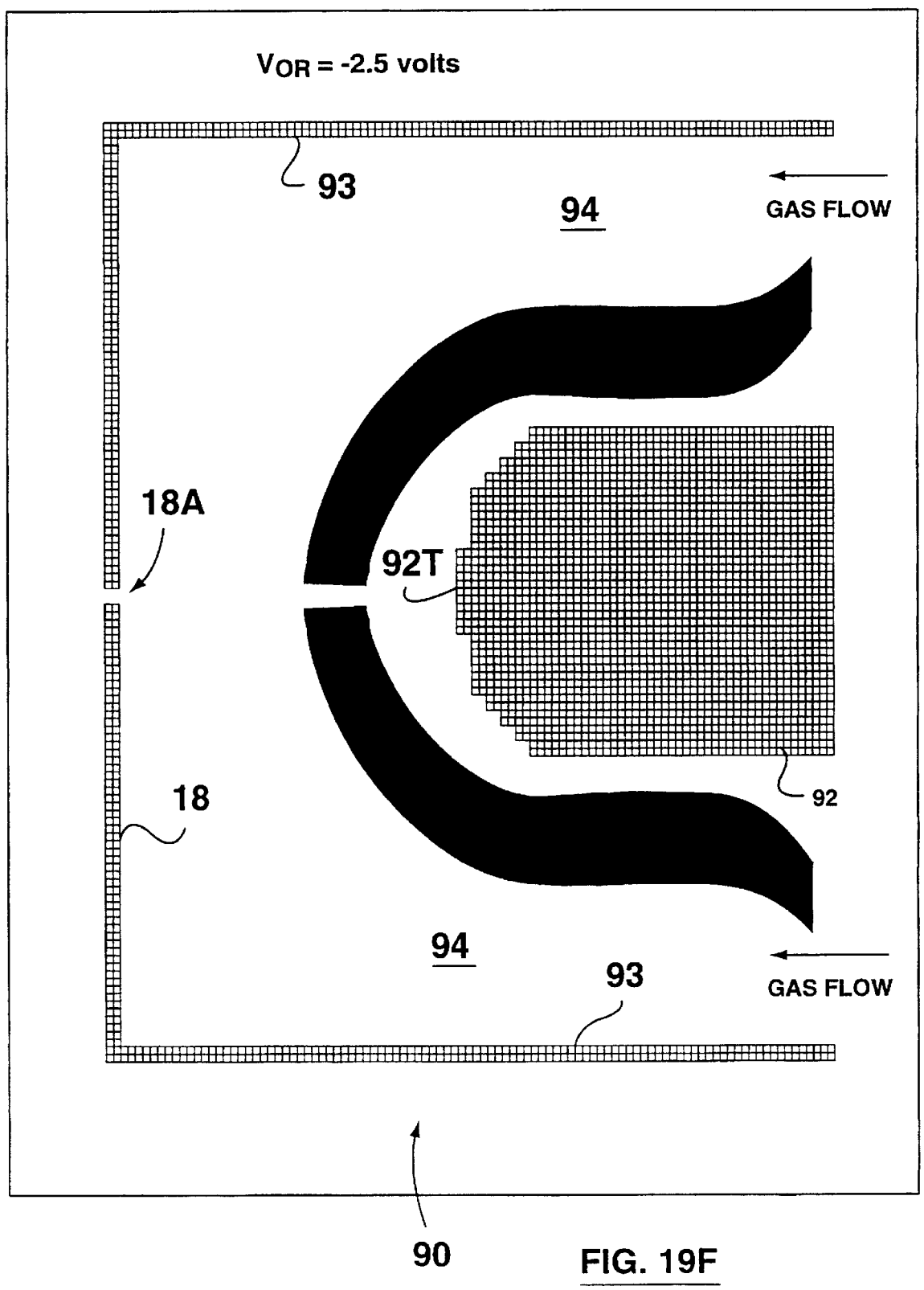

Signal Enhancement Using Ion Focussing at the Spherical Terminus of the Inner Electrode of FAIMS FIGS. 19E–19I illustrate the results of ion trajectory calculations using a FAIMS consisting of a cylindrical outer electrode 93 of about 6 mm id, and an inner electrode 92 of about 2 mm o.d. The annular FAIMS analyzer region 94 is about 2 mm wide along the sides of the device. The inner electrode 92 terminates in a spherical shape 92T which is about 2 mm from the flat, front plate of the sampler cone 18. At the center of the sampler cone 18 is a small orifice 18A leading into the vacuum system. In FIG. 19E, the sampler cone 18 is held at 0 V, i.e., $V_{OR}$=0 V. The conditions used for the ion trajectory simulation appear in FIG. 19E. FIGS. 19F through 19I were prepared in exactly the same manner as FIG. 19E, except that the $V_{OR}$ was changed to −2.5, −5, −7.5 and −15 V respectively. This low applied $V_{OR}$ had the effect of drawing the ions out of the 3-dimensional trapping region. If this extraction occurs at voltages very close to the normal 'trapping' conditions (i.e., indefinite ion trapping), then the ions tend to be focused to near the center axis of the inner electrode 92, and therefore are focused to regions very close to the exit orifice 18A. The detected signal intensity will be maximized at the $V_{OR}$ which confines the ions as closely as possible to the center axis.

Although not shown in the Figures, it is possible that further improvements to the 'compactness' of the ion beam can be achieved by modification of the sampler cone 18. This might involve addition of extra lenses with voltages applied, or the modification of the shape of the front of the sampler cone 18. Additional improvements might also be achieved by 'shaping' the inside surfaces of the outer FAIMS cylinder 93 at the end of the cylinder that is adjacent to the sampler cone 18. A previous version of the trapping experiments, shown in FIGS. 9A and 9B, did use a device with an outer cylinder which had a curved inner surface to maintain an (approximately) constant distance between the outer cylinder and the inner electrode at the spherical end of the inner electrode.

Figure 19G:
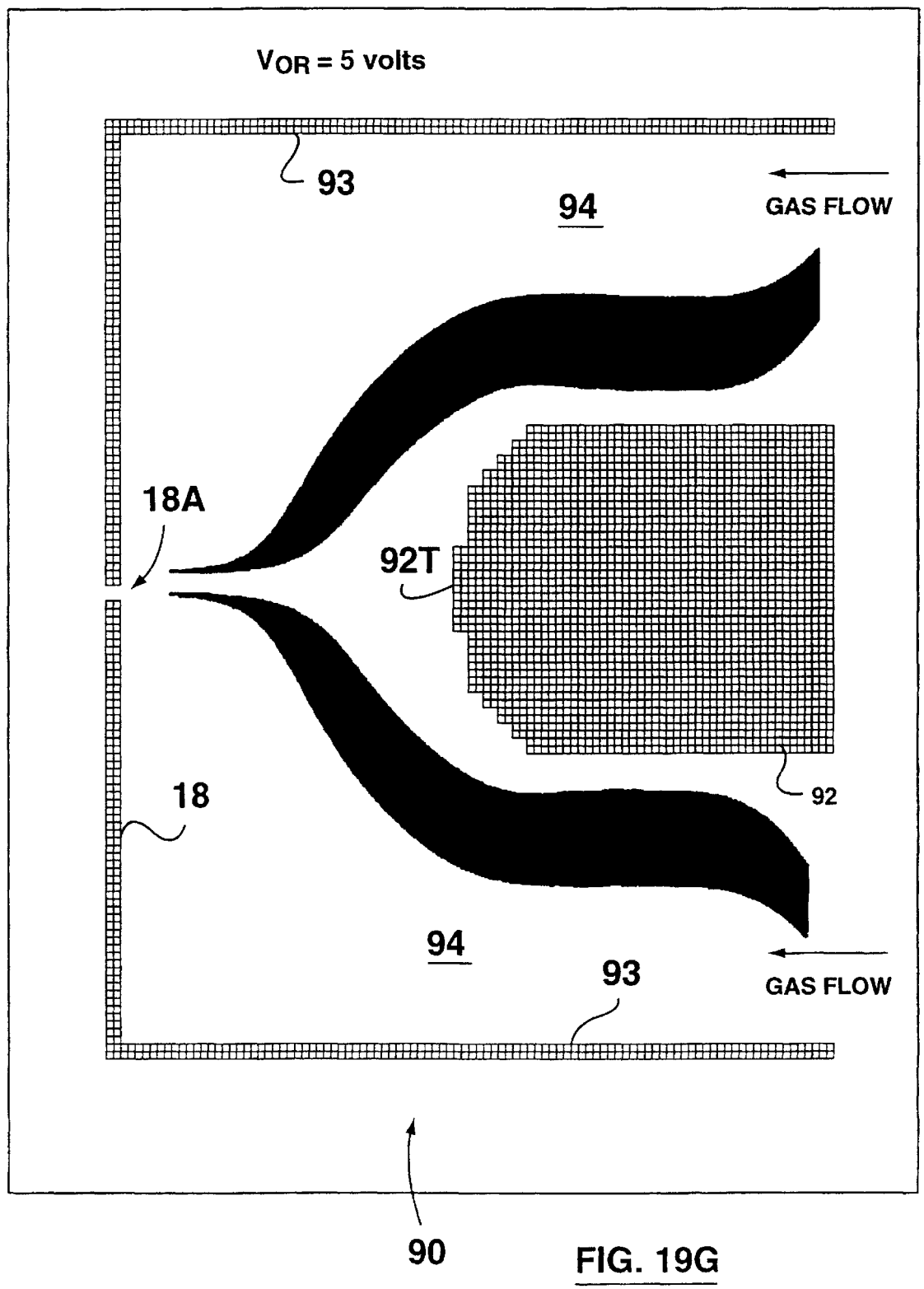
Figure 19H:
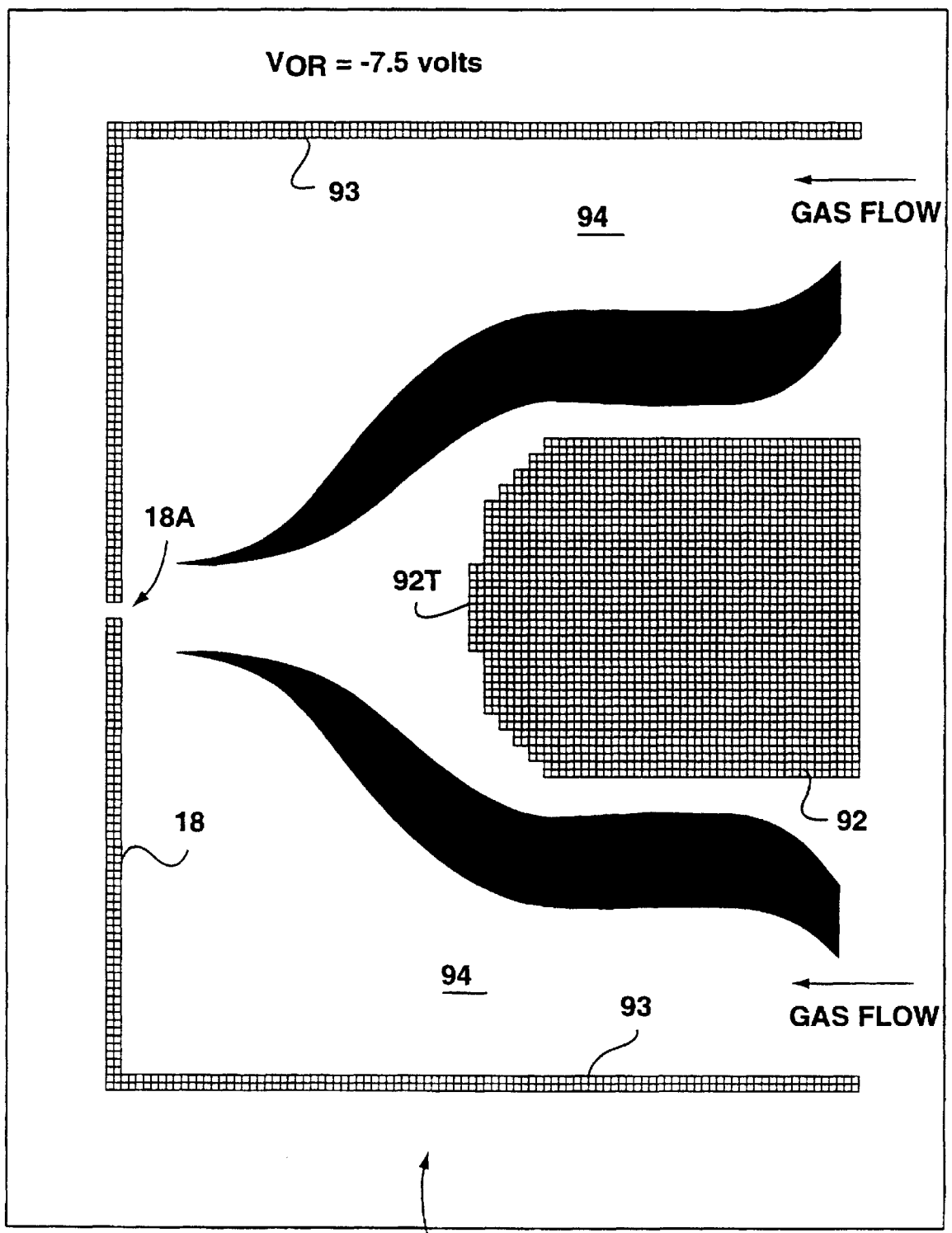
Figure 19:
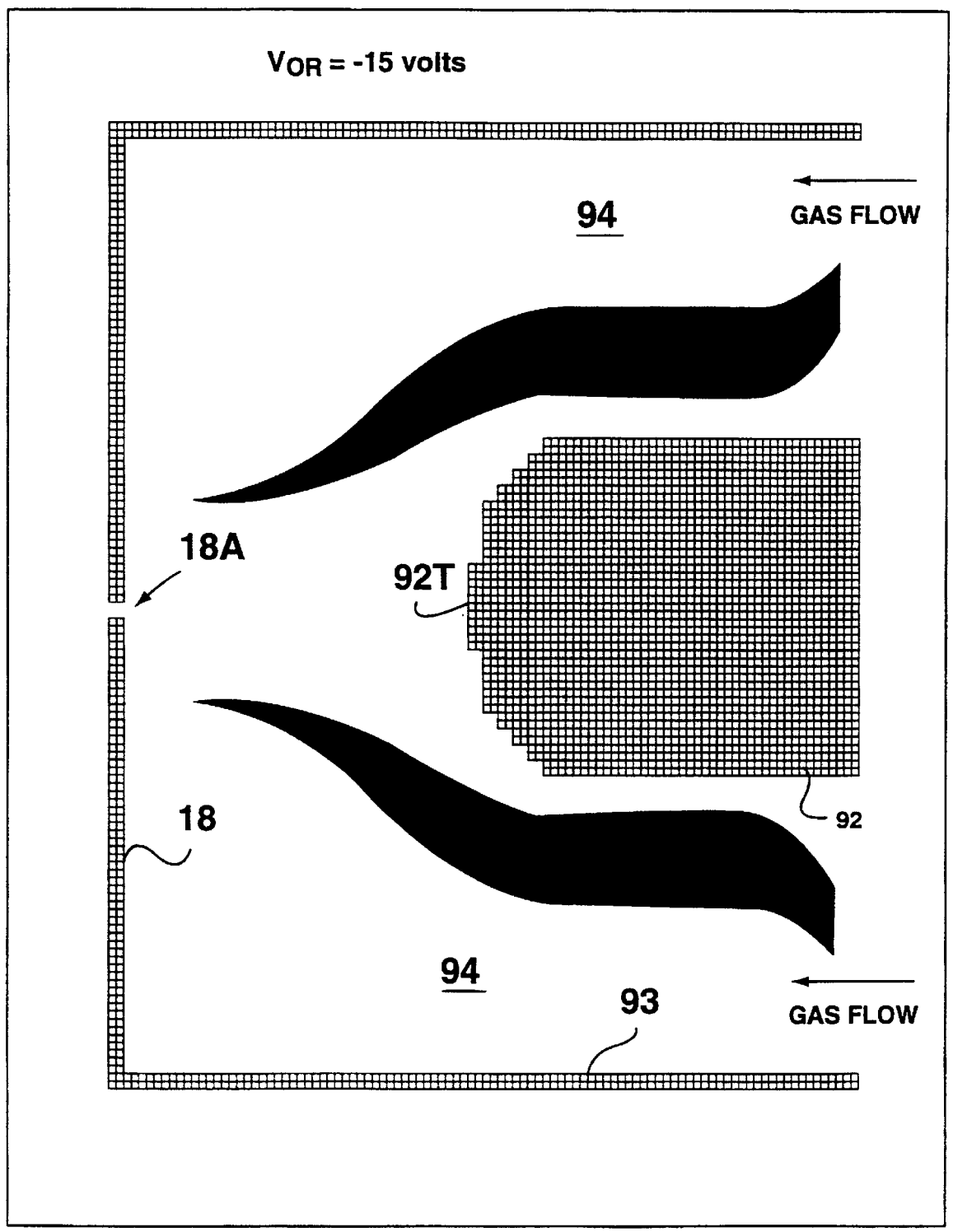

Several experimental parameters will affect the focussing described above, and are shown to be optimized near $V_{OR}$=−5 V in FIG. 19G. These include the gas flow rate, the spacing between the spherical end of the inner electrode 92 and the sampler cone 18, and the applied DV and CV. It is expected that optimization of the detected ion intensity will depend mainly on these parameters. The gas flow will control at least two factors, namely the rate that ions flow into the trapping region from the length of the FAIMS analyzer region 94, and secondly the turbulence at the end of the inner electrode. The simulations shown in FIGS. 19E through 19I do not take into account gas turbulence and ion diffusion. The effectiveness of the focussing action will require a gas flow that maximizes the ion transport rate into the 'trapping region', and simultaneously minimizes ion loss through turbulence. The trajectory calculations shown in FIGS. 19E through 19I also do not account for gas flows in directions non-parallel to the x-axis. If the experimental system includes gas flowing, for example, radially outward from the FAIMS trapping region, as would occur in the system shown schematically in FIG. 13A, the locations of the maximum ion intensity would have to be determined experimentally. The modelling serves to suggest that this ion focussing can enhance sensitivity in some set of optimized experimental conditions.

Figure 20:
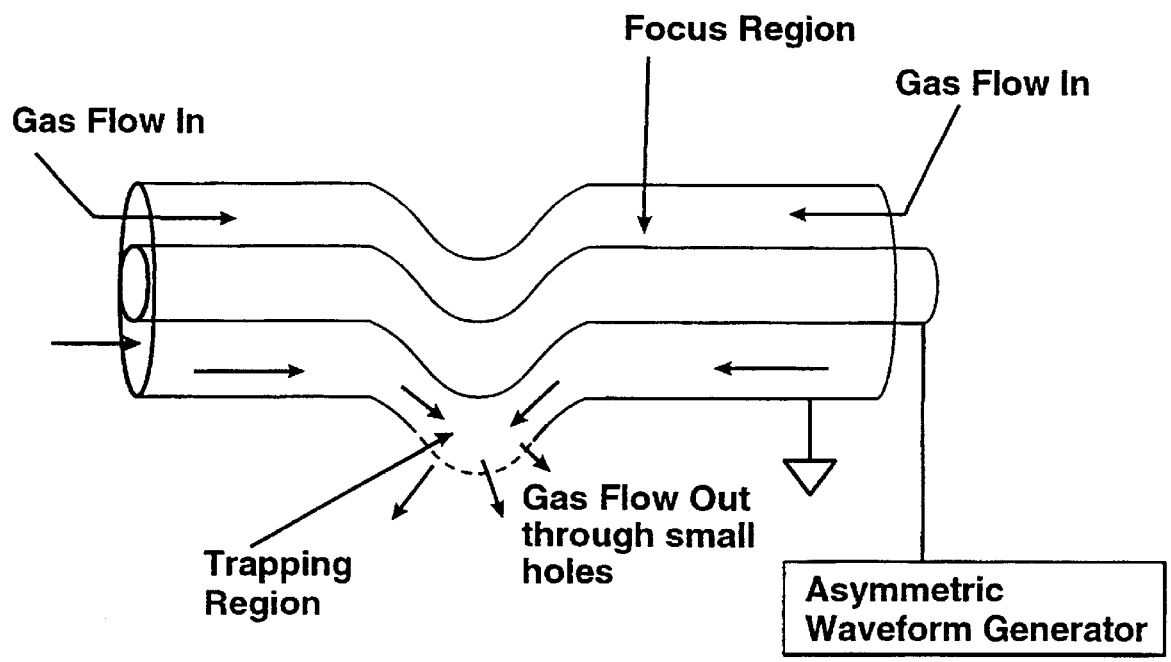
FIG. 20 shows an example of an unusual shape of a FAIMS device designed to establish conditions for ion trapping or focussing.

Several possible hardware designs can achieve the effects shown in FIGS. 19E through 19I. These embodiments require some essential components:

(1) the electrodes must have curved surfaces, including cylindrical, or spherical, but also including surfaces that do not simply fall into one of these categories. An example of an unusual shape which would serve to establish conditions for trapping or focussing, is a cylindrical rod which has a bend in it, somewhat like a hairpin turn, shown in FIG. 20. With appropriate gas flows, a trapping region can be created.

(2) the ions must be transported to the trapping region by gas flows, or by electric field gradients. All of the previously described embodiments of FAIMS take advantage of gas flows, since these function quite independently of the voltages applied, especially DV and CV. The use of gas flows is relatively simple to visualize, and easy to create experimentally.

Figure 21:
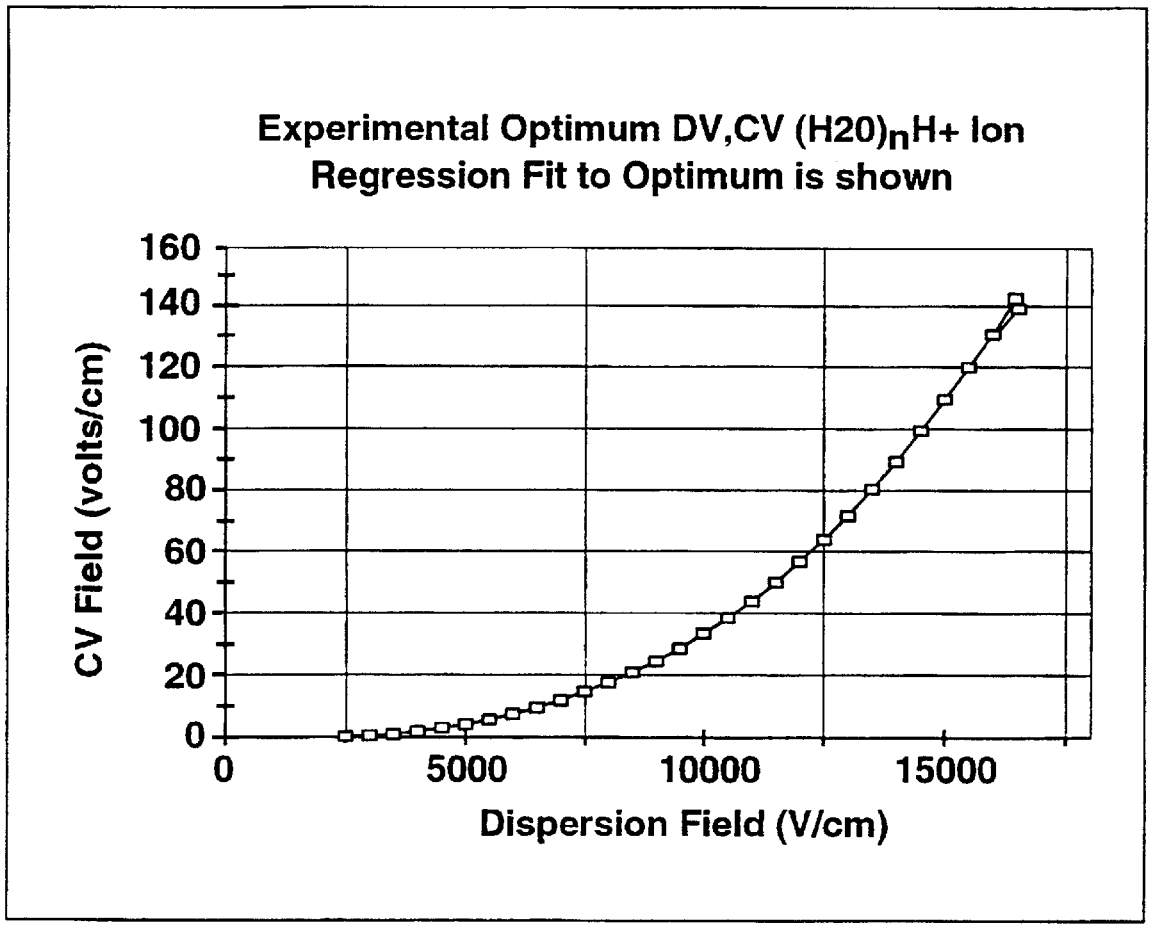
FIG. 21 is a graph plotting the optimum combinations of CV and DV for $(H_2O)_nH^+$, based on data collected by a series of CV scans as shown in FIG. 17.

Qualitative, Simple Method for the Understanding of Ion Focussing and Ion Trapping There exists an optimum condition of DV and CV at which an ion is transmitted through the FAIMS analyzer. Referring back to FIG. 17A, a set of repeat sweeps of the CV at a series of DV values ranging from 2100 V to 3000 V is shown. The location of the peak maximum for some ion ( in this case $(H_2O)_nH^+$) represents the condition where the compensation voltage CV is just strong enough to balance the net ion drift towards the wall of the FAIMS analyzer. Consider therefore that the $(H_2O)_nH^+$ ion can be transmitted through the FAIMS analyzer region at a number of ideal combinations of CV and DV. If the ion experiences a combination of CV and DV that is different from the ideal, then the ion collides with a surface. A plot showing the ideal combinations of CV and DV for $(H_2O)_nH^+$ is shown in FIG. 21. The ideal combination of DV and CV might be called "balanced" because the ion experiences no 'net' motion. The plot shown in FIG. 21 illustrates this balanced condition in terms of electric field (based on DV), rather than the applied voltage DV and CV, moreover each data point on the FIG. is an experimentally acquired combination of DV and CV, collected much as shown in the traces of FIG. 17. Each point is the CV with the maximum efficiency of transmission (peak maximum shown for each trace in FIG. 17) for that setting of DV. Since the annular FAIMS analyzer region 14 of the FAIMS-E 10 is about 2 mm wide, a voltage of DV of 2000 will result in a field of about 2000/0.2=10,000 V/cm. Similarly an applied CV of −10 V will result in a field of about −10/0.2=−50 V/cm. The x- and y-axes of FIG. 21 are displayed as electric field (V/cm) (absolute values, unsigned).

FIG. 21 also shows a trace for the best fit third order regression to this data. This regression will help to determine the best combination of CV and DV under conditions which fall between the experimentally determined points. The fit to the data shows only an appearing for the last points at high DV field (electric field which results from the application of DV, at the maximum applied voltage). Note that the 'DV field' is intermittent, since a part of the asymmetric waveform has a lower, opposite polarity time period. This maximum will be used as a 'reference point', for the purposes of this description.

We will address the following question. Assume that an ion is located in the center of the FAIMS analyzer region (radially) and assume it is at a balanced condition at optimum DV and CV for the given hardware geometry. This means that the electric fields due to CV and DV fall directly on the line drawn in FIG. 21. The cylindrical geometry shown in all of the FAIMS diagrams in this document will have electric fields that are not constant along the radial direction in the FAIMS analyzer region. (The field may or may not be constant in the longitudinal direction, depending on the geometry of the particular device. ) If the electric field is not constant, will the optimum conditions shown by the curve in FIG. 21 be maintained everywhere in the FAIMS analyzer region?

Figure 22A:
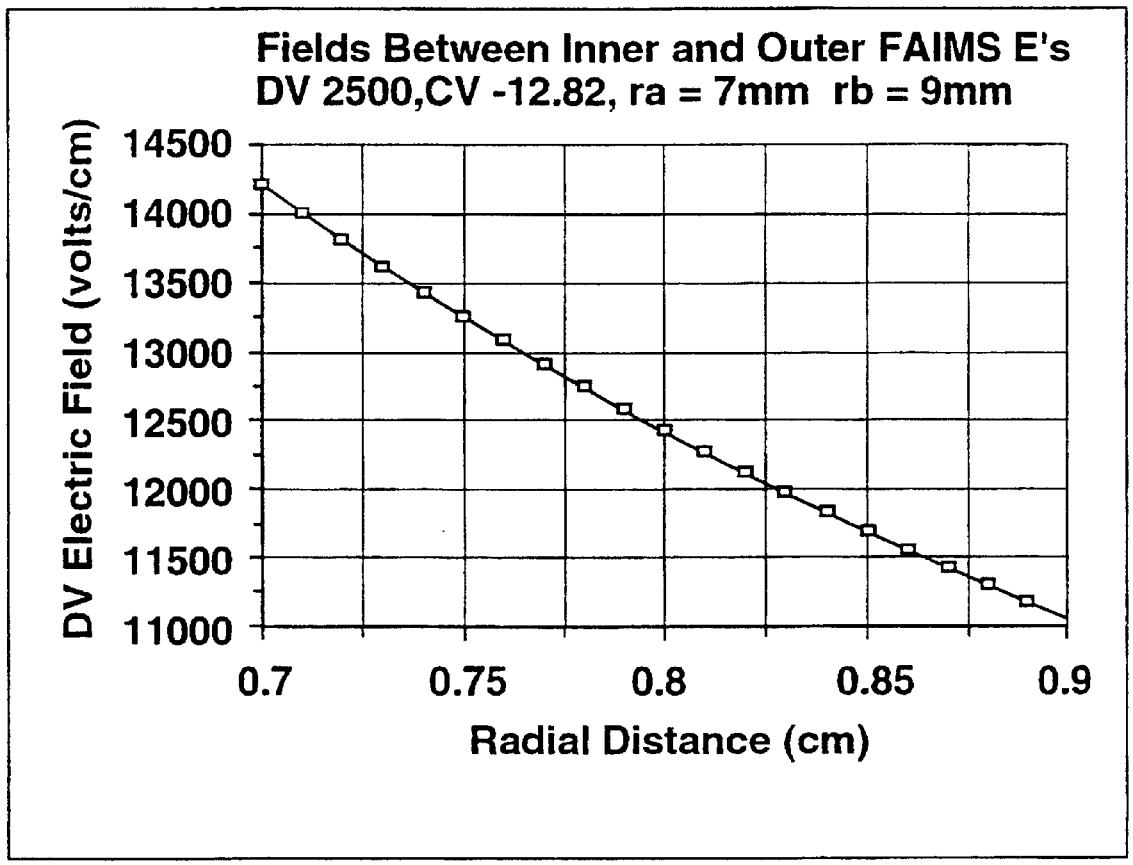
FIG. 22A illustrates the electric field due to DV radially across the FAIMS analyzer region for a given FAIMS apparatus.
Figure 22B:
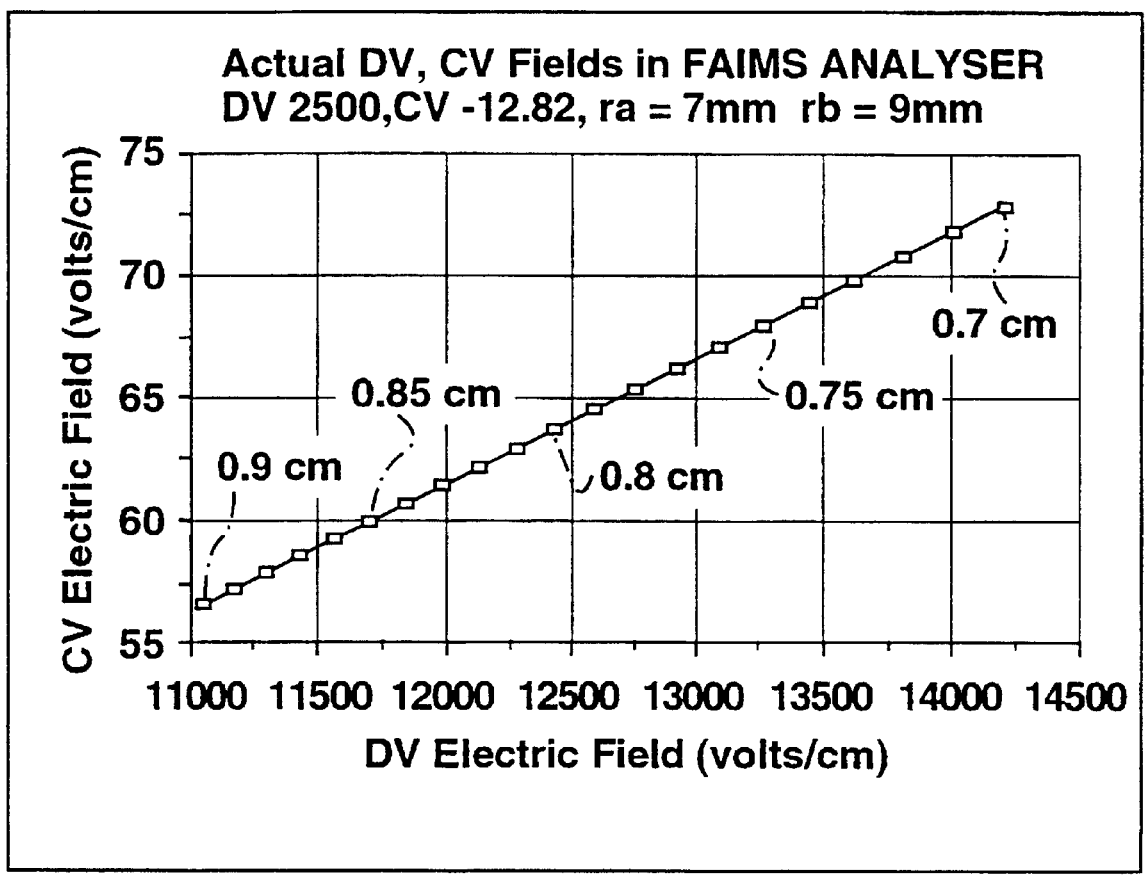
FIG. 22B is a graph showing the electric fields due to DV and CV plotted against each other at several radial locations in the FAIMS analyzer region.

FIG. 22A illustrates the actual fields due to DV (2500 V) radially across the FAIMS analyzer region 14 of the modified FAIMS-E 10 shown in FIGS. 3A and 3B. FIG. 22B illustrates both the actual fields due to DV (2500 V) and CV (about −13 V) that are found radially across the FAIMS analyzer region 14 of the FAIMS-E 10, but unlike FIG. 22A, the fields will be plotted against each other in the manner used in FIG. 21. The points corresponding to some of the physical, radial positions are noted on the diagram. At the right side of FIGS. 22A–22B, the field is highest, and corresponds to the surface of the inner electrode 12, at radial distance of 0.7 cm. Similarly the left side of the FIG. 22B corresponds to the inner edge of the outer electrode 13.

Figure 22C:
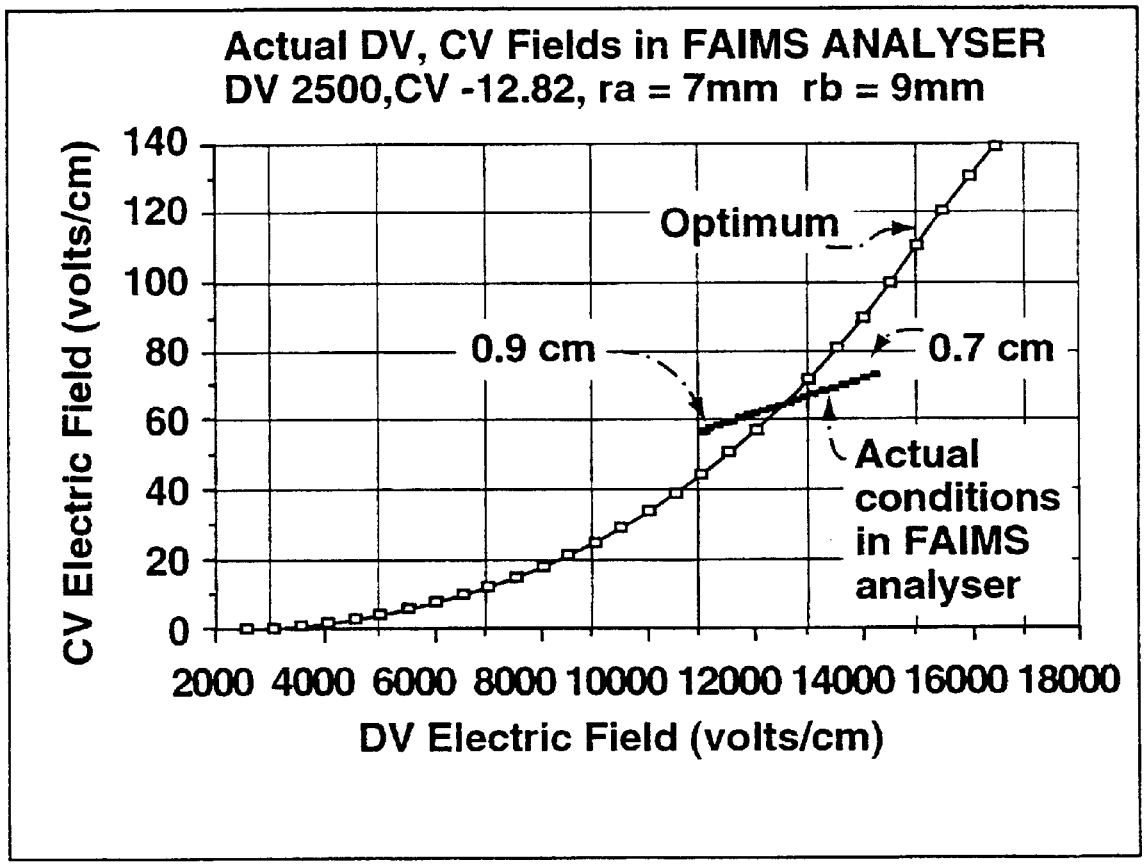
FIG. 22C is a graph showing the intersection of the actual conditions and optimum conditions for DV and CV.

Compare FIGS. 21 and 22B. During a FAIMS experiment DV and CV are applied to the inner electrode. The DV field is not constant, but rather falls within a small range of values (FIG. 22B, x-axis), which in turn is only a small portion of the range of fields described by FIG. 21. The curve in FIG. 22B can be superimposed on the graphic shown in FIG. 21 to give FIG. 22C. FIG. 22C shows that the real, physical conditions of electric fields within the FAIMS analyzer region do not all correspond to points with a balance of DV and CV. Recall that the short curve of 'actual' conditions reflects the conditions at a set of different radial distances (i.e. the left most point of the short curve is the condition of fields at 0.9 cm, near the outer electrode, and the right most point is physically located near the inner electrode surface). Naturally at least at one point, corresponding to the center of the FAIMS analyzer region in this 'selected' combination of DV and CV, there exists the so-called balance where the ion migrates (net drift) neither toward the inner or outer electrode. Note also, there are many combinations of DV and CV in which the entire line shown for 'actual conditions' in the FAIMS analyzer will not cross the optimum balance curve at any point. For example if the DV is reduced to 50% of that shown in FIG. 22B, the short trace for 'actual conditions' in FIG. 22C will move left along the x-axis to fall at a much lower x-axis value of 'DV Electric Field'. If the CV voltage is unchanged the short trace in FIG. 22C will not cross over the 'optimum' balance trace, and the ions will not be able to be transmitted through the FAIMS.

The comparison of the two traces in FIG. 22C also introduces one further question. If the ions, which are at the radial distance wherein the 'optimum' and 'actual' traces intersect, experience no 'net' motion radially, i.e. are at a balance point, what is the behavior of ions at larger radial distances, and at smaller radial distances? They must experience a net drift. For the conditions shown in FIG. 22C, the ions at radial distances larger than the crossing point, i.e. to the left of the intersection, will drift towards the intersection point i.e. toward smaller radial distances. The ions which are at small radial distances, will also drift toward the intersection point i.e. toward larger radial distances. If ions from every radial location other than the 'balance' or focus point (intersection of the traces in FIG. 22C) drift toward this focus point, then the device has the FAIMS ion focussing property that was described above. If the motions are divergent, i.e. away from the 'balance' point, then no ions can pass through the FAIMS. In mode 1 (P1, positive ions) the ions drift toward the focus point when DV is positive, and CV is negative polarity (CV and DV applied to the inner electrode). If both of these polarity values are reversed, then the ion motion (type A, FIG. 1) is divergent instead of convergent. This is the reason that the ions of the two types are automatically separated in the FAIMS. This is the reason the spectra of modes 1 and 2 are always different, and must be always considered as independent spectra. The ions (to a first approximation) which appear in P1 do not appear in P2 type spectra, and vice versa. The same applies to N1 and N2 type spectra.

Figure 23:
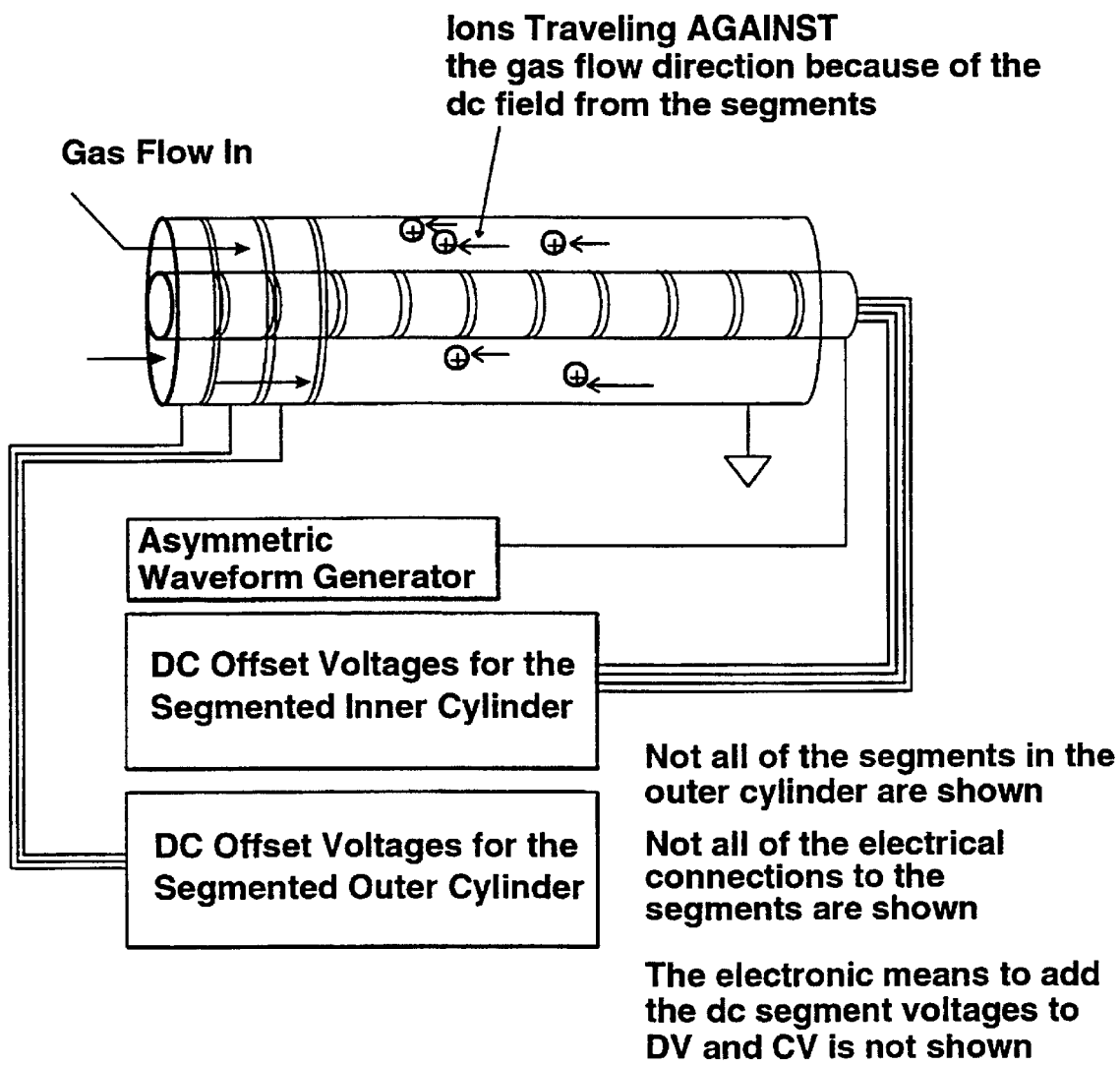
FIG. 23 shows a segmented FAIMS apparatus for transporting ions along the FAIMS analyzer region.

Now referring to FIG. 23, it is possible to visualize the transport of ions in FAIMS using electric fields. A possible embodiment would require that the FAIMS unit be segmented, much in the same way that Javahery and Thomson (J. Am. Soc. Mass Spectrom. 1997, 8, 697–702) used a segmented rf-only quadrupole to create a longitudinal electric field to draw ions along the length of a set of quadrupole rods which were operating with the usual applied high frequency, high voltage ac voltage applied to them. The segments in either the case of segmented quadrupole rods, or FAIMS, are held at slightly different dc potentials, which creates a field superimposed on the other non-constant fields. A possible way to do this is shown in FIG. 23.

Based on a similar concept, a device for 3-dimensional trapping using only electric fields in a segmented FAIMS may be developed, and is described below.

3-Dimensional Trapping Using Only Electric Fields in a Segmented FAIMS

This segmented FAIMS version of the 3-dimensional trap is novel because it does not use gas flows as one of the trapping components. In the trapping of ions at the spherical end of the inner electrode, as previously described, the ions are held by a combination of the motion of the gas sweeping the ions towards the end of the inner electrode, and the FAIMS focussing action caused by the asymmetric waveform. In that device, upon stopping of the gas flows, the ions can begin to make their way back along the length of the FAIMS inner cylinder., The driving force for this migration would be diffusion and ion-ion repulsion which creates a so-called space-charge in the zone where the ions are congregated.

In the present description of a segmented FAIMS ion trap, the ions are held entirely because of the combination of the asymmetric waveform and the gently rising dc voltages applied to the adjacent segments which prevents ion motion in either direction along the length of the segmented FAIMS device. The stopping of the gas flow will have only a minor affect on the ions caught in the ion trap, and there exists no escape even if the gas flow is zero. Consider this new version of 3-dimensional trapping in more detail.

Figure 24:
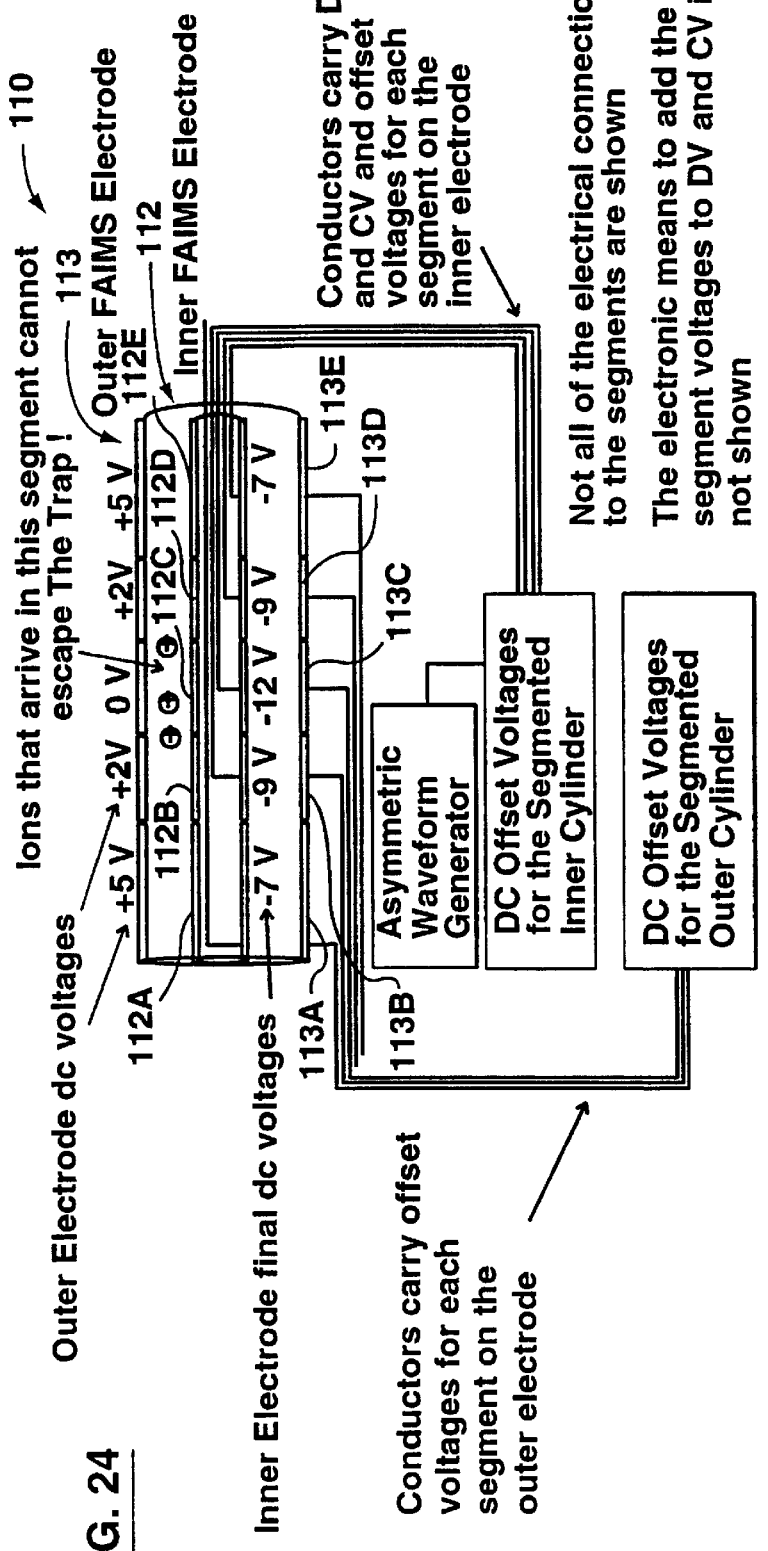
FIG. 24 shows a schematic of a segmented FAIMS apparatus for trapping ions within the FAIMS analyzer region.

FIG. 24 shows the segmented cylindrical outer 113 and inner 112 electrodes of FAIMS device 110. The high voltage asymmetric waveform of FAIMS is applied to the inner electrode 112. The ions will be focused between these cylinders 112, 113 given the correct combination of DV and CV, and the cylindrical geometry. In normal operation all of the segments 112A or 113A would be at identical voltages, i.e., the inner electrode 112 is one conductor, and the outer electrode 113 is also one conductor. Assume that typical conditions for some ion to be focused between the cylinders are DV=2500 V and CV=−12 V. This is the condition shown in FIG. 24. If the electrodes were not segmented, the outer electrode would be at e.g., 0 V. Similarly the inner electrode would be only at one condition e.g., asymmetric waveform DV=2500 V with −12 V offset compensation voltage. Under these conditions if the ions were carried into the annular space between the cylinders by a gas flow, they would proceed longitudinally, carried from one end of the FAIMS analyzer to the other end of the device by the flowing gas, simultaneously being focused at some radial distance and between the inner and outer electrodes 112, 113.

Still referring to FIG. 24, this situation can be changed substantially once the inner and outer electrodes 112, 113 are segmented 112A–112E, 113A–113E. If all of the new dc voltages added to the outer electrodes 113A–113E are 0 V, and all of the new dc voltages added to the inner electrodes 112A–112E are 0 V, then the conditions described in the paragraph above are returned, and no 3-dimensional trap exists, only the 2-dimensional focussing between the cylinders. Visualize next, that a set of new, small, dc voltages are applied to each segment 112A–112E, 113A–113E of the FAIMS device 110, such that the middle segment of the inner and outer electrodes 112C, 113C have the lowest applied voltage. Note, however, that each voltage applied to the outer electrode 113 must be matched by the same (approx.) voltage added to the inner electrode 112. This means that if +5 V extra are added to the first segment 113A of the outer electrode, then +5 must be also added to the same segment 112A of the inner electrode. If that segment already had −12 V compensation voltage added to it, then the new +5 is added to that CV to give a net dc voltage of −7 V on that segment. This approach is used to add voltages to the other segments 112B–112E, 113B–113E, in such a way that the middle segment 112C, 113C (in the FIG. ) has the lowest applied dc voltage. This means that positive ions caught somewhere in this assembly will fall to the lowest voltage region, i.e., between the inner and outer electrodes of the middle segment 112C, 113C. Since the normal FAIMS conditions continue to apply within each segment 112A–112E, 113A–113E, namely the inner electrode has an asymmetric waveform with DV=2500 V and the difference between the dc applied to the inner electrode 112 and the dc applied to the outer electrode 113 within that segment continues to be 12 V (a required compensation voltage in this example), then the ions will be focused in the normal way in the annular space between the inner and outer electrodes 112, 113. The flow of gas along the length of this FAIMS will not (at low gas flows, 1 L/min) be able to remove the ions which are located in the space within the middle segment 112C, 113C of this trap. For the ions to escape they must climb up the dc potential walls (of about +5 V in the Figure). At high gas flows, and at high ion density in which space charge is high, this escape might be possible. Nevertheless, there exists a trapping region which is totally electrical in nature, and the ions are held in place only by electric fields.

We claim:

1. An apparatus for selectively transmitting ions and trapping said ions within a defined 3-dimensional space, comprising:

a) at least one ionization source for producing ions;
b) a high field asymmetric waveform ion mobility spectrometer, comprising an analyzer region defined by a space between at least first and second spaced apart electrodes for connection, in use, to an electrical controller capable of supplying an asymmetric waveform voltage and a direct-current compensation voltage for selectively transmitting a selected ion type in said analyzer region between said electrodes at a given combination of asymmetric waveform voltage and compensation voltage, said analyzer region having a gas inlet and a gas outlet for providing, in use, a flow of gas through said analyzer region, said analyzer region further having an ion inlet for introducing a flow of ions produced by said ionization source into said analyzer region; and
c) a curved surface terminus provided on at least one of said electrodes, said terminus being a part of said one of said electrodes which part is closest to said gas outlet, said defined 3-dimensional space being located near said terminus, whereby, in use, said asymmetric waveform voltage, compensation voltage and gas flow are adjustable, so as to trap said transmitted ions within said 3-dimensional space.

2. The apparatus claimed in claim 1, wherein, said first and second electrodes comprise curved electrode bodies and provide a non-constant electric field therebetween, whereby, in use, said ions are selectively focussed in a focussing region created between said curved electrode bodies in said analyzer region.

3. The apparatus claimed in claim 2, wherein, said space between said electrodes defining said analyzer region is generally uniform.

4. The apparatus claimed in claim 3, wherein, said terminus is substantially a portion of a sphere.

5. The apparatus claimed in claim 2, where in, said first and second electrodes comprise outer and inner generally cylindrical coaxially aligned electrode bodies defining a generally annular space therebetween, said annular space forming said analyzer region, and said terminus being provided at an end of said inner cylindrical electrode body.

6. The apparatus claimed in claim 2, wherein, said analyzer region further includes an ion outlet for extracting ions from said analyzer region, said ion outlet being substantially aligned with said terminus and said defined 3-dimensional space, whereby, in use, said ions trapped in said 3-dimensional space may be released through said ion outlet.

7. The apparatus claimed in claim 6, wherein, said ion outlet is defined by an opening in said second electrode.

8. The apparatus claimed in claim 6, further comprising a mass spectrometer having a sampler orifice, said sampler orifice being positioned proximate to said ion outlet to receive said ions exiting said ion outlet.

9. A method for selectively transmitting and trapping ions within a defined 3-dimensional space, said method comprising the steps of:
a) providing at least one ionization source for producing ions;
b) providing an analyzer region defined by a space between at least first and second spaced apart electrodes, said analyzer region being in communication with a gas inlet, a gas outlet and an ion inlet, said ions produced by said ionization source being introduced into said analyzer region at said ion inlet;
c) providing an a symmetric waveform voltage and a direct-current compensation voltage, to at least one of said electrodes;
d) adjusting said asymmetric waveform voltage and said compensation voltage to selectively transmit a type of ion within said analyzer region;
e) providing a curved surface terminus on at least one of said electrodes, said defined 3-dimensional space being located near said terminus; and
f) providing a gas flow within said analyzer region flowing from said gas inlet to said gas outlet and adjusting said gas flow to trap said transmitted ions within and near said defined 3-dimensional space, said gas outlet being located near said terminus.

10. The method claimed in claim 9, wherein, said analyzer region is substantially at atmospheric pressure and substantially at room temperature.

11. The method claimed in claim 9, wherein, a non-constant electric field is provided between said first and second electrodes, whereby, said ions are selectively focussed in a focussing region created between said electrodes.

12. The method claimed in claim 11, further comprising the step of providing an ion outlet and supplying an extraction voltage at said ion outlet for extracting said trapped ions, said ion outlet being substantially aligned with said terminus and said defined 3-dimensional space.

13. The method claimed in claim 11, further comprising the step of further adjusting at least one of said asymmetric waveform voltage, compensation voltage and gas flow so as to provide near trapping conditions, whereby, said focussed ions tend to follow the curved surface of said terminus and are directed generally radially inwardly towards said ion outlet.

14. The method claimed in claim 11, wherein, said asymmetric waveform voltage and said compensation voltage are applied to one of said first and second electrodes, and another of said first and second electrodes is held at a voltage independent of said asymmetric waveform voltage and said compensation voltage.

15. An apparatus for selectively focussing ions and trapping said ions within a defined 3-dimensional space, comprising:
a) at least one ionization source for producing ions;
b) a segmented high field asymmetric waveform ion mobility spectrometer, comprising an analyzer region defined by spaces between a plurality of corresponding pairs of first and second spaced apart electrodes, for connection, in use, to an electrical controller capable of supplying an asymmetric waveform voltage, a direct current compensation voltage and a direct current segment offset voltage, each of said plurality of corresponding pairs of first and second spaced apart electrodes forming a segment and said segments being aligned in a row immediately adjacent to and electrically isolated from each other, said analyzer region having an ion inlet for introducing a flow of ions produced by said ionization source into said analyzer region.

16. The apparatus claimed in claim 15, wherein, said first and second electrodes in each segment comprise curved electrode bodies providing a non-constant electric field therebetween, said ions being selectively focussed in a focussing region created between said curved electrode bodies in said analyzer region.

17. The apparatus claimed in claim 16, wherein, said first and second electrodes in each segment comprise outer and inner generally cylindrical coaxially aligned electrode bodies with a generally annular space formed between them, said annular spaces formed in each of said segments collectively defining said analyzer region.

18. A method of selectively focussing ions and trapping said ions within a defined 3-dimensional space, comprising the steps of:
- a) providing at least one ionization source for producing ions;
- b) providing an analyzer region defined by spaces between a plurality of corresponding pairs of first and second spaced apart electrodes and providing a non-constant electric field between said first and second electrodes, each of said plurality of corresponding pairs of first and second spaced apart electrodes forming a segment and said segments being aligned in a row immediately adjacent to and electrically isolated from each other, said-analyzer region being in communication with an ion inlet, and introducing said ions produced by said ionization source into said analyzer region at said ion inlet;
- c) supplying an asymmetric waveform voltage to one of said first and second spaced apart electrodes in each of said segments;
- d) supplying a direct current compensation voltage to said one of said first and second spaced apart electrodes in each of said segments, said direct current compensation voltages supplied to each of said segments being independently adjustable;
- e) supplying a direct current segment offset voltage to another of said first and second spaced apart electrodes in each of said segments, said direct current segment offset voltages supplied to each of said segments being independently adjustable; and
- f) adjusting said direct current compensation voltages and said direct current segment offset voltages substantially equally, thereby providing a constant directs current potential across each corresponding pair of first and second electrodes in each of said segments, so as to focus desired ions between each corresponding pair of first and second electrodes in each of said segments at a given combination of said asymmetric voltage, direct current compensation voltage, and direct current segment offset voltage.

19. The method claimed in claim 18, further comprising the step of creating a direct current potential between adjacent segments so as to cause ions to move as between segments.

20. The method claimed in claim 19, wherein, a segment having a lower direct current potential is provided between at least two segments having higher direct current potentials, whereby, ions are trapped in a focussing region between first and second electrodes in said segment with a lower direct current potential.

21. The method claimed in claim 19, wherein, direct current potentials between adjacent segments form a decreasing gradient in a first direction, so as to cause said focussed ions to travel in said first direction.

22. The method claimed in claim 21, further comprising the step of providing a gas flow in a second direction substantially opposite to said first direction, and adjusting said gas flow, so as to trap said focussed ions in an intermediate segment.

23. An apparatus for selectively transmitting ions and/or trapping said ions within a defined 3-dimensional space, comprising:
- a) at least one ionization source for producing ions;
- b) a high field asymmetric waveform ion mobility spectrometer, comprising an analyzer region defined by a space between at least first and second spaced apart electrodes for connection, in use, to an electrical controller capable of supplying an asymmetric waveform voltage and a direct-current compensation voltage for selectively transmitting a selected ion type in said analyzer region between said electrodes at a given combination of asymmetric waveform voltage and compensation voltage, said analyzer region having a gas inlet and a gas outlet for providing, in use, a flow of gas through said analyzer region, said analyzer region further having an ion inlet for introducing a flow of ions produced by said ionization source into said analyzer region; and,
- c) a terminus provided on at least one of said electrodes and shaped for directing said ions generally radially inwardly toward said gas outlet, said terminus being a part of said one of said electrodes which part is closest to said gas outlet, said defined 3-dimensional space being located near said terminus, whereby, in use, said asymmetric waveform voltage, compensation voltage and gas flow are adjustable, so as to trap said transmitted ions within said 3-dimensional space.

24. The apparatus claimed in claim 23, wherein, said first and second electrodes comprise curved electrode bodies and provide a non-constant electric field therebetween, whereby, in use, said ions are selectively focused in a focusing region created between said curved electrode bodies in said analyzer region.

25. The apparatus claimed in claim 24, wherein, said space between said electrodes defining said analyzer region is generally uniform.

26. The apparatus claimed in claim 25, wherein said terminus is tapered toward said gas outlet.

27. The apparatus claimed in claim 26, wherein, said terminus is provided with a curved surface.

28. The apparatus claimed in claim 27, wherein, said curved surface is substantially a portion of a sphere.

29. The apparatus claimed in claim 24, wherein, said analyzer region further includes an ion outlet for extracting ions from said analyzer region, said ion outlet being substantially aligned with said terminus and said defined 3-dimensional space, whereby, in use, said selectively transmitted ions and/or said ions trapped in said 3-dimensional space may be released through said ion outlet.

30. The apparatus claimed in claim 29, wherein, said first and second electrodes comprise outer and inner generally cylindrical coaxially aligned electrode bodies defining a generally annular space therebetween, said annular space forming said analyzer region, and said terminus being provided at an end of said inner cylindrical electrode body.

31. The apparatus claimed in claim 30, wherein, said terminus is relatively moveable to the ion outlet.

32. The apparatus claimed in claim 29, wherein, said ion outlet is defined by an opening in said second electrode.

33. The apparatus claimed in claim 29, further comprising a mass spectrometer having a sampler orifice, said sampler orifice being positioned proximate to said ion outlet to receive said ions exiting said ion outlet.

34. The apparatus claimed in claim 33, wherein, said mass spectrometer is a time of flight mass spectrometer.

35. A method for selectively transmitting and/or trapping ions within a defined 3-dimensional space, said method comprising the steps of:
- a) providing at least one ionization source for producing ions;
- b) providing an analyzer region defined by a space between at least first and second spaced apart electrodes, said analyzer region being in communication with a gas inlet, a gas outlet and an ion inlet, said ions produced by said ionization source being introduced into said analyzer region at said ion inlet;

c) providing a terminus on at least one of said electrodes, said terminus being part of said one of said electrodes which part is closest to said gas outlet, said terminus shaped for directing said ions generally radially inwardly toward said gas outlet;

d) providing an asymmetric waveform voltage and a direct-current compensation voltage, to at least one of said electrodes;

e) adjusting said asymmetric waveform voltage and said compensation voltage to selectively transmit a type of ion within said analyzer region; and, f) providing a gas flow within said analyzer region flowing from said gas inlet to said gas outlet and adjusting said gas flow to trap said transmitted ions within and near said defined 3-dimensional space, said gas outlet being located near said terminus.

36. The method claimed in claim 35, wherein, said analyzer region is substantially at atmospheric pressure and substantially at room temperature.

37. The method claimed in claim 35, wherein, a non-constant electric field is provided between said first and second electrodes, whereby, said ions are selectively focused in a focusing region created between said electrodes.

38. The method claimed in claim 37, further comprising the step of providing an ion outlet and supplying an extraction voltage at said ion outlet for extracting said trapped ions, said ion outlet being substantially aligned with said terminus and said defined 3-dimensional space.

39. The method claimed in claim 37, further comprising the step of further adjusting at least one of said asymmetric waveform voltage, compensation voltage and gas flow so as to provide near trapping conditions, whereby, said focused ions tend to follow a curved surface of said terminus and are directed generally radially inwardly towards said ion outlet.

40. The method claimed in claim 37, wherein, said asymmetric waveform voltage and said compensation voltage are applied to one of said first and second electrodes, and another of said first and second electrodes is held at a voltage independent of said asymmetric waveform voltage and said compensation voltage.

41. An apparatus for selectively focusing ions and trapping said ions within a defined 3-dimensional space, comprising:

a) at least one ionization source for producing ions;

b) a segmented high field asymmetric waveform ion mobility spectrometer, comprising an analyzer region defined by spaces between a plurality of corresponding pairs of first and second spaced apart electrodes, for connection, in use, to an electrical controller capable of supplying an asymmetric waveform voltage, a direct current compensation voltage and a direct current segment offset voltage, each of said plurality of corresponding pairs of first and second spaced apart electrodes forming a segment and said segments being aligned in a row immediately adjacent to and electrically isolated from each other, said analyzer region having an ion inlet for introducing a flow of ions produced by said ionization source into said analyzer region.

42. The apparatus claimed in claim 41, wherein, said first and second electrodes in each segment comprise curved electrode bodies providing a non-constant electric field therebetween, said ions being selectively focused in a focusing region created between said curved electrode bodies in said analyzer region.

43. The apparatus claimed in claim 42, wherein, said first and second electrodes in each segment comprise outer and inner generally cylindrical coaxially aligned electrode bodies with a generally annular space formed between them, said annular spaces formed in each of said segments collectively defining said analyzer region.

44. A method of selectively focusing ions and trapping said ions within a defined 3-dimensional space, comprising the steps of:

a) providing at least one ionization source for producing ions;

b) providing an analyzer region defined by spaces between a plurality of corresponding pairs of first and second spaced apart electrodes and providing a non-constant electric field between said first and second electrodes, each of said plurality of corresponding pairs of first and second spaced apart electrodes forming a segment and said segments being aligned in a row immediately adjacent to and electrically isolated from each other, said analyzer region being in communication with an ion inlet, and introducing said ions produced by said ionization source into said analyzer region at said ion inlet;

c) supplying an asymmetric waveform voltage to one of said first and second spaced apart electrodes in each of said segments;

d) supplying a direct current compensation voltage to said one of said first and second spaced apart electrodes in each of said segments, said direct current compensation voltages supplied to each of said segments being independently adjustable;

e) supplying a direct current segment offset voltage to another of said first and second spaced apart electrodes in each of said segments, said direct current segment offset voltages supplied to each of said segments being independently adjustable; and, f) adjusting said direct current compensation voltages and said direct current segment offset voltages substantially equally, thereby providing a constant direct current potential across each corresponding pair of first and second electrodes in each of said segments, so as to focus desired ions between each corresponding pair of first and second electrodes in each of said segments at a given combination of said asymmetric voltage, direct current compensation voltage, and direct current segment offset voltage.

45. The method claimed in claim 44, further comprising the step of creating a direct current potential between adjacent segments so as to cause ions to move as between segments.

46. The method claimed in claim 45, wherein, a segment having a lower direct current potential is provided between at least two segments having higher direct current potentials, whereby, ions are trapped in a focusing region between first and second electrodes in said segment with a lower direct current potential.

47. The method claimed in claim 45, wherein, direct current potentials between adjacent segments form a decreasing gradient in a first direction, so as to cause said focused ions ions to travel in said first direction.

48. The method claimed in claim 47, further comprising the step of providing a gas flow in a second direction substantially opposite to said first direction, and adjusting said gas flow, so as to trap said focused ions in an intermediate segment.

* * * * *

UNITED STATES PATENT AND TRADEMARK OFFICE
CERTIFICATE OF CORRECTION

PATENT NO. : 6,621,077 B1
DATED : September 16, 2003
INVENTOR(S) : Guevremont and Purves It is certified that error appears in the above-identified patent and that said Letters Patent is hereby corrected as shown below:

Column 37,
Line 35, "where in" should read -- wherein --.
Line 65, "a symmetric" should read -- asymmetric --.

Column 39,
Line 34, "directs current" should read -- direct current --.

Column 41-42,
Please delete claims 41-48.

Signed and Sealed this

Eleventh Day of May, 2004

JON W. DUDAS
*Acting Director of the United States Patent and Trademark Office*